US009476033B2

(12) United States Patent
Samal et al.

(10) Patent No.: US 9,476,033 B2
(45) Date of Patent: *Oct. 25, 2016

(54) RECOMBINANT NEWCASTLE DISEASE VIRUSES USEFUL AS VACCINES OR VACCINE VECTORS

(75) Inventors: Siba K. Samal, College Park, MD (US); Zhuhui Huang, College Park, MD (US)

(73) Assignee: The University of Maryland, College Park, College Park, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/188,392

(22) Filed: Jul. 21, 2011

(65) Prior Publication Data

US 2012/0064112 A1  Mar. 15, 2012

Related U.S. Application Data

(63) Continuation of application No. 10/440,419, filed on May 19, 2003, now abandoned, which is a continuation-in-part of application No. 09/926,431, filed as application No. PCT/US00/06700 on May 5, 2000, now Pat. No. 7,244,558.

(60) Provisional application No. 60/381,462, filed on May 7, 2002, provisional application No. 60/132,597, filed on May 5, 1999, provisional application No. 60/171,072, filed on Dec. 16, 1999.

(51) Int. Cl.
| A61K 39/295 | (2006.01) |
| C12N 15/63 | (2006.01) |
| A61P 31/12 | (2006.01) |
| C12N 7/00 | (2006.01) |
| C12N 15/86 | (2006.01) |
| A61K 39/00 | (2006.01) |

(52) U.S. Cl.
CPC ............... *C12N 7/00* (2013.01); *C12N 15/86* (2013.01); *A61K 2039/525* (2013.01); *C12N 2760/18143* (2013.01); *C12N 2840/203* (2013.01)

(58) Field of Classification Search
None
See application file for complete search history.

(56) References Cited

U.S. PATENT DOCUMENTS

| 6,121,416 A * | 9/2000 | Clark et al. .................. 530/326 |
| 6,146,642 A | 11/2000 | Garcia-Sastre et al. |
| 6,451,323 B1 * | 9/2002 | Garcia-Sastre et al. ... 424/214.1 |
| 7,244,558 B1 * | 7/2007 | Samal et al. .................. 435/5 |

OTHER PUBLICATIONS

Krishnamurthy et al. (Journal of General Medicine, 1998, vol. 79, p. 2419-2424).*
Krishnamurthy et al. (Virology, 2000, vol. 278, p. 168-182).*
Philippe Calain and Laurent Roux, "The Rule of Six, a Basic Feature for Efficient Replication of Sendai Virus Defective Interfering RNA," Journal of Virology, Aug. 1993, pp. 4822-2830, vol. 67, No. 8.
Robert A. Lamb and Griffith D. Parks, "*Paramyxoviridae*: The Viruses and Their Replication," Chapter 41, Section II: Specific Virus Families, pp. 1449-1496.
B.P.H. Peeters et al., "Genome replication o fNewcastle disease virus: involvement of the rule-of-six," Arch Virol (2000) 145: pp. 1829-1845.
Siba K. Samal and Peter L. Collins, "RNA Replication by a Respiratory Syncytial Virus RNA Analog Does Not Obey the Rule of Six and Retains a Nonviral Trinucleotide Extension at the Leader End," Journal of Virology, Aug. 1996, pp. 5075-5082, vol. 70, No. 8.
Collins, et al. (PNAS, 1995, vol. 92, pp. 11563-11567).
Phillips, et al. (Archives in Virology, 1998, vol. 143, pp. 1993-2002.
Fahey, et al. Journal of General Virology, 1989, vol. 70, pp. 1473-1481.
Peeters, et al. Gerneration of a recombinant chimeric Newcastle disease virus vaccine that allows serological differentiation between accinated and infected nimals. (Feb. 2001) Vaccine 19, pp. 1616-1627.
Mebastion, et al. A recombinant Newcastle Disease Virus with Low-Level V protein expressions is immunogenic and lacks pathogenicity for chicken embryos. (Jan. 2001) Journal of Virology, pp. 420-428.
Darteil, et al. Herpesvirus of turkey recombinant viruses expressing infectious bursal disease virus (IBVD) VP2 immunogen induce protection against an IBVD virulent challenge in chickens. (1995) Virology 211, pp. 481-490.
Huang, et al. Recombinant Newcastle disease virus as a vaccine vector. (2002) Poultry Science, pp. 899-906.
Yusoff, K. et al., "Location of Neutralizing Epitopes on the Fusion Protein of Newcastle Disease Virus Strain Beaudette C", J. Gen. Virol. 1989, vol. 70, pp. 3105-3109.
Krishnamurthy, S. et al., "Nucleotide Sequences of the Trailer, Nucleocapsid Protein gene and Intergenic regions of Newcastle Disease Virus Strain Beaudette C and Completion of the Entire Genome Sequence", Journal of General Virology, 1998, vol. 79, pp. 2419-2424.

(Continued)

*Primary Examiner* — Agnieszka Boesen
(74) *Attorney, Agent, or Firm* — Arent Fox LLP

(57) ABSTRACT

The present invention concerns an antigenomic RNA of Newcastle Disease virus (NDV) carrying one or more foreign genes inserted before NP gene, between P and M genes, and/or between HN and L genes. The invention is also directed toward a cDNA encoding a recombinant antigenomic RNA having one or more foreign genes inserted according to the invention, a cell containing the cDNA, a plasmid comprising the cDNA, a cell containing the plasmid, a cell containing the recombinant antigenomic RNA, and a recombinant NDV containing the recombinant antigenomic RNA of the invention, such as a recombinant NDV carrying one or more foreign genes recovered from transcription of the cDNA or the plasmid in a competent cell. The recombinant NDV carrying the one or more foreign genes can be used as a vaccine or vaccine vector.

60 Claims, 16 Drawing Sheets

(56) References Cited

OTHER PUBLICATIONS

Schaper, U.M. et al., "Nucleotide Sequence of the Envelope Protein genes of a Highly Virulent, Neurotropic strain of Newcastle Disease Virus", Virology, 1988, vol. 165, pp. 291-295.

Yusoff, K. et al., "Nucleotide Sequence Analysis of the L Gene of Newcastle Disease Virus: Homologies with Sendai and Vesicular Stomatitis Viruses", Nucleic Acids Research 1987, vol. 15, No. 10, pp. 3961-3976.

Daskalakis, S. et al., "Nucleotide Sequence of the Phosphoprotein (P) Gene of Newcastle Disease Virus (Strain Beaudette C)", Nucleic Acids Research, 1992, vol. 20, No. 3, p. 616.

* cited by examiner

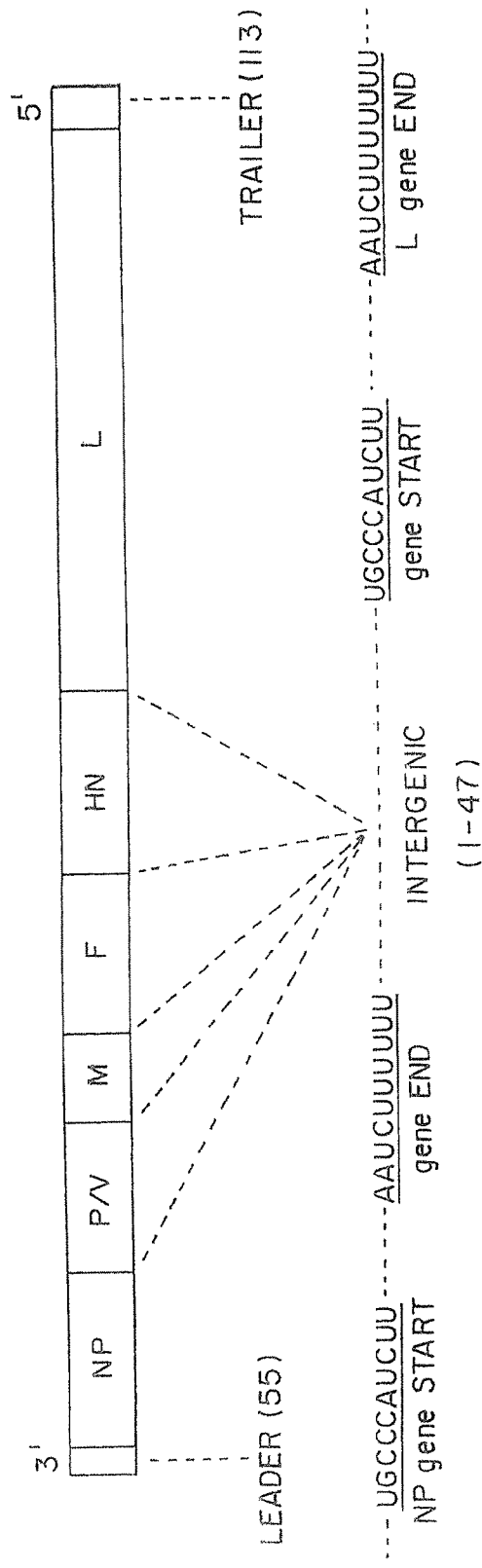

FIG. 2

Leader (55nt)

1                                                          55
3' UGGUUUGUCUCUAGGCAUUCAAUGCUAUUUCCGCUUCCUGUUAACUUCAACG

GENE END ─── INTERGENE ─── GENE START

56        NP
                                              UGCCCAUCUU——//
                                                        (1745nt)
                                              1804      P
                                              UGCCCAUCUU——//
                                                        (1451nt)
                                              3256      M
                                              UGCCCAUCUU——//
                                                        (1241nt)
                                              4498      F
                                              UGCCCAUCUU——//
                                                        (1792nt)
                                              6321      HN
                                              UGCCCAUCUU——//
                                                        (2002nt)
                                              8370      L
                                              UGCCCAUCCU——//
                                                        (6704nt)

1802
NP ——AAUCUUUUUUA
//

3254
P  ——AAUCUUUUUUA
//

4496
M  ——AAUCUUUUUUG
//

6289
F  ——AAUCUUUUUU GAUGGCCAAACAUCUACUGGUUCCUGCUAUA
//

8322
HN ——AAUCUUUUUU ACAUUCACCGUUACUCUAUGUUCCGUUUUGUCGAGUACCAUUAUCA
//

15073
L  ——AAUCUUUUUU
//

Trailer (113nt)

15186
15074 AACUUGAGGCUGAGGAAUCUAGAGCUUAAGCUUGAGUUAUUUACAGAAUUUUUUCC
AACGCGUGUAAUAAGAACUCACAUCAGAACAAUAAGUGGUUUAGAAACAAACCA 5'

FIG. 4

FIG. 5
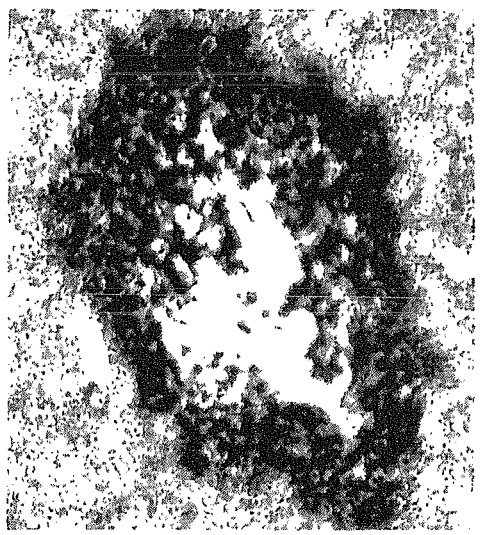
(a) rLaSota/CAT
(b) rLaSota

FIG. 14

SUPPORT PLASMIDS

VACCINIA MVA/T7
INFECT p+NDV TRANSFECT

TRANSFECT

NP

P

L

HEp2 CELL

3 DAYS

INFECTIOUS NDV

FIG. 16
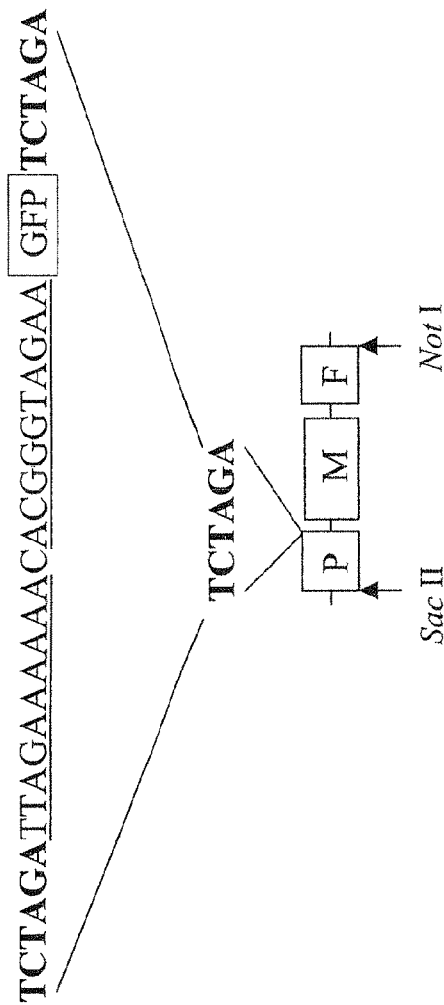
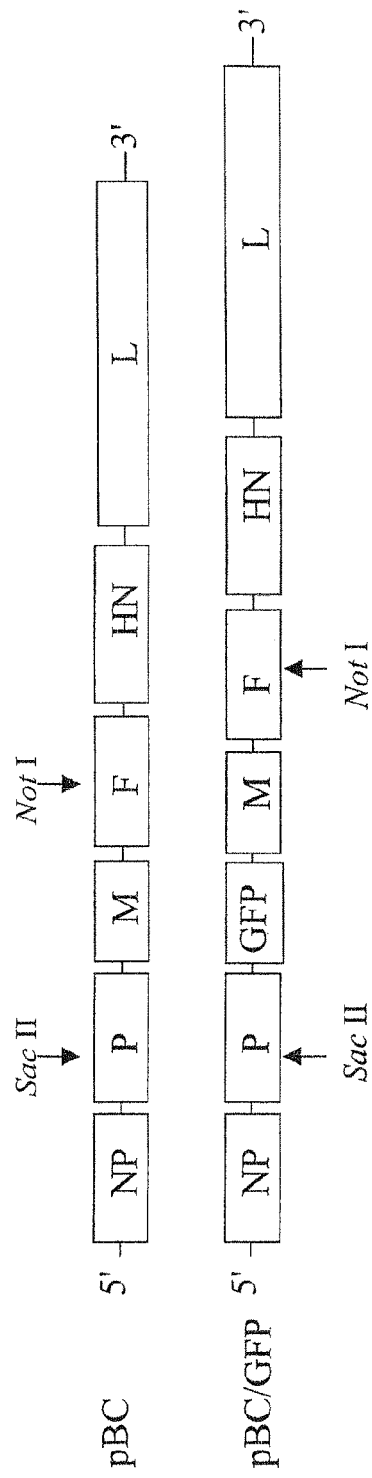

SEQUENCE LISTING

<160> NUMBER OF SEQ ID NOS: 58

<210> SEQ ID NO 1
<211> LENGTH: 11
<212> TYPE: RNA
<213> ORGANISM: Newcastle disease virus

<400> SEQUENCE: 1
uuuuuuucua a                                                      11

<210> SEQ ID NO 2
<211> LENGTH: 10
<212> TYPE: RNA
<213> ORGANISM: Newcastle disease virus

<400> SEQUENCE: 2
uucuacccgu                                                        10

<210> SEQ ID NO 3
<211> LENGTH: 10
<212> TYPE: RNA
<213> ORGANISM: Newcastle disease virus

<400> SEQUENCE: 3
uuuuuucuaa                                                        10

<210> SEQ ID NO 4
<211> LENGTH: 124
<212> TYPE: RNA
<213> ORGANISM: Newcastle disease virus

<400> SEQUENCE: 4
accaaacaaa gauuggguga auaacaagac uacacucaag aauaauugug cgcaaccuuu    60
uuuuaagaca uuuauuugag uucgaauucg agaucuaagg agucggaguu caauuuuuuu    120
cuaa    124

<210> SEQ ID NO 5
<211> LENGTH: 10
<212> TYPE: RNA
<213> ORGANISM: Newcastle disease virus

<400> SEQUENCE: 5
uccuacccgu    10

<210> SEQ ID NO 6
<211> LENGTH: 58
<212> TYPE: RNA
<213> ORGANISM: Newcastle disease virus

<400> SEQUENCE: 6
acuauuuacc augagcuguu uugccuugua ucucauugcc acuuacauuu uuucuuaa    58

<210> SEQ ID NO 7
<211> LENGTH: 41
<212> TYPE: RNA
<213> ORGANISM: Newcastle disease virus

<400> SEQUENCE: 7
auaucguccu uuggucaucu acaaccggua guuuuuucua a    41

<210> SEQ ID NO 8
<211> LENGTH: 11
<212> TYPE: RNA
<213> ORGANISM: Newcastle disease virus

<400> SEQUENCE: 8
guuuuuucua a    11

<210> SEQ ID NO 9
<211> LENGTH: 12
<212> TYPE: RNA
<213> ORGANISM: Newcastle disease virus

<400> SEQUENCE: 9
auuuuuucuu aa    12

<210> SEQ ID NO 10
<211> LENGTH: 12
<212> TYPE: RNA
<213> ORGANISM: Newcastle disease virus

<400> SEQUENCE: 10
auuuuuuucu aa    12

<210> SEQ ID NO 11
<211> LENGTH: 55
<212> TYPE: RNA
<213> ORGANISM: Newcastle disease virus

<400> SEQUENCE: 11
gcaacuucaa uugcuccuuc gccuuuuauc guaacuacg gauucucugu uuggu    55

<210> SEQ ID NO 12
<211> LENGTH: 29
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 12
ttagaaaaaa cacgggtaga agtttaaac                                           29

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gtttaaactc tgccaactat g                                                   21

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gcaacaccgg tacgggtaga aggac                                               25

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
atggagaaaa aaatcactgg a                                                   21

<210> SEQ ID NO 16
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gcatcaccgg tatttttct aatcgag                                              27

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
ttacgccccg ccctgccact c                                                   21

<210> SEQ ID NO 18
<211> LENGTH: 27
<212> TYPE: DNA
<213> ORGANISM: Artificial Sequence
<220> FEATURE:
```

-continued

```
<223> OTHER INFORMATION: Description of Artificial Sequence: Synthetic
      oligonucleotide

<400> SEQUENCE: 18
tctagattag aaaaaacacg ggtagaa                                        27

<210> SEQ ID NO 19
<211> LENGTH: 10
<212> TYPE: DNA
<213> ORGANISM: Newcastle disease virus

<400> SEQUENCE: 19
ttagaaaaaa                                                           10

<210> SEQ ID NO 20
<211> LENGTH: 10
<212> TYPE: DNA
<213> ORGANISM: Newcastle disease virus

<400> SEQUENCE: 20
acgggtagaa                                                           10

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tcccctggta tttattcctg c                                              21

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gttggccacc cagtccccga                                                20

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
cgcatacagc aggctatctt atc                                            23

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gggtcatatt ctatacatgg c                                              21
```

<210> SEQ ID NO 25
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gctagtttaa acatggagaa aaaaatcact ggatatacc                    39

<210> SEQ ID NO 26
<211> LENGTH: 66
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gctagtttaa acttctaccc gtgttttttc taatctgcag ttacgccccg ccctgccact    60
catcgc                                                              66

<210> SEQ ID NO 27
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ctgaggcgcg cctaatacga ctcactatag gaccaaacag agaatccgtg agttag      56

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ggtgccgcgg aaacagccag g                                           21

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
aacagcggcc gcagctctga t                                           21

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
aactacgcgt tgtagatgac caaag                                       25

<210> SEQ ID NO 31
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
caaaatacgt aatggtaaat aatacgggta ggacatg                                    37

<210> SEQ ID NO 32
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ttcagctaag ctgacaaaga agttaaggaa ctg                                        33

<210> SEQ ID NO 33
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
tcagaggcct agacaatatt gtct                                                  24

<210> SEQ ID NO 34
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gtttccgcgg ctgggttgac tcccct                                                26

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gagctgcggc cgctgttatt tg                                                    22

<210> SEQ ID NO 36
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
tacaacgcgt agttttttct taactc                                                26

<210> SEQ ID NO 37
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 37
gcactacgta ttttgccttg tatctc                                          26

<210> SEQ ID NO 38
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 38
ttcagcttag cgaagatccg tccattaact                                      30

<210> SEQ ID NO 39
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 39
gtctaggcct cttactctca ggtaatag                                        28

<210> SEQ ID NO 40
<211> LENGTH: 63
<212> TYPE: DNA
<213> ORGANISM: Artificial Sequence
<220> FEATURE:
<223> OTHER INFORMATION: Description of Artificial Sequence: Synthetic primer

<400> SEQUENCE: 40
gatccggacc gcgaggaggt ggagatgcca tgccgaccaa acaaagattt ggtgaatgac     60
gag                                                                   63

<210> SEQ ID NO 41
<211> LENGTH: 57
<212> TYPE: DNA
<213> ORGANISM: Artificial Sequence
<220> FEATURE:
<223> OTHER INFORMATION: Description of Artificial Sequence: Synthetic primer

<400> SEQUENCE: 41
actggggcgc gcctaatacg actcactata ggaccaaaca gagaatccgt aagttag        57

<210> SEQ ID NO 42
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 42
agacccgcgg ctgggttgac ttccctg                                         27

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
agacccgcgg aaacagccag g                                          21

<210> SEQ ID NO 44
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
gcaggggccc atcttgcacc tagaa                                      25

<210> SEQ ID NO 45
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45 acagggccc cagaccttct accaa                                       25

<210> SEQ ID NO 46
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
atcgacgcgt agttttttct aaactctc                                   28

<210> SEQ ID NO 47
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
atcgacgcgt tgtagatgac caaag                                      25

<210> SEQ ID NO 48
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
gcacaccggt agctgttttg ccttgtatc                                  29

```
<210> SEQ ID NO 49
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
gcacaccggt aaatagtacg ggtaggacat g                              31

<210> SEQ ID NO 50
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
ttcagcttag cgaagatccg tccattaagt                                30

<210> SEQ ID NO 51
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
aagccttaag aacaatgttt gggcttgcaa c                              31

<210> SEQ ID NO 52
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
aagccttaag aaacatacgc aaagagtcct                                30

<210> SEQ ID NO 53
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
tcagaggcct tcttactctc agataataga g                              31

<210> SEQ ID NO 54
<211> LENGTH: 67
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
atgccggacc gcgaggaggt ggagatgcca tgccgaccca ccaaacaaag atttggtgaa    60
taacaag                                                             67
```

<210> SEQ ID NO 55
<211> LENGTH: 15900
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55

```
accaaacaga gaatccgtga gttacgataa aaggcgaaag agcaattgaa gtcgcacggg      60
tagaaggtgt gaatctcgag tgcgagcccg aagcacaaac tcgagaaagc cttctgccaa     120
cgtttaaaca tggagaaaaa aatcactgga tataccaccg ttgatatatc ccaatggcat     180
cgtaaagaac attttgaggc atttcagtca gttgctcaat gtacctataa ccagaccgtt     240
cagctggata ttacggcctt tttaaagacc gtaaagaaaa ataagcacaa gttttatccg     300
gcctttattc acattcttgc ccgcctgatg aatgctcatc cggaattccg tatggcaatg     360
aaagacggtg agctggtgat atgggatagt gttcacccct tgttacaccgt tttccatgag     420
caaactgaaa cgttttcatc gctctggagt gaataccacg acgatttccg gcagtttcta     480
cacatatatt cgcaagatgt ggcgtgttac ggtgaaaacc tggcctattt ccctaaaggg     540
tttattgaga atatgttttt cgtctcagcc aatccctggg tgagtttcac cagttttgat     600
ttaaacgtgg ccaatatgga caacttcttc gcccccgttt tcaccatggg caaatactat     660
acgcaaggcg acaaggtgct gatgccgctg gcgattcagg ttcatcatgc cgtttgtgat     720
ggcttccatg tcggcagaat gcttaatgaa ttacaacagt actgcgatga gtggcagggc     780
ggggcgtaac tgcagattag aaaaaacacg ggtagaagtt taaactaggt gcaagatgtc     840
ttccgtattt gatgagtacg aacagctcct cgcggctcag actcgcccca atggagctca     900
tggaggggga gaaaaaggga gtaccttaaa agtagacgtc ccggtattca ctcttaacag     960
tgatgaccca gaagatagat ggagctttgt ggtattctgc ctccggattg ctgttagcga    1020
agatgccaac aaaccactca ggcaaggtgc tctcatatct ctttttatgct cccactcaca    1080
ggtaatgagg aaccatgttg cccttgcagg gaaacagaat gaagccacat ggccgtgct    1140
tgagattgat ggctttgcca acggcacgcc ccagttcaac aataggagtg gagtgtctga    1200
agagagagca cagagatttg cgatgatagc aggatctctc cctcgggcat gcagcaacgg    1260
aaccccgttc gtcacagccg gggccgaaga tgatgcacca aagacatca ccgataccct    1320
ggagaggatc ctctctatcc aggctcaagt atgggtcaca gtagcaaaag ccatgactgc    1380
gtatgagact gcagatgagt cggaaacaag gcgaatcaat aagtatatgc agcaaggcag    1440
ggtccaaaag aaatacatcc tctaccccgt atgcaggagc acaatccaac tcacgatcag    1500
acagtctctt gcagtccgca tcttttttggt tagcgagctc aagagaggcc gcaacacggc    1560
aggtggtacc tctacttatt ataacctggt aggggacgta gactcataca tcaggaatac    1620
cgggcttact gcattcttct tgacactcaa gtacggaatc aacaccaaga catcagccct    1680
tgcacttagt agcctctcag gcgacatcca gaagatgaag cagctcatgc gtttgtatcg    1740
gatgaaagga gataatgcgc cgtacatgac attacttggt gatagtgacc agatgagctt    1800
tgcgcctgcc gagtatgcac aactttactc ccttgccatg ggtatggcat cagtcctaga    1860
taaaggtact gggaaatacc aatttgccag ggactttatg agcacatcat ctggagact    1920
tggagtagag tacgctcagg ctcagggaag tagcattaac gaggatatgg ctgccgagct    1980
aaagctaacc ccagcagcaa ggagggggcct ggcagctgct gcccaacggg tctccgagga    2040
```

```
gaccagcagc atagacatgc ctactcaaca agtcggagtc ctcactgggc ttagcgaggg    2100
ggggtcccaa gctctacaag gcggatcgaa tagatcgcaa gggcaaccag aagccgggga    2160
tggggagacc caattcctgg atctgatgag agcggtagca aatagcatga gggaggcgcc    2220
aaactctgca cagggcactc cccaatcggg gcctccccca actcctgggc catcccaaga    2280
taacgacacc gactgggggt attgatggac aaacccagc ctgcttccac aaaaacatcc      2340
caatgccctc acccgtagtc gaccctcga tttgcggctc tatatgacca caccctcaaa     2400
caaacatccc cctctttcct ccctccccct gctgtacaac tccgcacgcc ctagatacca    2460
caggcacaat gcggctcact aacaatcaaa acagagccga gggaattaga aaaagtacg     2520 ggtagaagag ggatattcag agatcagggc aagtctcccg agtctctgct ctctcctcta    2580
cctgatagac caggacaaac atggccacct ttacagatgc agagatcgac gagctatttg    2640
agacaagtgg aactgtcatt gacaacataa ttacagccca gggtaaacca gcagagactg    2700
ttggaaggag tgcaatccca caaggcaaga ccaaggtgct gagcgcagca tgggagaagc    2760
atgggagcat ccagccaccg gccagtcaag acaaccccga tcgacaggac agatctgaca    2820
aacaaccatc cacacccgag caaacgaccc cgcatgacag cccgccggcc acatccgccg    2880
accagccccc cacccaggcc acagacgaag ccgtcgacac acagctcagg accggagcaa    2940
gcaactctct gctgttgatg cttgacaagc tcagcaataa atcgtccaat gctaaaaagg    3000
gcccatggtc gagccccaa gagggaatc accaacgtcc gactcaacag caggggagtc       3060
aacccagccg cggaaacagt caggaaagac cgcagaacca agtcaaggcc gcccctggaa    3120
accagggcac agacgtgaac acagcatatc atggacaatg ggaggagtca caactatcag    3180
ctggtgcaac ccctcatgct ctccgatcaa ggcagagcca agacaatacc cttgtatctg    3240
cggatcatgt ccagccacct gtagactttg tgcaagcgat gatgtctatg atggaggcga    3300
tatcacagag agtaagtaag gtcgactatc agctagatct tgtcttgaaa cagacatcct    3360
ccatccctat gatgcggtcc gaaatccaac agctgaaaac atctgttgca gtcatggaag    3420
ccaacttggg aatgatgaag attctggatc ccggttgtgc caacatttca tctctgagtg    3480
atctacgggc agttgcccga tctcacccgg ttttagtttc aggccctgga gacccctctc    3540
cctatgtgac acaaggaggc gaaatggcac ttaataaact ttcgcaacca gtgccacatc    3600
catctgaatt gattaaaccc gccactgcat gcgggcctga tataggagtg gaaaaggaca    3660
ctgtccgtgc attgatcatg tcacgcccaa tgcacccgag ttcttcagcc aagctcctaa    3720
gcaagttaga tgcagccggg tcgatcgagg aaatcaggaa aatcaagcgc cttgctctaa    3780
atggctaatt actactgcca cacgtagcgg gtccctgtcc actcggcatc acacggaatc    3840
tgcaccgagt tcccccccgc agacccaagg tccaactctc caagcggcaa tcctctctcg    3900
cttcctcagc cccactgaat ggtcgcgtaa ccgtaattaa tctagctaca tttaagatta    3960
agaaaaaata cgggtagaat tggagtgccc caattgtgcc aagatggact catctaggac    4020
aattgggctg tactttgatt ctgcccattc ttctagcaac ctgttagcat ttccgatcgt    4080
cctacaaggc acaggagatg ggaagaagca aatcgccccg caatatagga tccagcgcct    4140
tgacttgtgg actgatagta aggaggactc agtattcatc accacctatg gattcatctt    4200
tcaagttggg aatgaagaag ccactgtcgg catgatcgat gataaaccca gcgcgagtt    4260 actttccgct gcgatgctct gcctaggaag cgtcccaaat accggagacc ttattgagct    4320
ggcaagggcc tgtctcacta tgatagtcac atgcaagaag agtgcaacta atactgagag    4380
```

```
aatggttttc tcagtagtgc aggcacccca agtgctgcaa agctgtaggg ttgtggcaaa    4440
caaatactca tcagtgaatg cagtcaagca cgtgaaagcg ccagagaaga ttcccgggag    4500
tggaacccta gaatacaagg tgaactttgt ctccttgact gtggtaccga agaaggatgt    4560
ctacaagatc cctgctgcag tattgaaggt ttctggctcg agtctgtaca atcttgcgct    4620
caatgtcact attaatgtgg aggtagaccc gaggagtcct ttggttaaat ctctgtctaa    4680
gtctgacagc ggatactatg ctaacctctt cttgcatatt ggacttatga ccaccgtaga    4740
taggaagggg aagaaagtga catttgacaa gctggaaaag aaaataagga gccttgatct    4800
atctgtcggg ctcagtgatg tgctcgggcc ttccgtgttg gtaaaagcaa gaggtgcacg    4860
gactaagctt ttggcacctt tcttctctag cagtgggaca gcctgctatc ccatagcaaa    4920
tgcttctcct caggtggcca agatactctg gagtcaaacc gcgtgcctgc ggagcgttaa    4980
aatcattatc caagcaggta cccaacgcgc tgtcgcagtg accgccgacc acgaggttac    5040
ctctactaag ctggagaagg ggcacaccct tgccaaatac aatcctttta agaaataagc    5100
tgcgtctctg agattgcgct ccgcccactc acccagatca tcatgacaca aaaaactaat    5160
ctgtcttgat tatttacagt tagtttacct gtctatcaag ttagaaaaaa cacgggtaga    5220
agattctgga tcccggttgg cgccctccag gtgcaagatg ggctccagac cttctaccaa    5280
gaacccagca cctatgatgc tgactatccg ggttgcgctg gtactgagtt gcatctgtcc    5340
ggcaaactcc attgatggca ggcctcttgc agctgcagga attgtggtta caggagacaa    5400
agccgtcaac atatacacct catcccagac aggatcaatc atagttaagc tcctcccgaa    5460
tctgcccaag gataaggagg catgtgcgaa agccccttg gatgcataca acaggacatt    5520
gaccactttg ctcaccccc ttggtgactc tatccgtagg atacaagagt ctgtgactac    5580
atctggaggg gggagacagg ggcgccttat aggcggcatt attggcggtg tggctcttgg    5640
ggttgcaact gccgcacaaa taacagcggc cgcagctctg atacaagcca aacaaaatgc    5700
tgccaacatc ctccgactta agagagcat tgccgcaacc aatgaggctg tgcatgaggt    5760
cactgacgga ttatcgcaac tagcagtggc agttgggaag atgcagcagt tgttaatga    5820 ccaatttaat aaaacagctc aggaattaga ctgcatcaaa attgcacagc aagttggtgt    5880
agagctcaac ctgtacctaa ccgaattgac tacagtattc ggaccacaaa tcacttcacc    5940
tgctttaaac aagctgacta ttcaggcact ttacaatcta gctggtggaa atatggatta    6000
cttattgact aagttaggtg tagggaacaa tcaactcagc tcattaatcg gtagcggctt    6060
aatcaccggt aaccctattc tatacgactc acagactcaa ctcttgggta tacaggtaac    6120
tctaccttca gtcgggaacc taaataatat gcgtgccacc tacttggaaa ccttatccgt    6180
aagcacaacc aggggatttg cctcggcact tgtcccaaaa gtggtgacac aggtcggttc    6240
tgtgatagaa gaacttgaca cctcatactg tatagaaact gacttagatt tatattgtac    6300
aagaatagta acgttcccta tgtcccctgg tatttattcc tgcttgagcg gcaatacgtc    6360
ggcctgtatg tactcaaaga ccgaaggcgc acttactaca ccatacatga ctatcaaagg    6420
ttcagtcatc gccaactgca gatgacaac atgtagatgt gtaaacccc cgggtatcat    6480 atcgcaaaac tatggagaag ccgtgtctct aatagataaa caatcatgca atgttttatc    6540
cttaggcggg ataactttaa ggctcagtgg ggaattcgat gtaacttatc agaagaatat    6600
ctcaatacaa gattctcaag taataataac aggcaatctt gatatctcaa ctgagcttgg    6660
gaatgtcaac aactcgatca gtaatgcttt gaataagtta gaggaaagca acagaaaact    6720
agacaaagtc aatgtcaaac tgaccagcac atctgctctc attacctata tcgttttgac    6780
```

-continued

```
tatcatatct cttgtttttg gtatacttag cctgattcta gcatgctacc taatgtacaa      6840
gcaaaaggcg caacaaaaga ccttattatg gcttgggaat aatacccctag atcagatgag     6900 agccactaca aaaatgtgaa cacagatgag gaacgaaggt ttccctaata gtaatttgtg      6960
tgaaagttct ggtagtctgt cagttcgagg agttaagaaa aaactacgcg ttgtagatga      7020
ccaaaggacg atatacgggt agaacggtaa gagaggccgc ccctcaattg cgagccaggc      7080
ttcacaacct ccgttctacc gcttcaccga caacagtcct caatcatgga ccgcgccgtt      7140
agccaagttg cgttagagaa tgatgaaaga gaggcaaaaa atacatggcg cttgatattc      7200
cggattgcaa tcttattctt aacagtagtg accttggcta tatctgtagc ctcccttta       7260 tatagcatgg gggctagcac acctagcgat cttgtaggca taccgactag gatttccagg      7320
gcagaagaaa agattacatc tacacttggt tccaatcaag atgtagtaga taggatatat      7380
aagcaagtgg cccttgagtc tccgttggca ttgttaaaaa ctgagaccac aattatgaac      7440
gcaataacat ctctctctta tcagattaat ggagctgcaa acaacagtgg gtgggggca       7500 cctatccatg acccagatta tagggggg ataggcaaag aactcattgt agatgatgct        7560
agtgatgtca catcattcta tccctctgca tttcaagaac atctgaattt tatcccggcg      7620
cctactacag gatcaggttg cactcgaata ccctcatttg acatgagtgc tacccattac      7680
tgctacaccc ataatgtaat attgtctgga tgcagagatc actcacattc atatcagtat      7740
ttagcacttg gtgtgctccg gacatctgca acagggaggg tattcttttc tactctgcgt      7800
tccatcaacc tggacgacac ccaaaatcgg aagtcttgca gtgtgagtgc aactcccctg      7860
ggttgtgata tgctgtgctc gaaagtcacg gagacagagg aagaagatta taactcagct      7920
gtccctacgc ggatggtaca tgggaggtta gggttcgacg gccagtacca cgaaaaggac      7980
ctagatgtca acacattatt cggggactgg gtggccaact acccaggagt aggggtgga      8040 tcttttattg acagccgcgt atggttctca gtctacggag ggttaaaacc caattcaccc      8100
agtgacactg tacaggaagg gaaatatgtg atatacaagc gatacaatga cacatgccca     8160
gatgagcaag actaccagat tcgaatggcc aagtcttcgt ataagcctgg acggtttggt     8220
gggaaacgca tacagcaggc tatcttatct atcaaggtgt caacatcctt aggcgaagac     8280
ccggtactga ctgtaccgcc caacacagtc acactcatgg gggccgaagg cagaattctc     8340
acagtaggga catctcattt cttgtatcaa cgagggtcat catacttctc tcccgcgtta     8400
ttatatccta tgacagtcag caacaaaaca gccactcttc atagtcctta tacattcaat     8460
gccttcactc ggccaggtag tatcccttgc caggcttcag caagatgccc caactcgtgt     8520
gttactggag tctatacaga tccatatccc ctaatcttct atagaaacca caccttgcga     8580
ggggtattcg ggacaatgct tgatggtgta caagcaagac ttaaccctgc gtctgcagta     8640
ttcgatagca catcccgcag tcgcattact cgagtgagtt caagcagtac caaagcagca     8700
tacacaacat caacttgttt taaagtggtc aagactaata agaccattg tctcagcatt     8760 gctgaaatat ctaatactct cttcggagaa ttcagaatcg tcccgttact agttgagatc     8820
ctcaaagatg acggggttag agaagccagg tctggctagt tgagtcaatt ataaaggagt     8880
tggaaagatg gcattgtatc acctatcttc tgcgacatca agaatcaaac cgaatgccgg     8940
cgcgtgctcg aattccatgt tgccagttga ccacaatcag ccagtgctca tgcgatcaga     9000
ttaagccttg tcattaatct cttgattaag aaaaaatgta agtggcaatg agatacaagg     9060
caaaatacgt accggtaaat aatacgggta ggacatggcg agctccggtc ctgaaagggc     9120
```

-continued

```
agagcatcag attatcctac cagagccaca cctgtcttca ccattggtca agcacaaact    9180
actctattac tggaaattaa ctgggctacc gcttcctgat gaatgtgact tcgaccacct    9240
cattctcagc cgacaatgga aaaaatact  tgaatcggcc tctcctgata ctgagagaat    9300
gataaaactc ggaagggcag tacaccaaac tcttaaccac aattccagaa taaccggagt    9360
gctccacccc aggtgtttag aacaactggc taatattgag gtcccagatt caaccaacaa    9420
atttcggaag attgagaaga agatccaaat tcacaacacg agatatggag aactgttcac    9480
aaggctgtgt acgcatatag agaagaaact gctggggtca tcttggtcta acaatgtccc    9540
ccggtcagag gagttcagca gcattcgtac ggatccggca ttctggtttc actcaaaatg    9600
gtccacagcc aagtttgcat ggctccatat aaaacagatc cagaggcatc tgatggtggc    9660
agctaagaca aggtctgcgg ccaacaaatt ggtgatgcta acccataagg taggccaagt    9720 cttgtcact  cctgaacttg tcgttgtgac gcatacgaat gagaacaagt tcacatgtct    9780
tacccaggaa cttgtattga tgtatgcaga tatgatggag ggcagagata tggtcaacat    9840
aatatcaacc acggcggtgc atctcagaag cttatcagag aaaattgatg acattttgcg    9900
gttaatagac gctctggcaa aagacttggg taatcaagtc tacgatgttg tatcactaat    9960
ggagggattt gcatacggag ctgtccagct actcgagccg tcaggtacat ttgcaggaga   10020
tttcttcgca ttcaacctgc aggagcttaa agacattcta attggcctcc tccccaatga   10080
tatagcagaa tccgtgactc atgcaatcgc tactgtattc tctggtttag aacagaatca   10140
agcagctgag atgttgtgtc tgttgcgtct gtggggtcac ccactgcttg agtcccgtat   10200
tgcagcaaag gcagtcagga gccaaatgtg cgcaccgaaa atggtagact ttgatatgat   10260
ccttcaggta ctgtctttct tcaagggaac aatcatcaac gggtacagaa agaagaatgc   10320
aggtgtgtgg ccgcgagtca aagtggatac aatatatggg aaggtcattg ggcaactaca   10380
tgcagattca gcagagattt cacacgatat catgttgaga gagtataaga gtttatctgc   10440
acttgaattt gagccatgta tagaatatga ccctgtcacc aacctgagca tgttcctaaa   10500
agacaaggca atcgcacacc ccaacgataa ttggcttgcc tcgtttaggc ggaaccttct   10560
ctccgaagac cagaagaaac atgtaaaaga agcaacttcg actaatcgcc tcttgataga   10620
gtttttagag tcaaatgatt ttgatccata taaagagatg gaatatctga cgacccttga   10680
gtaccttaga gatgacaatg tggcagtatc atactcgctc aaggagaagg aagtgaaagt   10740
taatggacgg atcttcgcta agctgacaaa gaagttaagg aactgtcagg tgatggcgga   10800
agggatccta gccgatcaga ttgcaccttt cttccaggga aatggagtca ttcaggatag   10860
catatccttg accaagagta tgctagcgat gagtcaactg tcttttaaca gcaataagaa   10920
acgtatcact gactgtaaag aaagagtatc ttcaaaccgc aatcatgatc cgaaaagcaa   10980
gaaccgtcgg agagttgcaa ccttcataac aactgacctg caaaagtact gtcttaattg   11040
gagatatcag acaatcaaat tgttcgctca tgccatcaat cagttgatgg gcctacctca   11100
cttcttcgaa tggattcacc taagactgat ggacactacg atgttcgtag agacccttt   11160 caatcctcca agtgacccta ctgactgtga cctctcaaga gtccctaatg atgacatata   11220
tattgtcagt gccagagggg gtatcgaagg attatgccag aagctatgga caatgatctc   11280
aattgctgca atccaacttg ctgcagctag atcgcattgt cgtgttgcct gtatggtaca   11340
gggtgataat caagtaatag cagtaacgag agaggtaaga tcagacgact ctccggagat   11400
ggtgttgaca cagttgcatc aagccagtga taatttcttc aaggaattaa ttcatgtcaa   11460
tcatttgatt ggccataatt tgaaggatcg tgaaaccatc aggtcagaca cattcttcat   11520
```

```
atacagcaaa cgaatcttca aagatggagc aatcctcagt caagtcctca aaaattcatc    11580
taaattagtg ctagtgtcag gtgatctcag tgaaaacacc gtaatgtcct gtgccaacat    11640
tgcctctact gtagcacggc tatgcgagaa cgggcttccc aaagacttct gttactattt    11700
aaactatata atgagttgtg tgcagacata ctttgactct gagttctcca tcaccaacaa    11760
ttcgcacccc gatcttaatc agtcgtggat tgaggacatc tcttttgtgc actcatatgt    11820
tctgactcct gcccaattag ggggactgag taaccttcaa tactcaaggc tctacactag    11880
aaatatcggt gacccgggga ctactgcttt tgcagagatc aagcgactag aagcagtggg    11940
attactgagt cctaacatta tgactaatat cttaactagg ccgcctggga atggagattg    12000
ggccagtctg tgcaacgacc catactcttt caattttgag actgttgcaa gcccaaatat    12060
tgttcttaag aaacatacgc aaagagtcct atttgaaact tgttcaaatc ccttattgtc    12120
tggagtgcac acagaggata atgaggcaga agagaaggca ttggctgaat tcttgcttaa    12180
tcaagaggtg attcatcccc gcgttgcgca tgccatcatg gaggcaagct ctgtaggtag    12240
gagaaagcaa attcaagggc ttgttgacac aacaaacacc gtaattaaga ttgcgcttac    12300
taggaggcca ttaggcatca agaggctgat gcggatagtc aattattcta gcatgcatgc    12360
aatgctgttt agagacgatg ttttttcctc cagtagatcc aaccacccct tagtctcttc    12420
taatatgtgt tctctgacac tggcagacta tgcacggaat agaagctggt cacctttgac    12480
gggaggcagg aaaatactgg gtgtatctaa tcctgatacg atagaactcg tagagggtga    12540
gattcttagt gtaagcggag ggtgtacaag atgtgacagc ggagatgaac aatttacttg    12600
gttccatctt ccaagcaata tagaattgac cgatgacacc agcaagaatc ctccgatgag    12660
ggtaccatat ctcgggtcaa agacacagga gaggagagct gcctcacttg caaaaatagc    12720
tcatatgtcg ccacatgtaa aggctgccct aagggcatca tccgtgttga tctgggctta    12780
tggggataat gaagtaaatt ggactgctgc tcttacgatt gcaaaatctc ggtgtaatgt    12840
aaacttagag tatcttcggt tactgtcccc tttacccacg gctgggaatc ttcaacatag    12900
actagatgat ggtataactc agatgacatt caccccctgca tctctctaca ggtgtcacct    12960
tacattcaca tatccaatga ttctcaaagg ctgttcactg aagaaggagt caaagagggg    13020
aatgtggttt accaacagag tcatgctctt gggtttatct ctaatcgaat cgatctttcc    13080
aatgacaaca accaggacat atgatgagat cacactgcac ctacatagta aatttagttg    13140
ctgtatcaga gaagcacctg ttgcggttcc tttcgagcta cttggggtgg taccggaact    13200
gaggacagtg acctcaaata gtttatgta tgatcctagc cctgtatcgg agggagactt    13260
tgcgagactt gacttagcta tcttcaagag ttatgagctt aatctggagt catatcccac    13320
gatagagcta atgaacattc tttcaatatc cagcgggaag ttgattggcc agtctgtggt    13380
ttcttatgat gaagatacct ccataaagaa tgacgccata atagtgtatg acaatacccg    13440
aaattggatc agtgaagctc agaattcaga tgtggtccgc ctatttgaat atgcagcact    13500
tgaagtgctc ctcgactgtt cttaccaact ctattacctg agagtaagag gcctagacaa    13560
tattgtctta tatatgggtg atttatacaa gaatatgcca ggaattctac ttttccaacat    13620 tgcagctaca atatctcatc ccgtcattca ttcaaggtta catgcagtgg gcctggtcaa    13680
ccatgacgga tcacaccaac ttgcagatac ggatttatc gaaatgtctg caaaactatt    13740
agtatcttgc acccgacgtg tgatctccgg cttatattca ggaaataagt atgatctgct    13800
gttcccatct gtcttagatg ataacctgaa tgagaagatg cttcagctga tatcccggtt    13860
```

```
atgctgtctg tacacggtac tctttgctac aacaagagaa atcccgaaaa taagaggctt    13920
aactgcagaa gagaaatgtt caatactcac tgagtattta ctgtcggatg ctgtgaaacc    13980
attacttagc cccgatcaag tgagctctat catgtctcct aacataatta cattcccagc    14040
taatctgtac tacatgtctc ggaagagcct caatttgatc agggaagggg aggacaggga    14100
tactatcctg gcgttgttgt tcccccaaga gccattatta gagttccctt ctgtgcaaga    14160
tattggtgct cgagtgaaag atccattcac ccgacaacct gcggcatttt tgcaagagtt    14220
agatttgagt gctccagcaa ggtatgacgc attcacactt agtcagattc atcctgaact    14280
cacatctcca aatccggagg aagactactt agtacgatac ttgttcagag ggatagggac    14340
tgcatcttcc tcttggtata aggcatctca tctcctttct gtacccgagg taagatgtgc    14400
aagacacggg aactccttat acttagctga agggagcgga gccatcatga gtcttctcga    14460
actgcatgta ccacatgaaa ctatctatta caatacgctc ttttcaaatg agatgaaccc    14520
cccgcaacga catttcgggc cgaccccaac tcagttttg aattcggttg tttataggaa    14580
tctacaggcg gaggtaacat gcaaagatgg atttgtccaa gagttccgtc cattatggag    14640
agaaaataca gaggaaagtg acctgacctc agataaagca gtggggtata ttacatctgc    14700
agtgccctac agatctgtat cattgctgca ttgtgacatt gaaattcctc cagggtccaa    14760
tcaaagctta ctagatcaac tagctatcaa tttatctctg attgccatgc attctgtaag    14820
ggagggcggg gtagtaatca tcaaagtgtt gtatgcaatg ggatactact ttcatctact    14880
catgaacttg tttgctccgt gttccacaaa aggatatatt ctctctaatg gttatgcatg    14940
tcgaggagat atggagtgtt acctggtatt tgtcatgggt tacctgggcg ggcctacatt    15000
tgtacatgag gtggtgagga tggcaaaaac tctggtgcag cggcacggta cgctcttgtc    15060
taaatcagat gagatcacac tgaccaggtt attcacctca cagcggcagc gtgtgacaga    15120
catcctatcc agtcctttac caagattaat aaagtacttg aggaagaata ttgacactgc    15180
gctgattgaa gccggggac agcccgtccg tccattctgt gcggagagtc tggtgagcac    15240
gctagcgaac ataactcaga taacccagat tatcgctagt cacattgaca cagttatccg    15300
gtctgtgata tatatggaag ctgagggtga tctcgctgac acagtatttc tatttacccc    15360
ttacaatctc tctactgacg ggaaaaagag gacatcactt atacagtgca cgagacagat    15420
cctagaggtt acaatactag gtcttagagt cgaaaatctc aataaaatag gcgatataat    15480
cagcctagtg cttaaaggca tgatctccat ggaggacctt atcccactaa ggacatactt    15540
gaagcatagt acctgcccta aatatttgaa ggctgtccta ggtattacca aactcaaaga    15600
aatgtttaca gacacttctg tattgtactt gactcgtgct caacaaaaat tctacatgaa    15660
aactataggc aatgcagtca aaggatatta cagtaactgt gactcttaac gaaaatcaca    15720
tattaatagg ctccttttt ggccaattgt attcttgttg atttaatcat attatgttag    15780
aaaaagttg aaccctgact ccttaggact cgaattcgaa ctcaaataaa tgtcttaaaa    15840
aaaggttgcg cacaattatt cttgagtgta gtctcgtcat tcaccaaatc tttgtttggt    15900
```

<210> SEQ ID NO 56
<211> LENGTH: 15882
<212> TYPE: DNA
<213> ORGANISM: Artificial Sequence
<220> FEATURE:
<223> OTHER INFORMATION: Description of Artificial Sequence: Synthetic polynucleotide
<400> SEQUENCE: 56

```
accaaacaga gaatccgtaa gttacgataa aaggcgaagg agcaattgaa gttgcacggg      60
tagaaggtgt gaatctcgag tgcgagcccg aagcacaaac tcgagaaagc cttctgccaa     120
catgtcttcc gtatttgacg agtacgaaca gctcctcgcg gctcagactc gccccaatgg    180
agctcatgga ggaggggaaa aggggagtac cttaaaagta gacgtcccgg tattcactct    240
taacagtgat gacccagaag ataggtggaa cttttgcggta ttctgcctcc ggattgctgt   300
tagcgaagat gccaacaaac cactcaggca aggtgctctc atatctcttt tatgctccca    360
ctcacaagtg atgaggaacc atgttgccct tgcagggaaa cagaatgaag ccacattggc    420
cgtgcttgag attgatggct ttgccaacgg tatgccccag ttcaacaata ggagtggagt    480
gtctgaagag agagcacaga gattcgcgat gatagcaggg tctctccctc gggcatgcag    540
taatggcacc ccgttcgtca cagccggggc cgaagatgat gcaccagaag atatcaccga    600
taccctggag aggatcctct ctatccaggc ccaagtatgg gtcacagtag caaaagccat    660
gactgcgtat gagactgcag atgagtctga aacaagacga atcagtaagt atatgcagca    720
aggcagggtc caaaagaaat acatcctcta ccccgtatgc aggagcacaa tccaactcac    780
gatcagacag tctcttgcag tccgcatctt tttggttagc gagctcaaga gaggccgcaa    840
cacggcaggt ggtacctcta cttattataa cctagtaggg gacgtagact catatatcag    900
gaataccggg cttactgcat tcttcttgac actcaagtac ggaattaaca ccaagacatc    960
agcccttgca cttagtagcc tctcaggcga catccagaaa atgaagcagc tcatgcgttt   1020
atatcggatg aaaggagata atgcgccgta catgacattg cttggtgata gtgaccagat   1080
gagctttgcg cctgccgagt atgcacaact ttactccttc gccatgggta tggcatcagt   1140
cctagataaa ggtactggga ataccaatt tgccagggac tttatgagca catcattctg    1200
gagacttgga gtagagtacg ctcaggctca gggaagtagc attaacgagg atatggctgc   1260
cgagctaaag ttaaccccag cagcaaggag aggcctggca gctgctgccc aacgagtctc   1320
tgaggagacc agcagcatag acatgcctac tcaacaagtc ggagtcctca ctgggctcag   1380
cgagggggggg tcccaagccc tacaaggcgg atcgaataga tcgcaagggc aaccagaagc   1440
cggggatggg gagacccaat tcctggatct gatgagagcg gtagcaaata gcatgaggga   1500
agcgccaaac tctgcacagg gcactcccca atcggggcct cccccaactc ctgggccatc    1560
tcaagataac gacaccgact gggggtattg attgacaaaa cccagcttgc ttccacaaaa   1620
tcatcccaat atcctcaccc gtagtcgacc cctcgatttg cggccctata tgaccacacc    1680
cacaaacaaa catcccccctc tttcctcccct cccctgctg tacaactccg cacgccctag    1740
gtaccacagg cacaatgcgg ctcactaaca atcaaaacag agccgaggaa attagaaaaa   1800
aatacgggta gaagagggat attcagagac caggcaagt cacccgagtc tctgctctct    1860
cctctacctg atagattagg acaaatatgg ccaccttta c agatgcggag atcgacgagc   1920
tatttgagac aagtggaact gtgattgaca acataattac agcccagggt aaatcagcag   1980
agactgttgg aaggagtgca atcccacatg gcaaaaccaa ggcgctgagc gcagcatggg   2040
agaagcatgg gagcatccag ccaccggcca gtcaagacac ccctgatcga caggacagat   2100
ctgacaaaca accatccaca cccgagcaag cgaccccgca tgcagcccg ccggccacat    2160
ccgccgacca gcccccacc caggccacag acgaagccgt cgacacacag ctcaggaccg    2220
gagcaagcaa ctctctgctg ttgatgcttg acaagctcag caataaatcg tccaatgcta   2280
aaaagggcct atggtcgagc ccccaagagg ggaaccacca acgtccgact caacagcagg   2340
gaagtcaacc cagccgcgga aacagccagg aaagaccgca gaaccaagtc aaggccgccc    2400
```

```
ctggaaacca gggcacagac gcgaacacag catatcatgg acaatgggag gagtcacaac    2460
tatcagctgg tgcaacccct catgctctcc gatcaaggca gagccaagac aatacccttg    2520
tatctgcgga tcatgtccag ccacctgtag actttgtgca agcgatgatg tctatgatgg    2580
aggcaatatc acagagagta agtaaggttg actatcagct agatcttgtc ttgaaacaga    2640
catcctccat ccctatgatg cggtccgaaa tccaacagct gaaaacatct gttgcagtca    2700
tggaagccaa tttgggaatg atgaagattc tggatcccgg ttgtgccaac gtttcatctc    2760
tgagtgatct acgggcagtt gcccgatctc acccggtttt agtttcaggc cctggagacc    2820
catctcccta tgtgactcaa ggaggcgaaa tggcacttaa taaactttcg caaccagtgc    2880
cacatccatc tgaattgatt aaatccgcca ctgcatgcgg gcctgatata ggagtggaaa    2940
aggacactgt ccgtgcattg atcatgtcac gcccaatgca cccgagttct tcagccaagc    3000
tcctaagcaa gctagatgca gccgggtcga tcgaggaaat caggaaaatc aagcgccttg    3060
cactaaatgg ctaattacta ctgccacacg tagcgggtcc ccgtccactc ggcatcacac    3120
ggaatctgca ccgagtcccc ccccgcagac ctaaggtcca actctccaag tggcaatcct    3180
ctctcgcttc ctcagcccca ctgaatgatc gcgcaaccgt aattaatcta gctacattaa    3240
ggattaagaa aaaatacggg tagaattgga gtgccccaat tgtgccaaga tggactcatc    3300
taggacaatt gggctgtact ttgattctgc ccattcttct agcaacctgt tagcatttcc    3360
gatcgtccta caagacacag gagatgggaa gaagcaaatc gccccgcaat ataggatcca    3420
gcgcctagac tcgtggactg atagtaaaga agactcagta ttcatcacca cctatggatt    3480
catctttcag gttgggaatg aagaagccac tgtcggcatg atcaatgata atcccaagcg    3540
cgagttactt tctgctgcga tgctctgcct aggaagcgtc ccaaataccg agaccttgt    3600
tgagctggca agggcctgtc tcactatggt agtcacatgc aagaagagtg caactaatac    3660
tgagagaatg gttttctcag tagtgcaggc accccaagtg ctgcaaagct gtagggttgt    3720
ggcaaacaaa tactcatcag tgaatgcagt caagcacgtg aaagcgccag agaagatccc    3780
cgggagtgga accctagaat acaaggtgaa cttgtctcc ttgactgtgg taccgaagaa    3840
ggatgtctac aagatcccaa ctgcagtatt gaaggtttct ggctcgagtc tgtacaatct    3900
tgcgctcaat gtcactatta atgtggaggt agactcgagg agtcctttgg ttaaatctct    3960
gtctaagtct gacagcggat actatgctaa cctcttcttg catattggac ttatgaccac    4020
cgtagatagg aggggaaga aagtgacttt tgacaagcta gaaaagaaga taaggagcct    4080
tgatctatct gtcgggctca gtgatgtgct cggaccttcc gtgctggtaa agcaagagg    4140
tgcacggacc aagcttttgg caccttcct ctctagcagt gggacagcct gctatcccat    4200
agcaaatgcc tctcctcagg tggccaagat actctggagt caaaccgcgt gcctgcggag    4260
cgttaaaatc attatccaag caggtaccca acgcaccgtc gcagtgaccg ctgaccacga    4320
ggttacctct actaagctgg agaaggggca caccttgcc aaatacaatc cttttaagaa    4380
ataagctgcg tctctgagat tgcgctccgc ccactcaccc agagcatcat gacaccaaaa    4440
actaatctgt cttgattatt tacagttagt ttacctgtct atcaaattag aaaaaacacg    4500
ggtagaagat tctggatccc ggttggcgcc ttctaggtgc aagatgggcc ccagaccttc    4560
taccaagaac ccagtaccta tgatgctgac tgtccgagtc gcgctggtac tgagttgcat    4620
ctgtccggca aactccattg atggcaggcc tcttgcggct gcaggaattg tggtaacagg    4680
agacaaagca gtcaacatat acacctcatc ccagacagga tcaatcatag ttaagctcct    4740
```

```
cccaaacctg cccaaggata aggaggcatg tgcgaaagcc cccttggatg catacaacag    4800
gacattgacc actttgctca cccccttgg tgactctatc cgtaggatac aagagtctgt     4860
aactacatct ggagggagga gacagaaacg ctttataggc gccattattg gcggtgtggc    4920
tcttggggtt gcaactgctg cacaaataac agcggccgca gctctgatac aagccaaaca    4980
aaatgctgcc aacatcctcc gacttaaaga gagcattgcc gcaaccaatg aggccgtgca    5040
tgaggtcact gacggattat cgcaactagc agtggcagtt gggaagatgc agcagtttgt    5100
taatgaccaa tttaataaaa cagctcagga attaggctgc atcagaattg cacagcaagt    5160
tggtgtagag ctcaacctgt acctaaccga attgactaca gtattcggac cacaaatcac    5220
ttcacctgcc ttaaacaagc tgactattca ggcactttac aatctagctg gtgggaatat    5280
ggattacttg ttgactaagt taggtgtagg gaacaatcaa ctcagctcat taatcggtag    5340
cggcttaatc accggcaacc ctattctgta cgactcacag actcaactct tgggtataca    5400
ggtaactcta ccttcagtcg ggaacctaaa taatatgcgt gccacctact tggaaacctt    5460
atccgtaagc acaaccaggg gatttgcctc ggcacttgtc ccaaaagtgg tgacacaggt    5520
cggttctgtg atagaagaac ttgacacctc atattgtata gaaaccgact tggatttata    5580
ttgtacaaga atagtaacat tccctatgtc ccctggtatt tattcctgct tgagcggcaa    5640
tacatcggcc tgtatgtact caaagaccga aggcgcactc actacgccat acatgactat    5700
caaaggctca gtcatcgcta actgcaagat gacaacatgt agatgtgtaa acccccggg    5760 tatcatatcg caaaactatg gagaagccgt gtctctaata gataagcaat catgcaatgt    5820
tttatcctta gacgggataa ctttaaggct cagtggggaa ttcgatgcaa cttatcagaa    5880
gaatatctca atacaagatt ctcaagtaat aataacaggc aatcttgata tctcaactga    5940
gcttgggaat gtcaacaact cgatcagtaa tgctttgaat aagttagagg aaagcaacag    6000
caaactagac aaagtcaatg tcaaactgac cagcacatct gctctcatta cctatatcgt    6060
tttgactatc atatctcttg tttttggtat acttagcctg gttctagcat gctacctaat    6120
gtataagcaa aaggcgcaac aaaagacctt attatggctt gggaataata ccctagatca    6180
gatgagagcc actacaaaaa tgtgaacaca gatgaggaac gaaggtatcc ctaatagtaa    6240
tttgtgtgaa agttctggta gtctgtcaat tcggagagtt tagaaaaaac tacgcgttgt    6300
agatgaccaa aggacgatat acgggtagaa cggtaagaga ggccgcccct caattgcgag    6360
ccgggcttca caacctccgt tctaccgctt caccgacagc agtcctcagt catggaccgc    6420
gcagttagcc aagttgcgtt agagaatgat gaaagagagg caaaaaatac atggcgcttg    6480
atattccgga ttgcaatctt actcttaaca gtagtgacct tagctacatc tgtagcctcc    6540
cttgtatata gcatggggc tagcacacct agcgaccttg taggcatacc gaccaggatt     6600
tctagggcag aagaaaagat tacatctgca cttggttcca atcaagatgt agtagatagg    6660
atatataagc aagtggccct tgagtctccg ttggcattgt taaacactga gaccacaatt    6720
atgaacgcaa taacatctct ctcttatcag attaatggag ctgcgaacaa cagcgggtgg    6780
ggggcaccta tccatgaccc agattttatc gggggatag gcaaagaact cattgtagat     6840
gatgctagta tgtcacatc attctatccc tctgcatttc aagaacatct gaattttatc     6900
ccggcgccta ctacaggatc aggttgcact cggataccgt catttgacat gagtgctacc    6960
cattactgct acactcataa tgtaatattg tctggatgca gagatcactc acactcacat    7020
cagtatttag cacttggtgt gctccggaca actgcaacag ggaggatatt cttttctact    7080
ctgcgttcca tcagtctgga tgacacccaa aatcggaagt cttgcagtgt gagtgcaact    7140
```

```
cccttaggtt gtgatatgct gtgctcgaaa gtcacggaga cagaggaaga agattataac    7200
tcagctgtcc ctacgctgat ggcacatggg aggttagggt tcgacggcca ataccacgaa    7260
aaggacctag acgtcacaac attatttgag gactgggtgg ccaactaccc aggagtaggg    7320
ggtggatctt ttattgacgg ccgcgtatgg ttctcagtct acggagggct gaaacccaat    7380
tcacccagtg acactgtaca ggaagggaaa tatgtaatat acaagcgata caatgacaca    7440
tgcccagatg agcaagacta ccagatccga atggccaagt cttcgtataa gcccgggcgg    7500
tttggtggga aacgcataca gcaggctatc ttatctatca aggtgtcaac atctttgggc    7560
gaagacccag tactgactgt accgcccaac acagtcacac tcatggggc cgaaggcaga    7620 attctcacag tagggacatc tcatttcttg tatcagcgag ggtcatcata cttctctccc    7680
gcgttattat atcctatgac agtcagcaac aaaacagcca ctcttcatag tccctataca    7740
ttcaatgcct tcactcggcc aggtagtatc ccttgccagg cttcagcaag atgccccaac    7800
tcgtgtgtta ctggagtcta tacagatcca tatcccctaa tcttctatag gaaccacacc    7860
ttgcgagggg tattcgggac aatgcttgat agtgaacaag caagacttaa tcctgcgtct    7920
gcagtattcg atagcacatc ccgcagtcgc ataactcgag tgagttcaag cagcaccaaa    7980
gcagcataca caacatcaac ttgttttaaa gttgtcaaga ccaataagac ctattgtctc    8040
agcattgctg aaatatctaa tactctcttc ggagaattca gaatcgtccc gttactagtt    8100
gagatcctca aaaatgatgg ggttagagaa gccaggtctg gttagttgag tcaactatga    8160
aagagctggg aagatggcat tgtatcacct atcttccgcg acaccaagaa tcaaactgaa    8220
tgccggtgcg agctcgaatt ccatgtcgcc agttgaccac aatcagccag tgctcatgcg    8280
atcagatcaa gtcttgtcaa tagtccctcg attaagaaaa aatgtaagtg gcaatgagat    8340
acaaggcaaa acagctaccg gtacgggtag aacgccacca tggagaaaaa aatcactgga    8400
tataccaccg ttgatatatc ccaatggcat cgtaaagaac attttgaggc atttcagtca    8460
gttgctcaat gtacctataa ccagaccgtt cagctggata ttacggcctt tttaaagacc    8520
gtaaagaaaa ataagcacaa gttttatccg gcctttattc acattcttgc ccgcctgatg    8580
aatgctcatc cggaattccg tatggcaatg aaagacggtg agctggtgat atgggatagt    8640
gttcacccct tgttacaccg ttttccatgag caaactgaaa cgttttcatc gctctggagt    8700
gaataccacg acgatttccg gcagtttcta cacatatatt cgcaagatgt ggcgtgttac    8760
ggtgaaaacc tggcctattt ccctaaaggg tttattgaga atatgttttt cgtctcagcc    8820
aatccctggg tgagtttcac cagttttgat ttaaacgtgg ccaatatgga aacttcttc    8880 gcccccgttt tcaccatggg caaatactat acgcaaggcg acaaggtgct gatgccgctg    8940
gcgattcagt tcatcatgc cgtttgtgat ggcttccatg tcggcagaat gcttaatgaa    9000
ttacaacagt actgcgatga gtggcagggc ggggcgtaat gattagaaaa aaaccggtaa    9060
atagtacggg taggacatgg cgagctccgg tcctgaaagg gcagagcatc agattatcct    9120
accagagtca cacctgtctt caccattggt caagcacaaa ctactttatt actggaaatt    9180
aactgggcta ccgcttcctg atgaatgtga cttcgaccac ctcattctca gcagacaatg    9240 gaaaaaata cttgaatcgg cctctcctga tactgagaga atgataaaac tcggaagggc    9300
agtacaccaa actctcaacc acaattctag aataaccgga gtactccacc ccaggtgttt    9360
agaagaactg gctagtattg aggtccctga ttcaaccaac aaatttcgga agattgagaa    9420
gaagatccaa attcacaaca cgagatatgg agaactgttc acaaggctgt gtacgcatat    9480
```

```
agagaagaaa ctgctggggt catcctggtc taacaatgtc ccccggtcag aggagttcaa    9540
cagcatccgt acggatccgg cattctggtt tcactcaaaa tggtccacag ccaagtttgc    9600
atggctccat ataaaacaga tccagaggca tctgattgtg gcagctagga caaggtctgc    9660
ggccaacaaa ttggtgatgc taacccataa ggtaggccaa gtctttgtca ctcctgaact    9720
tgtcattgtg acgcatacga atgagaacaa gttcacatgt cttacccagg aacttgtatt    9780
gatgtatgca gatatgatgg agggcagaga tatggtcaac ataatatcaa ccacggcggt    9840
gcatctcaga agcttatcag agaaaattga tgacattttg cagttaatag acgctctggc    9900
aaaagacttg ggcaatcaag tctacgatgt tgtatcacta atggagggat ttgcatacgg    9960
agctgtccag ctgctcgagc cgtcaggtag atttgcagga catttcttcg cattcaacct   10020
gcaggagctt aaagacattc taatcggcct cctccccaat gatatagcag aatccgtgac   10080
tcatgcaata gctactgtat tctctggttt agaacagaat caagcagctg atgttgtg    10140
cctgttgcgt ctgtgggtc acccactgct gagtcccgt attgcagcaa aggcagtcag    10200
gagccaaatg tgcgcaccga aaatggtgga ctttgatatg atccttcagg tactgtcttt   10260
cttcaaggga acaatcatca acggatacag aaagaagaat gcaggtgtgt ggccgcgagt   10320
caaagtggat acaatatatg ggaagatcat tgggcaacta catgcagatt cagcagagat   10380
ttcacacgat atcatgttga gagagtataa gagtttatct gcacttgaat ttgagccatg   10440
tatagaatac gaccctgtca ctaacctgag catgttccta aaagacaagg caatcgcaca   10500
ccctaacgat aattggcttg cctcgtttag gcggaacctt ctctccgaag accagaagaa   10560
acatgtaaaa gaagcaactt cgactaatcg cctcttgata gagtttttag agtcaaatga   10620
ttttgatcca tataagagaa tggaatatct gacgacccct gagtaccta gagatgacga    10680
tgtggcagta tcatactcgc tcaaagagaa ggaagtgaaa gttaatggac ggatcttcgc   10740
taagctgaca aagaagttaa ggaactgtca ggtgatggcg aagggatcc tagccgacca    10800
gattgcacct ttctttcagg gaatggagt cattcaggat agcatatcgt tgaccaagag    10860
tatgctagcg atgagtcaac tgtctttta cagcaataag aaacgtatca ctgactgtaa    10920
agaaagagta tcttcaaacc gcaatcatga tccgaagagc aagaaccgtc ggagagttgc   10980
aaccttcata caaactgacc tgcaaaagta ctgtcttaat tggagatatc agacaatcaa   11040
actgttcgct catgccatca atcagttgat gggcctacct cacttctttg agtggattca   11100
cctaagactg atggacacta caatgttcgt aggagaccct ttcaatcctc caagtgaccc   11160
tactgactgt gacctctcaa gagtccctaa tgatgacata tatattgtca gtgccagagg   11220
gggtatcgaa ggattatgtc agaagctatg gacaatgatc tctattgctg caatccaact   11280
tgctgcagct agatcgcatt gtcgcgttgc ctgtatggta cagggtgata atcaagtaat   11340
agcagtaacg agagaggtaa gatcagacga ctctccggag atggtgttga cacagttgca   11400
tcaagccagt gataatttct tcaaggaatt aattcatgtc aatcatttga ttggccataa   11460
tttgaaggac cgtgaaacca tcaggtcaga cacattcttc atatacagca aacgaatctt   11520
caaagatgga gcaatcctca gtcaagtcct caaaaattca tctaaattag tactggtgtc   11580
aggtgatctc agtgaaaaca ccgtaatgtc ctgtgccaac attgcctcta ctgtagcacg   11640
gctatgcgag aacgggcttc ccaaggactt ctgttactat ttaaactata atgagttg    11700
cgtgcagaca tactttgact ctgagttctc ctacaacaac aattcgcacc ccgatcttaa   11760
ccagtcgtgg attgaggaca tctcttttgt gcactcatat gttctgactc ctgcccaatt   11820
aggggggactt agtaaccttc aatactcaag gctctacact agaaatatcg gtgacccggg   11880
```

```
gactactgct tttgcagaga tcaagcgact agaagcagtg ggattactga gtcctaacat    11940
tatgactaat atcttaacta ggccgcctgg gaatggagat tgggccagtc tttgcaacga    12000
cccatactct ttcaattttg agactgttgc aagcccaaac attgttctta agaaacatac    12060
gcaaagagtc ctatttgaaa cttgttcaaa tcccttattg tctggagtgc acacagagga    12120
taatgaggca gaagagaagg cattggctga attcttgctt aatcaagagg tgattcatcc    12180
ccgcgttgcg catgctatca tggaggcaag ctctgtaggt aggagaaagc aaattcaagg    12240
gcttgttgac acaacaaaca ccgtaattaa gattgcactt actaggaggc cactaggcat    12300
caagaggctg atgcggatag tcaattattc tagcatgcat gcaatgctgt ttagagacga    12360
tgttttttcc tccaatagat ccaaccaccc cttagtctct tctaatatgt gttctctgac    12420
actggcagac tatgcacgga atagaagctg gtcacctttg acgggaggca ggaaaatact    12480
gggtgtatct aatcctgata cgatagaact cgtagagggt gagattctta gtgtaagcgg    12540
agggtgcaca agatgcgaca gcggagatga acagtttact tggttccatc ttccaagcaa    12600
tatagaattg accgatgaca ccagcaagaa tcctccgatg agagtaccat atctcgggtc    12660
aaagacacag gagaggagag ctgcctcact tgcgaaaata gctcatatgt cgccacatgt    12720
gaaggctgcc ctaagggcat catccgtgtt gatctgggct tatggggata atgaagtaaa    12780
ttggactgct gctcttacga ttgcaaaatc tcgatgtaat ataaacttag agtatcttcg    12840
gttattgtcc cctttaccca cggctgggaa tcttcaacat agactagatg atggtataac    12900
tcagatgaca ttcacccctg catctctcta cagggtgtca ccttacattc acatatccaa    12960
tgattctcaa aggctattca ctgaagaagg agtcaaagag gggaatgtgg tttatcaaca    13020
gatcatgctc ttgggtttat ctctaatcga atcgatcttt ccaatgacga caaccaggac    13080
atatgatgag atcacattgc atctacatag taaatttagt tgctgtatca gggaagcacc    13140
tgttgcggtt cctttcgagc tacttggggt ggcaccggag ctaaggacag tgacctcaaa    13200
caagtttatg tatgatccta gccctgtatc ggagggagac tttgcgagac ttgacttagc    13260
tatcttcaag agttatgagc ttaatctgga gtcatatccc acgatagagc taatgaacat    13320
tctttcaata tccagcggga agttgattgg ccagtctgtg gtttcttatg atgaagatac    13380
ctccataaag aatgacgcca taatagtgta tgacaatacc cgaaattgga tcagtgaagc    13440
tcagaattca gatgtggtcc gcttatttga atatgcagca cttgaagtgc tcctcgactg    13500
ttcttaccaa ctctattatc tgagagtaag aggcctagac aatattgtct tatatatggg    13560
tgatttatac aagaatatgc caggaattct actttccaac attgcagcta caatatctca    13620
tcccgtcatt cattcaaggt tacatgcagt gggcctggtc aaccataacg gatcacacca    13680
acttgcagat acgattttta tcgaaatgtc tgcaaaactg ttagtatctt gcactcgacg    13740
tgtgatctcc ggcttatatt cagggaataa gtatgatctg ctgttcccat ctgtcttaga    13800
tgataacctg aatgagaaga tgcttcagct gatatcccgg ttatgctgtc tgtacacggt    13860
actctttgct acaacaagag aaatcccgaa aataagaggc ttatctgcag aagagaaatg    13920
ttcagtactt actgagtatc tactgtcgga tgctgtgaaa ccattactta gccctgatca    13980
ggtgagctct atcatgtctc taacataat tacattccca gctaatctgt actacatgtc    14040
tcggaagagc ctcaatttga tcagggaaag ggaggacaag gattctatcc tggcgttgtt    14100
gttcccccaa gagccattat tagagttccc ttctgtgcaa gatattggtg ctcgagtgaa    14160
agatccattc acccgacaac ctgcggcatt tttgcaagag ttagatttga gtgctccagc    14220
```

```
aaggtatgac gcattcacac ttagtcagat tcatcctgag ctcacatcac caaatccgga    14280
ggaagactac ttagtacgat acttgttcag aggaataggg actgcatcct cctcttggta    14340
taaggcatcc catctccttt ctgtacccga ggtaagatgt gcaagacacg ggaactcctt    14400
atacttagct gaaggaagcg gagccatcat gagtcttctc gaactgcatg taccacatga    14460
aactatctat tacaatacgc tcttttcaaa tgagatgaac cccccgcagc gacatttcgg    14520
gccgacccca acccagtttt tgaattcggt tgtttatagg aacctacagg cggaggtaac    14580
atgcaaggat ggatttgtcc aagagttccg tccactatgg agagaaaata cagaggaaag    14640
cgacctgacc tcagataaag cagtgggta tattacatct gcagtgccct acagatctgt    14700
atcattgctg cattgtgaca ttgaaatccc tccagggtcc aatcaaagct tactagatca    14760
attagctatc aatttatctc tgattgccat gcattccgta agggagggcg gggtagtgat    14820
catcaaagtg ttgtatgcaa tgggatacta ctttcatcta ctcatgaact tgttcgctcc    14880
gtgttccaca aaaggataca ttctctctaa tggttatgca tgtagagggg atatggagtg    14940
ttacctggta tttgtcatgg gttacctggg cgggcctaca tttgtacacg aggtggtgag    15000
gatggcaaaa actctggtgc agcggcacgg tacgcttttg tccaaatcag atgagatcac    15060
actgaccagg ttattcacct cacagcggca gcgtgtgaca gacatcctat ccagtccttt    15120
accaagatta ataaagtact tgagaaagaa tattgacact gcgctgattg aagctggggg    15180
acagcccgtc cgtccattct gtgcagagag tttggtgagc acgctggcgg ataactca     15240 gataacccag atcattgcta gtcacattga cacagtcatc cggtctgtga tatatatgga    15300
agctgagggt gatctcgctg acacagtatt tctatttacc ccttacaatc tctctactga    15360
cgggaaaaag agaacatcac ttaaacagtg cacgagacag atcctagagg ttacaatatt    15420
gggtcttaga gtcgaagatc tcaataaaat aggcgatgta atcagcctag tgcttaaagg    15480
catgatctcc atggaggacc ttatcccact aaggacatac ttgaagcata gtacctgccc    15540
taaatatttg aaggctgtcc taggtattac caaactcaaa gaaatgttta cagacaccctc   15600 tgtattgtac ttgactcgtg ctcaacaaaa attctacatg aaaactatag gcaatgcagt    15660
caaaggatat tacagtaact gtgactctta acgaaaatca catattaata ggctccttt    15720 ctggccaatt gtatccttgg tgatttaatt atactatgtt agaaaaaaat tgaactccga    15780
ctccttagat ctcgaattcg aactcaaata aatgtcttaa aaaaaggttg cgcacaatta    15840
ttcttgagtg tagtcttgtt attcaccaaa tctttgtttg gt                       15882
```

<210> SEQ ID NO 57
<211> LENGTH: 3658
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57

```
ttgacgtcta aattaaccgg tggatccgtc gacccgggac gcgtctgcag caatggcaac      60
aacgttgcgc aaactattaa ctggcgaact acttactcta gcttcccggc aacaattaat     120
agactggatg gaggcggata agttgcagg accacttctg cgctcggccc ttccggctgg     180
ctggtttatt gctgataaat ctggagccgg tgagcgtggg tctcgcggta tcattgcagc     240
actggggcca gatggtaagc cctcccgtat cgtagttatc tacacgacgg ggagtcaggc     300
aactatggat gaacgaaata gacagatcgc tgagataggt gcctcactga ttaagcattg    360
```

```
gtaactgtca gaccaagttt actcatatat actttagatt gatttaaaac ttcattttta      420
atttaaaagg atctaggtga agatccttt tgataatctc atgaccaaaa tcccttaacg       480
tgagttttcg ttccactgag cgtcagaccc cgtagaaaag atcaaaggat cttcttgaga      540
tccttttttt ctgcgcgtaa tctgctgctt gcaaacaaaa aaaccaccgc taccagcggt      600
ggtttgtttg ccggatcaag agctaccaac tcttttccg aaggtaactg gcttcagcag       660
agcgcagata ccaaatactg tccttctagt gtagccgtag ttaggccacc acttcaagaa      720
ctctgtagca ccgcctacat acctcgctct gctaatcctg ttaccagtgg ctgctgccag      780
tggcgataag tcgtgtctta ccgggttgga ctcaagacga tagttaccgg ataaggcgca      840
gcggtcgggc tgaacggggg gttcgtgcac acagcccagc ttggagcgaa cgacctacac      900
cgaactgaga tacctacagc gtgagctatg agaaagcgcc acgcttcccg aagggagaaa      960
ggcggacagg tatccggtaa gcggcagggt cggaacagga gagcgcacga gggagcttcc     1020
agggggaaac gcctggtatc tttatagtcc tgtcgggttt cgccacctct gacttgagcg     1080
tcgatttttg tgatgctcgt cagggggcg gagcctatgg aaaaacgcca gcaacgcggc      1140 cttttacgg ttcctggcct tttgctggcc ttttgctcac atgttctttc ctgcgttatc       1200
ccctgattct gtggataacc gtattaccgc ctttgagtga gctgataccg ctcgccgcag     1260
ccgaacgacc gagcgcagcg agtcagtgag cgaggaagcg gaagagcgcc tgatgcggta     1320
ttttctcctt acgcatctgt gcggtatttc acaccgcata tggtgcactc tcagtacaat     1380
ctgctctgat gccgcatagt taagccagta tacactccgc tatcgctacg tgactgggtc     1440
atggctgcgc cccgacaccc gccaacaccc gctgacgcgc cctgacgggc ttgtctgctc     1500
ccggcatccg cttacagaca agctgtgacc gtctccggga gctgcatgtg tcagaggttt     1560
tcaccgtcat caccgaaacg cgcgaggcag ctgcggtaaa gctcatcagc gtggtcgtga     1620
agcgattcac agatgtctgc ctgttcatcc gcgtccagct cgttgagttt ctccagaagc     1680
gttaatgtct ggcttctgat aaagcgggcc atgttaaggg cggttttttc ctgtttggtc     1740
acttgatgcc tccgtgtaag ggggaatttc tgttcatggg ggtaatgata ccgatgaaac     1800
gagagaggat gctcacgata cgggttactg atgatgaaca tgcccggtta ctggaacgtt     1860
gtgagggtaa acaactggcg gtatggatgc ggcgggacca gagaaaaatc actcagggtc     1920
aatgccagcg cttcgttaat acagatgtag gtgttccaca gggtagccag cagcatcctg     1980
cgatgcagat ccggaacata tggtgcagg cgctgactt ccgcgtttcc agactttacg       2040
aaacacggaa accgaagacc attcatgttg ttgctcaggt cgcagacgtt ttgcagcagc     2100
agtcgcttca cgttcgctcg cgtatcggtg attcattctg ctaaccagta aggcaacccc     2160
gccagcctag ccgggtcctc aacgacagga gcacgatcat cgcacccgt ggccaggacc      2220 caacgctgcc cgagatgcgc cgcgtgcggc tgctggagat ggcggacgcg atggatatgt     2280
tctgccaagg gttggtttgc gcattcacag ttctccgcaa gaattgattg gctccaattc     2340
ttggagtggt gaatccgtta gcgaggtgcc gccggcttcc attcaggtcg aggtggcccg     2400
gctccatgca ccgcgacgca acgcggggag gcagacaagg tatagggcgg cgcctacaat     2460
ccatgccaac ccgttccatg tgctcgccga ggcggcataa atcgccgtga cgatcagcgg     2520
tccagtgatc gaagttaggc tggtaagagc cgcgagcgat ccttgaagct gtccctgatg     2580
gtcgtcatct acctgcctgg acagcatggc ctgcaacgcg gcatcccga tgccgccgga      2640 agcgagaaga atcataatgg ggaaggccat ccagcctcgc gtcgcgaacg ccagcaagac     2700
gtagcccagc gcgtcggccg ccatgccggc gataatggcc tgcttctcgc cgaaacgttt     2760
```

```
ggtggcggga ccagtgacga aggcttgagc gagggcgtgc aagattccga ataccgcaag    2820
cgacaggccg atcatcgtcg cgctccagcg aaagcggtcc tcgccgaaaa tgacccagag    2880
cgctgccggc acctgtccta cgagttgcat gataaagaag acagtcataa gtgcggcgac    2940
gatagtcatg ccccgcgccc accggaagga gctgactggg ttgaaggctc tcaagggcat    3000
cggtcgacgc tctcccttat gcgactcctg cattaggaag cagcccagta gtaggttgag    3060
gccgttgagc accgccgccg caaggaatgg tgcatgcaag gagatggcgc caacagtcc     3120 cccggccacg gggcctgcca ccatacccac gccgaaacaa gcgctcatga gcccgaagtg    3180
gcgagcccga tcttccccat cggtgatgtc ggcgatatag gcgccagcaa ccgcacctgt    3240
ggcgccggtg atgccggcca cgatgcgtcc ggcgtagaag atccacagga cgggtgtggt    3300
cgccatgatc gcgtagtcga tagtggctcc aagtagcgaa gcgagcagga ctgggcggcg    3360
gccaaagcgg tcggacagtg ctccgagaac gggtgcgcat agaaattgca tcaacgcata    3420
tagcgctagc agcacgccat agtgactggc gatgctgtcg gaatgacga tatcccgcaa     3480 gaggcccggc agtaccggca taaccaagcc tatgcctaca gcatccaggg tgacggtgcc    3540
gaggatgacg atgagcgcat tgttagattt catacacggt gcctgactgc gttagcaatt    3600
taactgtgat aaactaccgc attaaagctt atcgatgata agctgtcaaa catgagaa      3658
```

<210> SEQ ID NO 58
<211> LENGTH: 19563
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 58

```
ttggcgcgcc taatacgact cactatagga ccaaacagag aatccgtaag ttacgataaa      60
aggcgaagga gcaattgaag ttgcacgggt agaaggtgtg aatctcgagt gcagcccga     120 agcacaaact cgagaaagcc ttctgccaac atgtcttccg tatttgacga gtacgaacag    180
ctcctcgcgg ctcagactcg ccccaatgga gctcatggag gaggggaaaa ggggagtacc    240
ttaaaagtag acgtcccggt attcactctt aacagtgatg acccagaaga taggtggaac    300
tttgcggtat tctgcctccg gattgctgtt agcgaagatg ccaacaaacc actcaggcaa    360
ggtgctctca tatctctttt atgctcccac tcacaagtga tgaggaacca tgttgccctt    420
gcagggaaac agaatgaagc cacattggcc gtgcttgaga ttgatggctt tgccaacggt    480
atgccccagt tcaacaatag gagtggagtg tctgaagaga gagcacagag attcgcgatg    540
atagcagggt ctctcccctcg ggcatgcagt aatggcaccc cgttcgtcac agccggggcc    600
gaagatgatg caccagaaga tatcaccgat accctggaga ggatcctctc tatccaggcc    660
caagtatggg tcacagtagc aaaagccatg actgcgtatg agactgcaga tgagtcagaa    720
acaagacgaa tcaataagta tatgcagcaa ggcagggtcc aaaagaaata catcctctac    780
cccgtatgca ggagcacaat ccaactcacg atcagacagt ctcttgcagt ccgcatcttt    840
ttggttagcg agctcaagag aggccgcaac acggcaggtg gtacctctac ttattataac    900
ctagtagggg acgtagactc atatatcagg aataccgggc ttactgcatt cttcttgaca    960
ctcaagtacg gaatcaacac caagacatca gcccttgcac ttagtagcct ctcaggcgac    1020
atccagaaga tgaagcagct catgcgtttg tatcggatga aggagataa tgcgccgtac     1080 atgacattgc ttggtgatag tgaccagatg agctttgcgc ctgccgagta tgcacaactt    1140
```

```
tactccttcg ccatgggtat ggcatcagtc ctagataaag gtactgggaa ataccaattt    1200
gccagggact ttatgagcac atcattctgg agacttggag tagagtacgc tcaggctcag    1260
ggaagtagca ttaacgagga tatggctgcc gagctaaagc taaccccagc agcaaggaga    1320
ggcctggcag ctgctgccca acgagtctcc gaggagacca gcagcataga catgcctact    1380
caacaagtcg gagtcctcac tgggctcagc gagggggggt cccaagccct acaaggcgga    1440
tcgaatagat cgcaagggca accagaagcc ggggatgggg agacccaatt cctggatctg    1500
atgagagcgg tagcaaatag catgagggaa gcgccaaact ctgcacaggg cactccccaa    1560
tcggggcctc ccccaactcc tgggccatcc caagataacg acaccgactg ggggtattga    1620
ttgacaaaac ccagcttgct tccacaaaat catcccaata ccctcacccg tagtcgaccc    1680
ctcgatttgc ggccctatat gaccacaccc tcaaacaaac atcccctct ttcctccctc     1740 cccctgctgt acaactccgc acgccctagg taccacaggc acaatgcggc tcactaacaa    1800
tcaaaacaga gccgaggaaa ttagaaaaaa atacgggtag aagagggata ttcagagacc    1860
agggcaagtc acccgagtct ctgctctctc ctctacctga tagattagga caaatatggc    1920 caccttaca gatgcggaga tcgacgagct atttgagaca agtggaactg tgattgacaa     1980
cataattaca gcccagggta aatcagcaga gactgttgga aggagtgcaa tcccacatgg    2040
caaaaccaag gcgctgagcg cagcatggga gaagcatggg agcatccagc caccggccag    2100
tcaagacacc cctgatcgac aggacagatc tgacaaacaa ccatccacac ccgagcaagc    2160
gaccccgcat gacagcccgc cggccacatc cgccgaccag cccccaccc aggccacaga     2220 cgaagccgtc gacacacagc tcaggaccgg agcaagcaac tctctgctgt tgatgcttga    2280
caagctcagc aataaatcgt ccaatgctaa aaagggccca tggtcgagcc cccaagaggg    2340
gaaccaccaa cgtccgactc aacagcaggg aagtcaaccc agccgcggaa acagccagga    2400
aagaccgcag aaccaagtca aggccgcccc tggaaaccag ggcacagacg cgaacacagc    2460
atatcatgga caatgggagg agtcacaact atcagctggt gcaacccctc atgctctccg    2520
atcaaggcag agccaagaca ataccttgt atctgcggat catgtccagc cacctgtaga    2580 cttttgtgcaa gcgatgatgt ctatgatgga ggcaatatca cagagagtaa gtaaggttga    2640
ctatcagcta gatcttgtct tgaaacagac atcctccatc cctatgatgc ggtccgaaat    2700
ccaacagctg aaaacatctg ttgcagtcat ggaagccaat ttgggaatga tgaagattct    2760
ggatcccggt tgtgccaacg tttcatctct gagtgatcta cgggcagttg cccgatctca    2820
cccggtttta gtttcaggcc ctggagaccc atctccctat gtgactcaag gaggcgaaat    2880
ggcacttaat aaactttcgc aaccagtgcc acatccatct gaattgatta aacccgccac    2940
tgcatgcggg cctgatatag gagtggaaaa ggacactgtc cgtgcattga tcatgtcacg    3000
cccaatgcac ccgagttctt cagccaagct cctaagcaag ctagatgcag ccgggtcgat    3060
cgaggaaatc aggaaaatca agcgccttgc actaaatggc taattactac tgccacacgt    3120
agcgggtccc cgtccactcg gcatcacacg gaatctgcac cgagtccccc ccgcagacc    3180 taaggtccaa ctctccaagt ggcaatcctc tctcgcttcc tcagccccac tgaatgatcg    3240
cgcaaccgta attaatctag ctacattaag gattaagaaa aaatacgggt agaattggag    3300
tgccccaatt gtgccaagat ggactcatct aggacaattg ggctgtactt tgattctgcc    3360
cattcttcta gcaacctgtt agcatttccg atcgtcctac aagacacagg agatgggaag    3420
aagcaaatcg ccccgcaata taggatccag cgcctagact cgtggactga tagtaaagaa    3480
```

```
gactcagtat tcatcaccac ctatggattc atctttcagg ttgggaatga agaagccact    3540
gtcggcatga tcaatgataa tcccaagcgc gagttacttt ctgctgcgat gctctgccta    3600
ggaagcgtcc caaataccgg agaccttgtt gagctggcaa gggcctgtct cactatggta    3660
gtcacatgca agaagagtgc aactaatact gagagaatgg ttttctcagt agtgcaggca    3720
ccccaagtgc tgcaaagctg tagggttgtg gcaaacaaat actcatcagt gaatgcagtc    3780
aagcacgtga aagcgccaga gaagatcccc gggagtggaa ccctagaata caaggtgaac    3840
tttgtctcct tgactgtggt accgaagaag gatgtctaca agatcccaac tgcagtattg    3900
aaggtttctg gctcgagtct gtacaatctt gcgctcaatg tcactattaa tgtggaggta    3960
gactcgagga gtcctttggt taaatctctg tctaagtctg acagcggata ctatgctaac    4020
ctcttcttgc atattggact tatgaccacc gtagatagga gggggaagaa agtgactttt    4080
gacaagctag aaaagaagat aaggagcctt gatctatctg tcgggctcag tgatgtgctc    4140
ggaccttccg tgctggtaaa agcaagaggt gcacggacca agcttttggc acctttcttc    4200
tctagcagtg ggacagcctg ctatcccata gcaaatgcct ctcctcaggt ggccaagata    4260
ctctggagtc aaaccgcgtg cctgcggagc gttaaaatca ttatccaagc aggtacccaa    4320
cgcaccgtcg cagtgaccgc tgaccacgag gttacctcta ctaagctgga aaggggcac     4380 acccttgcca aatacaatcc ttttaagaaa taagctgcgt ctctgagatt gcgctacgcc    4440
cactcaccca gagcatcatg acaccaaaaa ctaatctgtc ctgattattt acagttagtt    4500
tacctgtcta tcaaattaga aaaaacacgg gtagaagatt ctggatcccg gttggcgcct    4560
tctaggtgca agatgggccc cagaccttct accaagaacc cagtacctat gatgctgact    4620
gtccgagtcg cgctggtact gagttgcatc tgtccggcaa actccattga tggcaggcct    4680
cttgcggctg caggaattgt ggtaacagga gacaaagcag tcaacatata cacctcatcc    4740
cagacaggat caatcatagt taagctcctc ccaaacctgc caaggataa  ggaggcatgt    4800 gcgaaagccc ccttggatgc atacaacagg acattgacca cttgctcac  ccccttggt    4860 gactctatcc gtaggataca agagtctgta actacatctg gagggaggag acagaaacgc    4920
tttataggcg ccattattgg cggtgtggct cttggggttg caactgctgc acaaataaca    4980
gcggccgcag ctctgataca agccaaacaa aatgctgcca acatcctccg acttaaagag    5040
agcattgccg caaccaatga ggccgtgcat gaggtcactg acggattatc gcaactagca    5100
gtggcagttg gaagatgca gcagtttgtt aatgaccaat taataaaac agctcaggaa    5160 ttaggctgca tcagaattgc acagcaagtt ggtgtagagc tcaacctgta cctaaccgaa    5220
ttgactacag tattcggacc acaaatcact tcacctgcct taaacaagct gactattcag    5280
gcactttaca atctagctgg tgggaatatg gattacttgt tgactaagtt aggtgtaggg    5340
aacaatcaac tcagctcatt aatcggtagc ggcttaatca ccggcaaccc tattctgtac    5400
gactcacaga ctcaactctt gggtatacag gtaactctac cttcagtcgg gaacctaaat    5460
aatatgcgtg ccacctactt ggaaaacctta tccgtaagca caaccagggg atttgcctcg    5520
gcacttgtcc caaaagtggt gacacaggtc ggttctgtga tagaagaact tgacacctca    5580
tattgtatag aaaccgactt ggatttatat tgtacaagaa tagtaacatt ccctatgtcc    5640
cctggtattt attcctgctt gagcggcaat acatcggcct gtatgtactc aaagaccgaa    5700
ggcgcactca ctacgccata catgactatc aaaggctcag tcatcgctaa ctgcaagatg    5760
acaacatgta gatgcgtaaa ccccccgggt atcatatcgc aaaactatgg agaagccgtg    5820
tctctaatag ataagcaatc atgcaatgtt ttatccttag acgggataac tttaaggctc    5880
```

```
agtggggaat tcgatgcaac ttatcagaag aatatctcaa tacaagattc tcaagtaata   5940
ataacaggca atcttgatat ctcaactgag cttgggaatg tcaacaactc gatcagtaat   6000
gctttgaata agttagagga aagcaacagc aaactagaca aagtcaatgt caaactgacc   6060
agcacatctg ctctcattac ctatatcgtt ttgactatca tatctcttgt ttttggtata   6120
cttagcctgg ttctagcatg ctacctaatg tataagcaaa aggcgcaaca aaagaccttca   6180 ttatggcttg ggaataatac cctagatcag atgagagcca ctacaaaaat gtgaacacag   6240
atgaggaacg aaggtatccc taatagtaat ttgtgtgaaa gttctggtag tctgtcaatt   6300
cggagagttt agaaaaaact acgcgttgta gatgaccaaa ggacgatata cgggtagaac   6360
ggtaagagag gccgcccctc aattgcgagc cgggcttcac aacctccgtt ctaccgcttc   6420
accgacagca gtcctcagtc atggaccgcg cagttagccg agttgcgtta gagaatgatg   6480
aaagagaggc aaaaaataca tggcgcttga tattccggat tgcaatctta ctcttaacag   6540
tagtgacctt agctacatct gtagcctccc ttgtatatag catgggggct agcacaccta   6600
gcgaccttgt aggcataccg accaggattt ctagggcaga agaaaagatt acatctgcac   6660
ttggttccaa tcaagatgta gtagatagga tatataagca agtggccctt gagtctccgt   6720
tggcattgtt aaacactgag accacaatta tgaacgcaat aacatctctc tcttatcaga   6780
ttaatggagc tgcgaacaac agcgggtggg gggcacctat ccatgaccca gattttatcg   6840
gggggatagg caaagaactc attgtagatg atgctagtga tgtcacatca ttctatccct   6900
ctgcatttca agaacatctg aatttttatcc cggcgcctac tacaggatca ggttgcactc   6960
ggataccttc atttgacatg agtgctaccc attactgcta cactcataat gtaatattgt   7020
ctggatgcag agatcactca cactcacatc agtatttagc acttggtgtg ctccggacaa   7080
ctgcaacagg gaggatattc ttttctactc tgcgttccat cagtctggat gacacccaaa   7140
atcggaagtc ttgcagtgtg agtgcaactc ccttaggttg tgatatgctg tgctcgaaag   7200
tcacggagac agaggaagaa gattataact cagctgtccc tacgctgatg gcacatggga   7260
ggttagggtt cgacggccaa taccacgaaa aggacctaga cgtcacaaca ttatttgagg   7320
actgggtggc caactaccca ggagtagggg gtggatcttt tattgacggc cgcgtatggt   7380
tctcagtcta cggagggctg aaacccaatt cacccagtga cactgtacag gaagggaaat   7440
atgtaatata caagcgatac aatgacacat gcccagtga gcaagactac cagatccgaa   7500
tggccaagtc ttcgtataag cccgggcggt ttggtgggaa acgcatacag caggctatct   7560
tatctatcaa ggtgtcaaca tctttgggcg aagacccagt actgactgta ccgcccaaca   7620
cagtcacact catgggggcc gaaggcagaa ttctcacagt agggacatct catttcttgt   7680
atcagcgagg gtcatcatac ttctctcccg cgttattata tcctatgaca gtcagcaaca   7740
aaacagccac tcttcatagt ccctatacat tcaatgcctt cactcggcca ggtagtatcc   7800
cttgccaggc ttcagcaaga tgccccaact cgtgtgttac tggagtctat acagatccat   7860 atccctaat cttctatagg aaccacacct tgcgaggggt attcgggaca atgcttgata   7920
gtgaacaagc aagacttaat cctgcgtctg cagtattcga tagcacatcc cgcagtcgca   7980
taactcgagt gagttcaagc agcaccaaag cagcatacac aacatcaact tgttttaaag   8040
ttgtcaagac caataagacc tattgtctca gcattgctga aatatctaat actctcttcg   8100
gagaattcag aatcgtcccg ttactagttg agatcctcaa aaatgatggg gttagagaag   8160
ccaggtctgg ttagttgagt caactatgaa agagctggga agatggcatt gtatcaccta   8220
```

```
tcttccgaga caccaagaat caaactgaat gccggtgcga gctcgaattc catgtcgcca   8280
gttgaccaca atcagccagt gctcatgcga tcagatcaag tcttgtcaat agtccctcga   8340
ttaagaaaaa atgtaagtgg caatgagata caaggcaaaa cagctaccgg tacgggtaga   8400
aggacatgga gaaaaaaatc actggatata ccaccgttga tatatcccaa tggcatcgta   8460
aagaacattt tgaggcattt cagtcagttg ctcaatgtac ctataaccag accgttcagc   8520
tggatattac ggccttttta aagaccgtaa agaaaaataa gcacaagttt tatccggcct   8580
ttattcacat tcttgcccgc ctgatgaatg ctcatccgga attccgtatg caatgaaag    8640 acggtgagct ggtgatatgg gatagtgttc acccttgtta caccgttttc catgagcaaa   8700
ctgaaacgtt ttcatcgctc tggagtgaat accacgacga tttccggcag tttctacaca   8760
tatattcgca agatgtggcg tgttacggtg aaaacctggc ctatttccct aaagggttta   8820
ttgagaatat gttttcgtc tcagccaatc cctgggtgag tttcaccagt tttgatttaa    8880
acgtggccaa tatggacaac ttcttcgccc ccgttttcac catgggcaaa tattatacgc   8940
aaggcgacaa ggtgctgatg ccgctggcga ttcaggttca tcatgccgtt tgtgatggct   9000
tccatgtcgg cagaatgctt aatgaattac aacagtactg cgatgagtgg cagggcgggg   9060
cgtaatgatt agaaaaaact cgattagaaa aaataccggt aaatagtacg ggtaggacat   9120
ggcgagctcc ggtcctgaaa gggcagagca tcagattatc ctaccagagt cacacctgtc   9180
ttcaccattg gtcaagcaca aactacttta ttactgaaaa ttaactgggc taccgcttcc   9240
tgatgaatgt gacttcgacc acctcattct cagcagacaa tggaaaaaaa tacttgaatc   9300
ggcctctcct gatactgaga gaatgataaa actcggaagg gcagtacacc aaactctcaa   9360
ccacaattct agaataaccg gagtactcca ccccaggtgt ttagaagaac tggctagtat   9420
tgaggtccct gattcaacca acaaatttcg gaagattgag aagaagatcc aaattcacaa   9480
cacgagatat ggagaactgt tcacaaggct gtgtacgcat atagagaaga aactgctggg   9540
gtcatcctgg tctaacaatg tcccccggtc agaggagttc aacagcatcc gtacggatcc   9600
ggcattctgg tttcactcaa aatggtccac agccaagttt gcatggctcc atataaaaca   9660
gatccagagg catctgattg tggcagctag gacaaggtct gcggccaaca aattggtgat   9720
gctaacccat aaggtaggcc aagtctttgt cactcctgaa cttgtcattg tgacgcatac   9780
gaatgagaac aagttcacat gtcttaccca ggaacttgta ttgatgtatg cagatatgat   9840
ggagggcaga gatatggtca acataatatc aaccacggcg gtgcatctca gaagcttatc   9900
agagaaaatt gatgacattt tgcagttaat agacgctctg gcaaaagact tgggcaatca   9960
agtctacgat gttgtatcac taatggaggg attttgcatac ggagctgtcc agctgctcga  10020
gccgtcaggt acatttgcag gagatttctt cgcattcaac ctgcaggagc ttaaagacat  10080
tctaatcggc ctcctcccca atgatatagc agaatccgtg actcatgcaa tagctactgt  10140
attctctggt ttagaacaga atcaagcagc tgagatgttg tgcctgttgc gtctgtgggg  10200
tcacccactg cttgagtccc gtattgcagc aaaggcagtc aggagccaaa tgtgcgcacc  10260
gaaaatggtg gactttgata tgatccttca ggtactgtct ttcttcaagg gaacaatcat  10320
caacggatac agaagaagaa atgcaggtgt gtggccgcga gtcaaagtgg atacaatata  10380
tgggaagatc attgggcaac tacatgcaga ttcagcagag atttcacacg atatcatgtt  10440
gagagagtat aagagtttat ctgcacttga atttgagcca tgtatagaat acgaccctgt  10500
cactaacctg agcatgttcc taaaagacaa ggcaatcgca caccctaacg ataattggct  10560
tgcctcgttt aggcggaacc ttctctccga agaccagaag aaacatgtaa aagaagcaac  10620
```

```
ttcgactaat cgcctcttga tagagttttt agagtcaaat gattttgatc catataaaga    10680
gatggaatat ctgacgaccc ttgagtacct tagagatgac gatgtggcag tatcatactc    10740
gctcaaagag aaggaagtga aagttaatgg acggatcttc gctaagctga caaagaagtt    10800
aaggaactgt caggtgatgg cggaagggat cctagccgac cagattgcac ctttctttca    10860
gggaaatgga gtcattcagg atagcatatc gttgaccaag agtatgctag cgatgagtca    10920
actgtctttt aacagcaata agaaacgtat cactgactgt aaagaaagag tatcttcaaa    10980
ccgcaatcat gatccgaaga gcaagaaccg tcggagagtt gcaaccttca taacaactga    11040
cctgcaaaag tactgtctta attggagata tcagacaatc aaactgttcg ctcatgccat    11100
caatcagttg atgggcctac ctcacttctt tgagtggatt caccctaagac tgatggacac    11160 tacaatgttc gtaggagacc ctttcaatcc tccaagtgac cctactgacc gtgacctctc    11220
aagagtccct aatgatgaca tatatattgt cagtgccaga gggggtatcg aaggattatg    11280
tcagaagcta tggacaatga tctctattgc tgcaatccaa cttgctgcag ctagatcgca    11340
ttgtcgcgtt gcctgtatgg tacagggtga taatcaagta atagcagtaa cgagagaggt    11400
aagatcagac gactctccgg agatggtgtt gacacagttg catcaagcca gtgataattt    11460
cttcaaggaa ttaattcatg tcaatcattt gattggccat aatttgaagg accgtgaaac    11520
catcaggtca gacacattct tcatatacag caaacgaatc ttcaaagatg gagcaatcct    11580
cagtcaagtc ctcaaaaatt catctaaatt agtactggtg tcaggtgatc tcagtgaaaa    11640
caccgtaatg tcctgtgcca acattgcctc tactgtagca cggctatgcg agaacgggct    11700
tcccaaggac ttctgttact atttaaacta tataatgagt tgcgtgcaga catactttga    11760
ctctgagttc tccatcacca acaattcgca ccccgatctt aaccagtcgt ggattgagga    11820
catctctttt gtgcactcat atgttctgac tcctgcccaa ttaggggggac ttagtaaccct   11880
```

```
tgcatctctc tacagggtgt caccttacat tcacatatcc aatgattctc aaaggctatt    13020
cactgaagaa ggagtcaaag aggggaatgt ggtttatcaa cagatcatgc tcttgggttt    13080
atctctaatc gaatcgatct ttccaatgac gacaaccagg acatatgatg agatcacatt    13140
gcatctacat agtaaattta gttgctgtat cagggaagca cctgttgcgg ttcctttcga    13200
gctacttggg gtggcaccgg agctaaggac agtgacctca aacaagttta tgtatgatcc    13260
tagccctgta tcggagggag actttgcgag acttgactta gctatcttca agagttatga    13320
gcttaatctg gagtcatatc ccacgataga gctaatgaac attctttcaa tatccagcgg    13380
gaagttgatt ggccagtctg tggttttctta tgatgaagat acctccataa agaatgacgc    13440
cataatagtg tatgacaata cccgaaattg gatcagtgaa gctcagaatt cagatgtggt    13500
ccgcttattt gaatatgcag cacttgaagt gctcctcgac tgttcttacc aactctatta    13560
tctgagagta agaggcctag acaatattgt cttatatatg ggtgatttat acaagaatat    13620
gccaggaatt ctactttcca acattgcagc tacaatatct catcccgtca ttcattcaag    13680
gttacatgca gtgggcctgg tcaaccataa cggatcacac caacttgcag atacggattt    13740
tatcgaaatg tctgcaaaac tgttagtatc ttgcactcga cgtgtgatct ccggcttata    13800
ttcagggaat aagtatgatc tgctgttccc atctgtctta gatgataacc tgaatgagaa    13860
gatgcttcag ctgatatccc ggttatgctg tctgtacacg gtactctttg ctacaacaag    13920
agaaatcccg aaaataagag gcttatctgc agaagagaaa tgttcagtac ttactgagta    13980
tctactgtcg gatgctgtga accattact tagccctgat caggtgagct ctatcatgtc     14040
tcctagcata attacattcc cagctaatct gtactacatg tctcggaaga gcctcaattt    14100
gatcagggaa agggaggaca aggattctat cctggcgttg ttgttccccc aagagccatt    14160
attagagttc ccttctgtgc aagatattgg tgctcgagtg aaagatccat tcacccgaca    14220
acctgcggca tttttgcaag agttagattt gagtgctcca gcaaggtatg acgcattcac    14280
acttagtcag attcatcctg agctcacatc accaaatccg gaggaagact acttagtacg    14340
atacttgttc agaggaatag ggactgcatc ctcctcttgg tataaggcag cccatctcct    14400
ttctgtaccc gaggtaagat gtgcaagaca cgggaactcc ttatacttag ctgaaggaag    14460
cggagccatc ataagtcttc tcgaactgca tgtaccacat gaaactatct attacaatac    14520 gctctttttca aatgagatga accccccgca gcgacatttc gggccgaccc caacccagtt    14580
tttgaattcg gttgtttata ggaacctaca ggcggaggta acatgcaagg atggatttgt    14640
ccaagagttc cgtccactat ggagagaaaa tacagaggaa agcgacctga cctcagataa    14700
agcagtgggg tatattacat ctgcagtgcc ctacagatct gtatcattgc tgcattgtga    14760
cattgaaatc cctccagggt ccaatcaaag cttactagat caattagcta tcaatttatc    14820
tctgattgcc atgcattccg taagggaggg cggggtagtg atcatcaaag tgttgtatgc    14880
aatgggatac tactttcatc tactcatgaa cttgttcgct ccgtgttcca caaaaggata    14940
cattctctct aatggttatg catgtagagg ggatatggag tgttacctgg tatttgtcat    15000
gggttacctg gcgggcta catttgtaca cgaggtggtg aggatggcaa aaactctggt    15060
gcagcggcac ggtacgcttt tgtccaaatc agatgagatc acactgacca ggttattcac    15120
ctcacagcgg cagcgtgtga cagacatcct atccagtcct ttaccaagat taataaagta    15180
cttgagaaag aatattgaca ctgcgctgat tgaagctggg ggacagcccg tccgtccatt    15240
ctgtgcagag agtttggtga gcacgctggc ggatataact cagataaccc agatcattgc    15300
tagtcacatt gacacagtca tccggtctgt gatatatatg gaagctgagg gtgatctcgc    15360
```

```
tgacacagta tttctattta ccccttacaa tctctctact gacgggaaaa agagaacatc   15420
acttaaacag tgcacgagac agatcctaga ggttacaata ttgggtctta gagtcgaaga   15480
tctcaataaa ataggcgatg taatcagcct agtgcttaaa ggcatgatct ccatggagga   15540
ccttatccca ctaaggacat acttgaagca tagtacctgc cctaaatatt tgaaggctgt   15600
cctaggtatt accaaactca agaaatgtt tacagacacc tctgtattgt acttgactcg    15660
tgctcaacaa aaattctaca tgaaaactat aggcaatgca gtcaaaggat attacagtaa   15720
ctgtgactct taacgaaaat cacatattaa taggctcctt ttctggccaa ttgtatcctt   15780
ggtgatttaa ttatactatg ttagaaaaaa attgaactcc gactccttag atctcgaatt   15840
cgaactcaaa taaatgtctt aaaaaaaggt tgcgcacaat tattcttgag tgtagtcttg   15900
ttattcacca aatctttgtt tggtcggcat ggcatctcca cctcctcgcg gtccgcaatg   15960
gcaacaacgt tgcgcaaact attaactggc gaactactta ctctagcttc ccggcaacaa   16020
ttaatagact ggatggaggc ggataaagtt gcaggaccac ttctgcgctc ggcccttccg   16080
gctggctggt ttattgctga taaatctgga gccggtgagc gtgggtctcg cggtatcatt   16140
gcagcactgg ggccagatgg taagccctcc cgtatcgtag ttatctacac gacggggagt   16200
caggcaacta tggatgaacg aaatagacag atcgctgaga taggtgcctc actgattaag   16260
cattggtaac tgtcagacca gtttactca tatatacttt agattgattt aaaacttcat     16320
ttttaattta aaaggatcta ggtgaagatc ctttttgata atctcatgac caaaatccct   16380
taacgtgagt tttcgttcca ctgagcgtca gaccccgtag aaaagatcaa aggatcttct   16440
tgagatcctt ttttttctgcg cgtaatctgc tgcttgcaaa caaaaaaacc accgctacca   16500
gcggtggttt gtttgccgga tcaagagcta ccaactcttt ttccgaaggt aactggcttc   16560
agcagagcgc agataccaaa tactgtcctt ctagtgtagc cgtagttagg ccaccacttc   16620
aagaactctg tagcaccgcc tacatacctc gctctgctaa tcctgttacc agtggctgct   16680
gccagtggcg ataagtcgtg tcttaccggg ttggactcaa gacgatagtt accggataag   16740
gcgcagcggt cgggctgaac ggggggttcg tgcacacagc ccagcttgga gcgaacgacc   16800
tacaccgaac tgagatacct acagcgtgag ctatgagaaa gcgccacgct tcccgaaggg   16860
agaaaggcgg acaggtatcc ggtaagcggc agggtcggaa caggagagcg cacgagggag   16920
cttccagggg gaaacgcctg gtatctttat agtcctgtcg ggtttcgcca cctctgactt   16980
gagcgtcgat ttttgtgatg ctcgtcaggg gggcggagcc tatggaaaaa cgccagcaac   17040
gcggcctttt tacggttcct ggccttttgc tggccttttg ctcacatgtt ctttcctgcg   17100
ttatcccctg attctgtgga taaccgtatt accgcctttg agtgagctga taccgctcgc   17160
cgcagccgaa cgaccgagcg cagcgagtca gtgagcgagg aagcggaaga gcgcctgatg   17220
cggtattttc tccttacgca tctgtgcggt atttcacacc gcatatggtg cactctcagt   17280
acaatctgct ctgatgccgc atagttaagc cagtatacac tccgctatcg ctacgtgact   17340
gggtcatggc tgcgccccga cacccgccaa cacccgctga cgcgccctga cgggcttgtc   17400
tgctcccggc atccgcttac agacaagctg tgaccgtctc cgggagctgc atgtgtcaga   17460
ggttttcacc gtcatcaccg aaacgcgcga ggcagctgcg gtaaagctca tcagcgtggt   17520
cgtgaagcga ttcacagatg tctgcctgtt catccgcgtc cagctcgttg agtttctcca   17580
gaagcgttaa tgtctggctt ctgataaagc gggccatgtt aagggcggtt ttttcctgtt   17640
tggtcacttg atgcctccgt gtaaggggga atttctgttc atgggggtaa tgataccgat   17700
```

```
gaaacgagag aggatgctca cgatacgggt tactgatgat gaacatgccc ggttactgga  17760
acgttgtgag ggtaaacaac tggcggtatg gatgcggcgg gaccagagaa aaatcactca  17820
gggtcaatgc cagcgcttcg ttaatacaga tgtaggtgtt ccacagggta gccagcagca  17880
tcctgcgatg cagatccgga acataatggt gcagggcgct gacttccgcg tttccagact  17940
ttacgaaaca cggaaaccga agaccattca tgttgttgct caggtcgcag acgttttgca  18000
gcagcagtcg cttcacgttc gctcgcgtat cggtgattca ttctgctaac cagtaaggca  18060
accccgccag cctagccggg tcctcaacga caggagcacg atcatgcgca cccgtggcca  18120
ggacccaacg ctgcccgaga tgcgccgcgt gcggctgctg gagatggcgg acgcgatgga  18180
tatgttctgc caagggttgg tttgcgcatt cacagttctc cgcaagaatt gattggctcc  18240
aattcttgga gtggtgaatc cgttagcgag gtgccgccgg cttccattca ggtcgaggtg  18300
gcccggctcc atgcaccgcg acgcaacgcg gggaggcaga caaggtatag ggcggcgcct  18360
acaatccatg ccaacccgtt ccatgtgctc gccgaggcgg cataaatcgc cgtgacgatc  18420
agcggtccag tgatcgaagt taggctggta agagccgcga gcgatccttg aagctgtccc  18480
tgatggtcgt catctacctg cctggacagc atggcctgca acgcgggcat cccgatgccg  18540
ccggaagcga gaagaatcat aatggggaag gccatccagc ctcgcgtcgc gaacgccagc  18600
aagacgtagc ccagcgcgtc ggccgccatg ccggcgataa tggcctgctt ctcgccgaaa  18660
cgtttggtgg cgggaccagt gacgaaggct tgagcgaggg cgtgcaagat tccgaatacc  18720
gcaagcgaca ggccgatcat cgtcgcgctc cagcgaaagc ggtcctcgcc gaaaatgacc  18780
cagagcgctg ccggcacctg tcctacgagt tgcatgataa agaagacagt cataagtgcg  18840
gcgacgatag tcatgccccg cgcccaccgg aaggagctga ctgggttgaa ggctctcaag  18900
ggcatcggtc gacgctctcc cttatgcgac tcctgcatta ggaagcagcc cagtagtagg  18960
ttgaggccgt tgagcaccgc cgccgcaagg aatggtgcat gcaaggagat ggcgcccaac  19020
agtcccccgg ccacggggcc tgccaccata cccacgccga aacaagcgct catgagcccg  19080
aagtggcgag cccgatcttc cccatcggtg atgtcggcga tataggcgcc agcaaccgca  19140
cctgtggcgc cggtgatgcc ggccacgatg cgtccgcgt agaagatcca caggacgggt  19200
gtggtcgcca tgatcgcgta gtcgatagtg gctccaagta gcgaagcgag caggactggg  19260
cggcggccaa agcggtcgga cagtgctccg agaacgggtg cgcatagaaa ttgcatcaac  19320
gcatatagcg ctagcagcac gccatagtga ctggcgatgc tgtcggaatg gacgatatcc  19380
cgcaagaggc ccggcagtac cggcataacc aagcctatgc ctacagcatc cagggtgacg  19440
gtgccgagga tgacgatgag cgcattgtta gatttcatac acggtgcctg actgcgttag  19500
caatttaact gtgataaact accgcattaa agcttatcga tgataagctg tcaaacatga  19560
gaa                                                               19563
```

RECOMBINANT NEWCASTLE DISEASE VIRUSES USEFUL AS VACCINES OR VACCINE VECTORS

CROSS REFERENCE TO RELATED APPLICATIONS

This application is a Continuation of U.S. patent application Ser. No. 10/440,419, filed May 19, 2003; which is a Continuation-In-Part application of U.S. patent application Ser. No. 09/926,431, filed Mar. 6, 2002, now U.S. Pat. No. 7,244,558; which is National Stage entry of International Application No.: PCT/US00/06700 filed on May 5, 2000. The present patent application also claims the benefit of U.S. Provisional Patent Application Nos. 60/381,462 filed on May 17, 2002; 60/132,597, filed May 5, 1999; and 60/171,072, filed Dec. 16, 1999. The disclosures of each of these applications are hereby incorporated in their entirety by reference.

SEQUENCE LISTING

The instant application contains a Sequence Listing which has been submitted electronically in ASCII format and is hereby incorporated by reference in its entirety. Said ASCII copy, created on Sep. 22, 2014, is named 108172-00146_SL.txt and is 84,473 bytes in size.

The present application relates to recombinant Newcastle disease viruses carrying one or more foreign genes, i.e. genes not found naturally in the Newcastle disease virus, which are useful as vaccines or vaccine vectors.

BACKGROUND OF THE INVENTION

Newcastle disease is a highly contagious viral disease affecting all species of birds. The disease can vary from an asymptomatic infection to a highly fatal disease, depending on the virus strain and the host species. Newcastle disease has a worldwide distribution and is a major threat to the poultry industries of all countries. Based on the severity of the disease produced in chickens, Newcastle disease virus (NDV) strains are grouped into three main pathotypes: lentogenic (strains that do not usually cause disease in adult chickens), mesogenic (strains of intermediate virulence) and velogenic (strains that cause high mortality).

NDV is a member of the genus *Rubulavirus* in the family Paramyxoviridae. The genome of NDV is a non-segmented, single-stranded, negative-sense RNA of 15186 nucleotides (Krishnamurthy & Samal, 1998; Phillips et el., 1998; de Leeuw & Peeters, 1999). The genomic RNA contains six genes that encode the following proteins in the order of: the nucleocapsid protein (NP), phosphoprotein (P), matrix protein (M), fusion protein (F), haemagglutinin-neuraminidase (HN) and large polymerase protein (L). Two additional proteins, V and W, of unknown function are produced by RNA editing during P gene transcription (Steward et al., 1993). A schematic diagram of the genetic map of NDV genomic RNA is shown in FIG. 1.

Three proteins, i.e. NP, P and L proteins, constitute the nucleocapsid. The genomic RNA is tightly bound by the NP protein and together with the P and L proteins form the functional nucleocapsid within which resides the viral transcriptive and replicative activities. The F and HN proteins form the external envelope spikes, where the HN glycoprotein is responsible for attachment of the virus to host cell receptors and the F glycoprotein mediates fusion of the viral envelope with the host cell plasma membrane thereby enabling penetration of the viral genome into the cytoplasm of the host cell. The HN and F proteins are the main targets for the immune response. The M protein forms the inner layer of the virion.

NDV follows the general scheme of transcription and replication of other non-segmented negative-strand RNA viruses. The polymerase enters the genome at a promoter in the 3' extragenic leader region and proceeds along the entire length by a sequential stop-start mechanism during which the polymerase remains template bound and is guided by short consensus gene start (GS) and gene end (GE) signals. This generates a free leader RNA and six non-overlapping subgenomic mRNAs. The abundance of the various mRNAs decreases with increasing gene distance from the promoter. The genes are separated by short intergenic regions (1-47 nucleotides) which are not copied into the individual mRNAs. RNA replication occurs when the polymerase somehow switches to a read-through mode in which the transcription signals are ignored. This produces a complete encapsulated positive-sense replicative intermediate which serves as the template for progeny genomes.

Reverse-genetic techniques have been reported to recover negative-sense viruses from cloned cDNA (Conzelmann, 1996). For NDV, reverse-genetic technology is currently available for avirulent strain LaSota (Römer-Oberdörfer et al., 1999; Peeters et al., 1999).

SUMMARY OF THE INVENTION

Reverse-genetic techniques were used in making the recombinant NDV of the present invention from cloned cDNA. This approach involves co-expression of the cloned cDNA of full length NDV genome and nucleocapsid proteins (the NP, P and L proteins) from transfected plasmids using the vaccinia virus/T7 RNA polymerase expression system.

Within the scope of the present invention, recombinant NDV can be recovered from cDNA and the genome of NDV can be manipulated at the cDNA level. The production of infectious NDV from cloned cDNA can be used to engineer NDV carrying foreign genes. With the manipulation of the genome of NDV, one can insert foreign sequences into the NDV genome for co-expression. For example, the gene for protective antigen of another avian pathogen or the genes for avian cytokines can be inserted into the NDV genome for co-expression. Thus, the present invention includes multivalent genetically engineered NDV vaccines carrying genes encoding immunogens (e.g. immunogenic proteins) for influenza virus, infectious bursal disease virus, rotavirus, infectious bronchitis virus, infectious laryngotracheitis virus, chicken anemia virus, Marek's disease virus, avian Leukosis virus, avian adenovirus and avian pneumovirus.

The present invention also is directed toward a genetically engineered NDV carrying avian cytokine genes. A NDV carrying at least one gene encoding an avian cytokine, e.g. an interleukin such as IL-2 and IL-4, can be used as a vaccine.

The recombinant NDV prepared by insertion of foreign genes into the NDV genome can express the foreign genes in cells infected by the recombinant NDV. As a result, the recombinant NDV can be used to express proteins of non-avian pathogens or other avian pathogens. Therefore, the recombinant NDV can be used as a vaccine vector.

One of the objects of the present invention is a recombinant antigenomic RNA of Newcastle disease virus, comprising NP gene, P gene, M gene, F gene, HN gene and L gene in this order from a 5' to 3' direction, said antigenomic RNA further comprising n foreign nucleotide complexes inserted (a) before the NP gene, (b) between the P and M genes, and/or (c) between the HN and L genes, wherein n is 1, 2, 3 or 4;

each of the foreign nucleotide complexes comprising a Newcastle disease virus gene start sequence, an open reading frame of a foreign gene and a Newcastle disease virus gene end sequence in this order from the 5' to 3' direction, wherein the foreign gene is a gene not found naturally in the Newcastle disease virus;

wherein when n is 2, 3 or 4, the foreign nucleotide complexes are the same or different; and wherein when 2, 3 or 4 foreign nucleotide complexes are inserted together before the NP gene, between the P and M genes, or between the HN and L genes, the foreign nucleotide complexes are sequentially linked directly or indirectly.

Since each foreign nucleotide complex has a NDV gene start signal, i.e. GS sequence motif, upstream of the open reading frame (ORF) of the foreign gene and a NDV gene end signal, i.e. GE sequence motif, downstream of the ORF of the foreign gene, each foreign nucleotide complex forms a transcriptional unit.

The recombinant antigenomic RNA of NDV of the present invention preferably further comprises NP-P intergenic region between the NP gene and P gene, P-M intergenic region between the P gene and M gene, M-F intergenic region between the M gene and F gene, F-HN intergenic region between the F gene and HN gene, and/or HN-L intergenic region between the HN gene and L gene. More preferably, the recombinant antigenomic RNA of NDV of the present invention further comprises NP-P intergenic region between the NP gene and P gene, P-M intergenic region between the P gene and M gene, M-F intergenic region between the M gene and F gene, F-HN intergenic region between the F gene and HN gene, and HN-L intergenic region between the HN gene and L gene. When one or more of the foreign nucleotide complexes are inserted between the P and M genes, the foreign nucleotide complexes can be inserted into the P-M intergenic region if present. Similarly, when one or more of the foreign nucleotide complexes are inserted between the HN and L genes, the foreign nucleotide complexes can be inserted into the HN-L intergenic region. Optionally, one or more of the NP-P intergenic region, P-M intergenic region, M-F intergenic region, F-HN intergenic region, and HN-L intergenic region are replaced with a single nucleotide, dinucleotide or an oligonucleotide of 3-80 nucleotides (preferably 4-60 nucleotides) in length, wherein the oligonucleotide optionally contains one or more restriction sites.

When one or more of the foreign nucleotide complexes are inserted before the NP gene, the foreign nucleotide complexes preferably are inserted into a non-coding region immediately before the ORF of the NP gene, so that the ORF of the foreign gene in each of the foreign nucleotide complexes is flanked by NDV gene start and gene end signals and the ORF of the NP gene is preceded by a NDV gene start signal, with the GS-foreign gene ORF-GE structure preceding the GS signal for the NP ORF.

Within the scope of the invention is a recombinant antigenomic RNA of NDV having one or more foreign nucleotide complexes inserted between P and M genes. The antigenomic RNA can be made by inserting the one or more foreign nucleotide complexes into the noncoding region of P gene after the stop codon, but before the NDV gene end signal of the P gene. When only one foreign nucleotide complex is inserted into the noncoding region of P gene after the stop codon, the ORF of the foreign gene is preceded by a NDV gene end and NDV gene start signals, resulting in the ORF of the P gene being preceded by a NDV gene end signal, which is followed by a NDV gene start signal, the ORF of the foreign gene, and a NDV gene end signal in that order (the ORF of the following M gene is preceded by a NDV gene start signal). More foreign gene complexes can be inserted after this foreign gene complex. Similarly, the recombinant antigenomic RNA of NDV having one or more foreign nucleotide complexes inserted between P and M genes can be made by inserting the one or more foreign nucleotide complexes into the noncoding region of M gene before the ORF of the M gene.

The present invention is also directed toward a process of preparing the recombinant antigenomic RNA of the invention, comprising the following steps:

(i) providing a cDNA comprising NP gene, P gene, M gene, F gene, HN gene and L gene in this order, said cDNA further comprising n foreign nucleotide complexes inserted (a) before the NP gene, (b) between the P and M genes, and/or (c) between the HN and L genes, wherein n is 1, 2, 3 or 4;

each of the foreign nucleotide complexes comprising a Newcastle disease virus gene start sequence, an open reading frame of a foreign gene and a Newcastle disease virus gene end sequence in this order from the 5' to 3' direction, wherein the foreign gene is a gene not found naturally in the Newcastle disease virus;

wherein when n is 2, 3 or 4, the foreign nucleotide complexes are the same or different; and wherein when 2, 3 or 4 foreign nucleotide complexes are inserted together before the NP gene, between the P and M genes, or between the HN and L genes, the foreign nucleotide complexes are sequentially linked directly or indirectly;

(ii) transcribing the antigenomic cDNA to form a mixture containing an antigenomic RNA; and thereafter (iii) isolating the antigenomic RNA.

In some embodiments of the process of preparing the recombinant antigenomic RNA of the invention, the cDNA used in step (i), comprising NP gene, P gene, M gene, F gene, HN gene and L gene having the n foreign nucleotide complexes inserted, is prepared by (I) constructing a cDNA comprising the NP gene, P gene, M gene, F gene, HN gene and L gene in this order; and thereafter (II) inserting the n foreign nucleotide complexes (a) before the NP gene, (b) between the P and M genes, and/or (c) between the HN and L genes. Preferably, the cDNA constructed in step (I) and/or the cDNA constructed in step (II) are in a plasmid, such as pBR322 or pGEM-7Z. In step (ii), the cDNA preferably is transcribed in cells expressing a RNA polymerase, such as T7 RNA polymerase.

The present invention is also directed toward a recombinant NDV comprising a recombinant antigenomic RNA carrying one or more foreign genes of the present invention. The recombinant NDV can be produced by a process comprising the following steps:

(i) providing cells capable of synthesizing T7 RNA polymerase;

(ii) transfecting the cells with a plasmid comprising the cDNA encoding the antigenomic RNA having one or more foreign genes inserted according to the invention, a plasmid encoding NP protein, a plasmid encoding P protein, and a plasmid encoding L protein to obtain transfected cells in a medium; and thereafter (iii) isolating Newcastle disease virus from a supernatant of the medium of step (ii) to obtain the recombinant Newcastle disease virus.

The cells capable of synthesizing T7 RNA polymerase provided in step (i) can be animal cells of an avian or mammalian species, plant cells, or cells from a cell line expressing T7 RNA polymerase.

Within the scope of the present invention are a cDNA encoding a recombinant antigenomic RNA having one or more foreign genes inserted according to the invention, a cell containing the cDNA, a plasmid comprising the cDNA, a cell containing the plasmid, a cell containing the recombinant antigenomic RNA, and a recombinant NDV containing the recombinant antigenomic RNA of the invention, e.g. a recombinant NDV carrying one or more foreign genes recovered from transcription of the cDNA or the plasmid in a competent cell. The recombinant NDV containing the recombinant antigenomic RNA of the invention is preferably substantially purified. Also preferred is a substantially purified recombinant antigenomic RNA of NDV carrying one or more foreign genes prepared according to the invention.

The present invention also includes a method of vaccinating an avian animal against Newcastle disease, wherein the avian animal is in need of the vaccination, comprising administering an effective amount of the recombinant NDV carrying one or more foreign genes according to the invention to the avian animal.

One of the objects of the inventions is a method of treating an avian animal with an avian cytokine, wherein the avian animal is in need of the treatment, said method comprising administering an effective amount of the recombinant NDV of the invention carrying one or more foreign genes encoding one or more avian cytokines, such as avian interleukins (preferably IL-2 and/or IL-4) to the avian animal.

Another aspect of the invention is a method of immunizing an avian animal against an avian pathogen selected from the group consisting of influenza virus, infectious bursal disease virus, rotavirus, infectious bronchitis virus, infectious laryngotracheitis virus, chicken anemia virus, Marek's disease virus, avian Leukosis virus, avian adenovirus and avian pneumovirus, wherein the avian animal is in need of the immunization, said method comprising administering an effective amount of the recombinant NDV of the invention to the avian animal, wherein the recombinant NDV carries one or more foreign genes encoding one or more immunogenic proteins of the avian pathogen against which the avian animal is immunized.

Also within the scope of the invention is a method of immunizing a mammal against a non-avian pathogen, wherein the mammal is in need of the immunization, said method comprising administering an effective amount of the recombinant NDV of the invention to the mammal, wherein the recombinant NDV carries one or more foreign genes encoding one or more immunogenic proteins of the non-avian pathogen, e.g. influenza virus, SARS-causing virus, human respiratory syncytial virus, human immunodeficiency virus, hepatitis A virus, hepatitis B virus, hepatitis C virus, poliovirus, rabies virus, Hendra virus, Nipah virus, human parainfluenza 3 virus, measles virus, mumps virus, Ebola virus, Marburg virus, West Nile virus, Japanese encephalitis virus, Dengue virus, Hantavirus, Rift Valley fever virus, Lassa fever virus, herpes simplex virus and yellow fever virus, against which the mammal is immunized.

BRIEF DESCRIPTION OF THE DRAWINGS

FIG. 1 is a schematic of the genetic map of NDV genomic RNA, wherein L gene END is SEQ ID NO:1, gene START and NP gene START are SEQ ID NO:2 and gene END is SEQ ID NO:3.

FIG. 2 is a map of the genome of NDV strain Beaudette C, wherein the nucleotide sequence of the NP region is available from the GenBank database with the accession number AF064091 (the disclosed sequences in order from 5' to 3' are SEQ ID NO: 4, 5, 6, 2, 7, 2, 8, 2, 9, 2, 10, 2, and 11, respectively). In FIG. 2, the last nucleotide of the gene end, the first nucleotide of the gene start and the first and last nucleotides of the leader and trailer are numbered. The gene start and gene end sequences were derived from published sources of the NDV.

FIG. 4 shows the construction of pLaSota/CAT, wherein SEQ ID NO:12 and 13 are displayed in the figure. An 18 nt fragment containing a PmeI site was inserted into the non-coding region immediately before the NP ORF. The ORF of the CAT gene was amplified by PCR with PmeI-tagged primers, digested with PmeI and introduced into the newly created PmeI site of the NP gene. A set of NDV gene-end (GE) and gene-start (GS) signals normally connected to the NP-P intergenic sequence was placed at the end of the CAT gene. The resulting plasmid pLaSota/CAT gave rise to an antigenomic RNA of 15900 nt, which is a multiple of six.

FIG. 5 shows plaques produced by rLaSota and rLaSota/CAT on DF1 cells. Infected cells overlaid with 1% methylcellulose were incubated for a period of 4 days. Plaques were visualized by immunostaining using a monoclonal antibody against the NDV HN protein.

FIG. 14 shows a recombinant vaccinia virus-based transfection system used to recover infectious NDV from a plasmid containing a recombinant cDNA to the genome of NDV.

FIG. 16 depicts schematically the construction of a recombinant cDNA encoding an antigenome of NDV strain Beaudette C having a foreign gene, a gene encoding GFP, inserted into the noncoding region of P gene by creating a XbaI site via mutation of a TCTCGC segment (nucleotide positions 3182-3187) forming a TCTAGA segment in the P gene noncoding region after a stop codon. The sequence preceding GFP is SEQ ID NO:18. The underlined sequence, TTAGAAAAAA (SEQ ID NO: 19), represents a cDNA fragment for a NDV gene end signal and the underlined sequence, ACGGGTAGAA (SEQ ID NO: 20), represents a cDNA fragment for a NDV gene start signal.

DETAILED DESCRIPTION OF THE INVENTION

Figure 3:
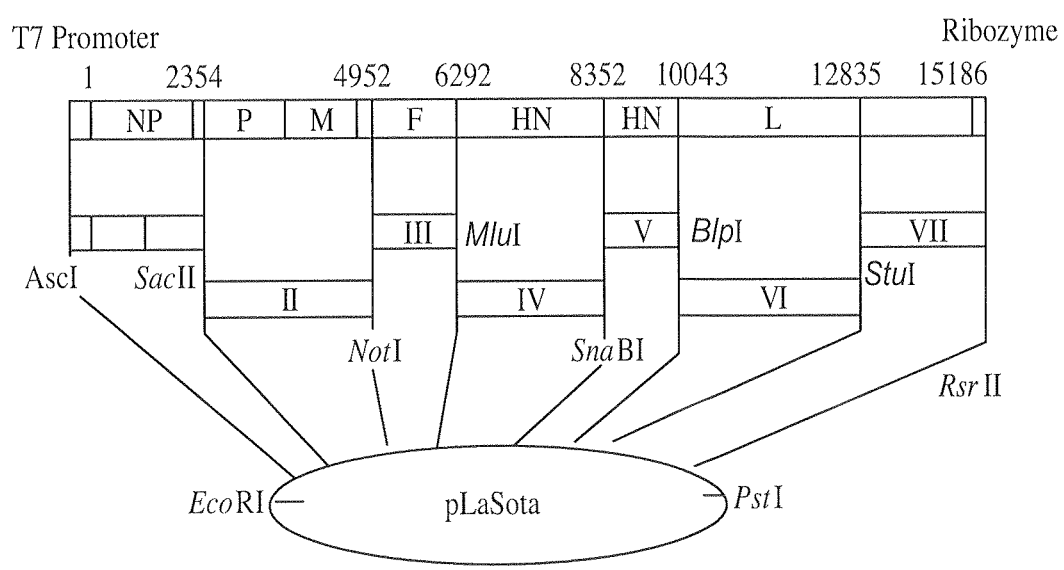
FIG. 3 shows the assembly of full-length cDNA of NDV strain LaSota. Seven subgenomic cDNA fragments generated by high-fidelity RT-PCR were assembled in pBR322/dr (SEQ ID NO: 57) (not to scale). The numbers above the cDNA in FIG. 3 are the first nucleotide positions of various restriction sites. Plasmid pBR322 was modified to include a 72 nt oligonucleotide linker between the EcoRI and PstI sites, an 84 nt hepatitis delta virus (HDV) antigenome ribozyme sequence and a T7 RNA polymerase transcription-termination signal. Transcription of the plasmid pLaSota by T7 RNA polymerase resulted in NDV antigenomic RNA with three non-viral G residues at the 5' terminus.

In some embodiments of the recombinant antigenomic RNA of the present invention, n is 2, 3 or 4 (preferably 2 or 3, and more preferably 2) and the foreign nucleotide complexes are different. In some embodiments of the recombinant antigenomic RNA, n is 2, 3 or 4 (preferably 2 or 3, and more preferably 2) and the foreign nucleotide complexes are the same. In still some embodiments of the recombinant antigenomic RNA, n is 1 or 2.

In some of the recombinant antigenomic RNAs of the invention, the ORF of each of the foreign genes in inserted the foreign nucleotide complexes is no more than about 3000 nucleotides, no more than about 2000 nucleotides, no more than about 1500 nucleotides, no more than about 1000 nucleotides, no more than about 800 nucleotides, no more than about 500 nucleotides, or no more than about 300 nucleotides in length.

In some of the embodiments of the recombinant antigenomic RNA of the present invention, where 2, 3 or 4 foreign nucleotide complexes are inserted together before the NP gene, between the P and M genes, or between the HN and L genes, the foreign nucleotide complexes are sequentially linked directly or indirectly, and the foreign nucleotide complexes have a combined length of no more than about 5000 nucleotides, no more than about 4000 nucleotides, no more than about 3000 nucleotides, no more than about 2000 nucleotides, no more than about 1000 nucleotides, or no more than about 800.

The foreign gene inserted in the recombinant antigenomic RNA of the invention preferably encode a substance selected from the group consisting of chloramphenical acetyltransferase, GFP, an avian cytokine, and an immunogenic protein of influenza virus, infectious bursal disease virus, rotavirus, infectious bronchitis virus, infectious laryngotracheitis virus, chicken anemia virus, Marek's disease virus, avian leukosis virus, avian adenovirus, or avian pneumovirus. The foreign gene may encode an immunogenic protein of a non-avian pathogen, e.g. influenza virus, SARS-causing virus, human respiratory syncytial virus, human immunodeficiency virus, hepatitis A virus, hepatitis B virus, hepatitis C virus, poliovirus, rabies virus, Hendra virus, Nipah virus, human parainfluenza 3 virus, measles virus, mumps virus, Ebola virus, Marburg virus, West Nile disease virus, Japanese encephalitis virus, Dengue virus, Hantavirus, Rift Valley fever virus, Lassa fever virus, herpes simplex virus and yellow fever virus.

When more than one foreign gene encoding the avian cytokine is inserted, the foreign genes may encode the same or different avian cytokines, such as avian interleukins, e.g. IL-2 and IL-4.

Examples of the foreign gene encoding an immunogenic protein of an avian pathogen are HA or NA gene of influenza virus, VP2 or polyprotein gene of infectious bursal disease virus, S or S1 gene of infectious bronchitis virus, glycoprotein gene of infectious laryngotracheitis virus, the complete genome of chicken anemia virus, glycoprotein gene of Marek's disease virus, envelope gene of avian leukosis virus, avian adenovirus, and G or F gene of avian pneumovirus.

Examples of the foreign gene encoding an immunogenic protein of a non-avian pathogen are HA or NA gene of influenza virus, S or S1 gene of SARS-causing virus, G or F gene of human respiratory syncytial virus, gp60, gp120 or gp41 gene of human immunodeficiency virus, surface antigen gene of hepatitis A virus, surface antigen gene of hepatitis B virus, surface antigen of hepatitis C virus, capsid proteins gene of poliovirus, G protein gene of rabies virus, G or F protein gene of Hendra virus, G or F protein gene of Nipah virus, HN or F protein gene of human parainfluenza 3 virus, H or F protein gene of measles virus, HN or F protein gene of mumps virus, G protein gene of Ebola virus, G protein gene of Marburg virus, envelope protein gene of West Nile disease virus, envelope protein gene of Japanese encephalitis virus, envelope protein gene of Dengue virus, glycoprotein gene of Hantavirus, glycoprotein gene of Rift Valley fever virus, G1 or G2 protein gene of Lassa fever virus, glycoprotein genes of herpes simplex virus, and glycoprotein gene of yellow fever virus.

The present invention is also directed toward an antigenomic RNA of NDV carrying one or more foreign genes inserted before the NP gene, between the P and M genes, and/or between the HN and L genes, wherein at least one of the foreign genes encodes a tumor antigen, such as pg100, MAGE1, MAGE3 and CDK4.

In the recombinant antigenomic RNA of the invention, the foreign nucleotide complexes preferably are inserted before the NP gene, and/or between the P and M genes. More preferably, at least one of the foreign nucleotide complexes is inserted before the NP gene. In some embodiments of the recombinant antigenomic RNA, at least one of the foreign nucleotide complexes is inserted before the NP gene and at least one of the foreign nucleotide complexes is inserted between the P and M genes. In some embodiments, at least one of the foreign nucleotide complexes is inserted before the NP gene and at least one of the foreign nucleotide complexes is inserted between the HN and L genes. In still some embodiments, at least one of the foreign nucleotide complexes is inserted before the NP gene, at least one of the foreign nucleotide complexes is inserted between the P and M genes, and at least one of the foreign nucleotide complexes is inserted between the HN and L genes. In yet some embodiments, at least one of the foreign nucleotide complexes is inserted between the P and M genes. Most preferably, the foreign nucleotide complexes are inserted only before the NP gene.

NDV grows to very high titers ($<10^9$ PFU/ml) in many cell lines and eggs and elicits strong humoral and cellular immune responses in vivo. NDV naturally infects via respiratory and alimentary tract mucosal surfaces. NDV replicates in the cytoplasm of infected cells and does not undergo genetic recombination, making vaccine vectors based on the recombinant NDV carrying foreign genes stable and safe. Due to these characteristics of NDV described herein, recombinant NDVs that can express foreign genes carried in the recombinant NDVs are good vaccines, wherein the foreign genes encode immunogenic proteins of pathogens.

The recombinant NDV on the invention carrying one or more inserted foreign genes show robust expression of the foreign genes. Moreover, the recombinant NDV expressing one or more of the foreign gene can replicate in cell culture and in vivo. Avirulent NDV recombinants expressing heterologous proteins could be used as multivalent vaccines.

The recombinant NDV generated from the recombinant antigenomic RNA carrying one or more foreign genes inserted according to the invention can also be used as an inactivated vaccine.

The vaccine or vaccine vector based on the recombinant NDV generated from the recombinant antigenomic RNA carrying one or more foreign genes inserted according to the invention can be administered topically, via the respiratory route, orally or via an injection. The dose of the vaccine or vaccine vector to be used can be readily determined by a person skilled in the art based on the disease, the host subject species, and the age, sex and/or health condition of the host subject involved.

Within the scope of the present invention is a method to recover NDV with amino acid changes at the cleavage site. The codon of the changed amino acid is different from that of the original amino acid by at least two nucleotides. Such a difference in at least two nucleotides stabilizes the viral genome against reversion from a nonbasic amino acid residue to a basic amino acid residue.

Within the scope of the present invention is a Newcastle disease virus having at least two of the features selected from the group consisting of (1) a $F_0$ protein cleavage site having at least two less basic amino acid residues than a $F_0$ protein cleavage site of Newcastle disease virus wild type strain Beaudette C; (2) an amino acid having a non-aromatic side chain at the N terminus of the $F_1$ cleavage fragment, wherein the amino acid having a non-aromatic side chain is glycine, alanine, valine, leucine or isoleucine, preferably leucine; and (3) an open reading frame of a HN glycoprotein being longer than an open reading frame of a HN glycoprotein of Newcastle disease virus wild type strain Beaudette C.

Example 1

In this working example, an embodiment of the invention in which the recombinant NDV containing CAT as the foreign gene inserted before the NP gene was prepared.

A. Assembly of a Full-Length Clone of NDV Strain LaSota and Recovery of NDV LaSota from a Plasmid NDV lentogenic strain LaSota was grown in 10-day-old embryonated, specific-pathogen-free (SPF) eggs. The virus was purified from allantoic fluid as described previously (Kingsbury, 1966). Viral RNA was extracted from the purified virus by using TRIzol according to the manufacturer's protocol (Life Technologies). The extracted RNA was subjected to RT-PCR with virus-specific primer pairs (Table 1) to generate seven overlapping PCR fragments of the entire viral genome with high-fidelity Pfx DNA polymerase (Life Technologies). In Table 1, the cDNA fragments correspond to the fragments shown in FIG. 3, wherein the T7 promoter sequence is in italics, virus sequences are underlined, restriction sites are in bold, and the partial HDV ribozyme sequence (24 nt) overhang is shown in lower case. A low-copy-number plasmid, pBR322, was modified as pBR322/dr to contain a 72 nt linker between the EcoRI and PstI sites for subsequent assembly of full-length NDV strain LaSota. The LaSota strain cDNA was placed in the antigenomic orientation between the T7 promoter and a self-cleaving hepatitis delta virus (HDV) antigenome ribozyme, followed by a T7 RNA polymerase terminator (FIG. 3). Two genetic markers were introduced into the full-length cDNA for the purpose of identifying the recovered virus. An MluI site was created in the F-HN intergenic region and a SnaBI site was created in the HN-L intergenic region. For the construction of NP, P and L expression plasmids, the open reading frame (ORF) of each gene was amplified from the above full-length clone by PCR. The NP gene was cloned in the plasmid pGEM-7Z (Promega) between EcoRI and BamHI sites. The P and L genes were cloned in an expression plasmid that has an encephalomyocarditis virus internal ribosome entry site (IRES) downstream of the T7 RNA polymerase promoter, and they make use of the translation start codon contained in the NcoI site of the IRES. The assembled full-length cDNA clone and the support plasmids encoding LaSota NP, P and L proteins were sequenced in their entirety. The resulting full-length clone and support plasmids were designated pLaSota, pNP, pP and pL, respectively.

A cDNA clone encoding NDV strain LaSota antigenomic RNA was assembled from seven cDNA fragments, as shown in FIG. 3. This plasmid, termed pLaSota, positioned the NDV cDNA between the T7 promoter and the HDV ribozyme sequence. During its construction, the antigenomic cDNA was modified to generate two new restriction sites as markers. A genetic marker was introduced into the intergenic region between the F and HN genes by changing two nucleotides to mutate the original AgeI site to a unique MluI site (positions 6292-6297 in the full-length cDNA clone). Similarly, a unique SnaBI site was generated in the HN and L intergenic region by changing four nucleotides (positions 8352-8357). To facilitate transcription by T7 RNA polymerase, three G residues were included before the NDV leader sequence.

Figure 6:
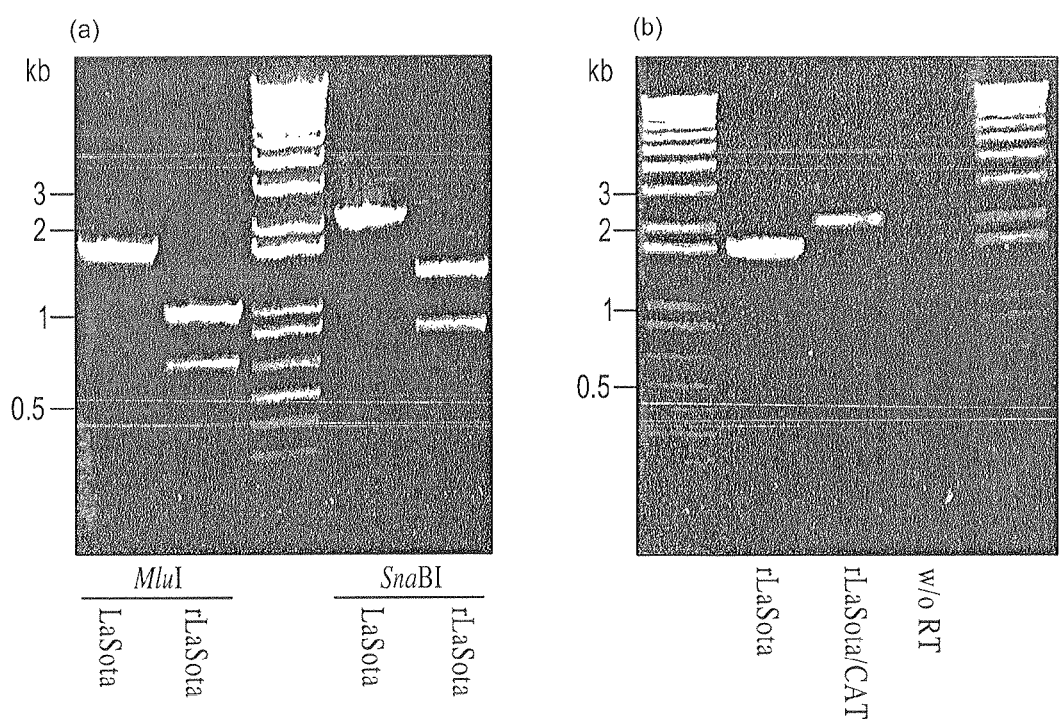
FIG. 6 shows the identification of genetic markers in the genome of rLaSota and confirmation of the presence of the CAT gene in the genome of rLaSota/CAT. RT-PCR was performed from genomic RNA extracted from purified viruses. (a) Identification of genetic markers in the genome of rLaSota. Primers spanning the corresponding regions were used for PCR and the products were subjected to restriction enzyme digestion. Wild-type LaSota was used as control. (b) Confirmation of the presence of the CAT gene in the recovered rLaSota/CAT by PCR with specific primers. The larger RT-PCR product (2.3 kb) from rLaSota/CAT confirmed the presence of the CAT gene compared with the smaller RT-PCR product (1.6 kb) from rLaSota.

In order to recover NDV from the cloned cDNA to the antigenome of NDV LaSota, transfection was carried out as described here (based on a general procedure schematically shown in FIG. 14). HEp-2 cells (6-well plates) were infected at 1 p.f.u. per cell with modified vaccinia virus (MVA/T7) expressing T7 RNA polymerase. A mixture of a plasmid containing NP gene ORF, a plasmid containing P gene ORF, and a plasmid containing L gene ORF all under the control of the T7 promoter (2.5, 1.5 and 0.5 µg per well, respectively) and a fourth plasmid encoding the NDV (5 µg) was transfected with LipofectAMINE Plus (Life Technologies). Four hours after transfection, cells were washed and the medium was replaced with 2 ml fresh medium (DMEM with 0% foetal calf serum and 1 µg/ml acetyltrypsin). Three days post-transfection, the supernatant was harvested, clarified and used to infect fresh HEp-2 cells. Three days later, 100 µl supernatant was taken to inoculate into the allantoic cavity of 10-day-old embryonated SPF eggs. After 96 h, allantoic fluid was harvested and tested for haemagglutinating (HA) activity. After two passages in eggs, the virus was plaque-purified to eliminate vaccinia virus. The plaques produced by the virus were stained with monoclonal antibodies specific to the NDV HN protein to confirm the specificity of the recovered virus (FIG. 5). The recovered viruses were designated rLaSota. To identify the recovered virus, two genetic markers (MluI and SnaBI) were introduced in the full-length cDNA clone. In order to verify the presence of these markers, RNA from recovered virus was subjected to RT-PCR. DNA fragments encompassing the regions containing the MluI and SnaBI sites were subjected to restriction enzyme digestion with the respective enzymes. Analysis of the restriction enzyme patterns revealed the presence of both genetic markers in rLaSota, as calculated from the sizes of the bands, while RT-PCR products from wild-type LaSota were not digested by the enzymes (FIG. 6a).

Nucleotide sequence analysis of RT-PCR products also confirmed the presence of the genetic markers. The procedures for RT-PCR and demonstration of genetic marker are described herein. RNA was isolated from recovered virus by using TRIzol reagent. RT-PCR was performed with primers P1 (5' TCCCCTGGTATTTATTCCTGC, (SEQ ID NO: 21) positions 5609-5629) and P1R (5' GTTGGCCACCCAGTC-CCCGA, (SEQ ID NO: 22) negative sense, positions 7286-7305) to amplify a fragment including the introduced MluI site in the intergenic region between the F and HN genes. Similarly, a fragment containing the SnaBI site within the HN-L intergenic region was amplified with primers P2 (5' CGCATACAGCAGGCTATCTTATC, (SEQ ID NO: 23) positions 7513-7535) and P2R (5'GGGTCATATTCTATA-CATGGC, (SEQ ID NO: 24) negative sense, positions 9739-9759). The RT-PCR products were then subjected to restriction enzyme digestion, the first product with MluI, the second with SnaBI. The restriction patterns were analysed by agarose gel electrophoresis. RT-PCR was also performed to demonstrate the location of the CAT gene insert in the recombinant NDV expressing the CAT gene.

Figure 4:
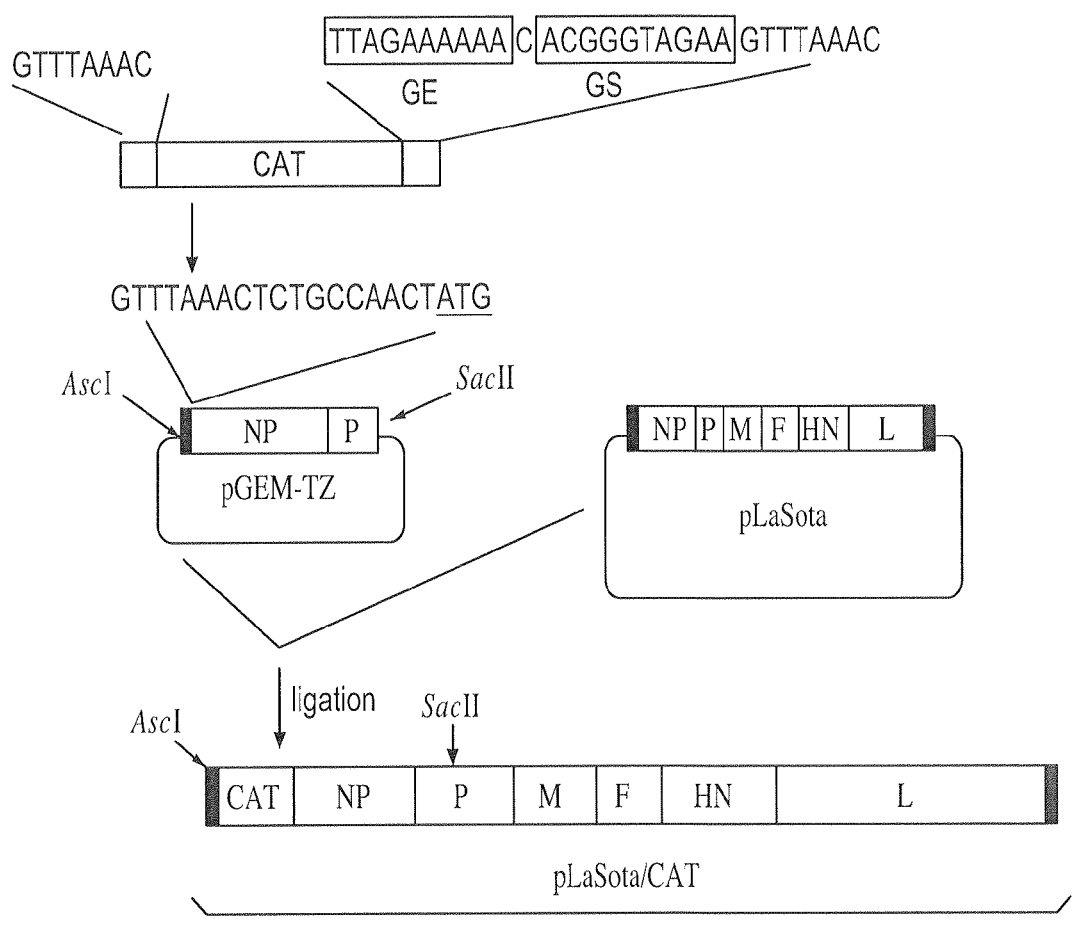

B. Construction of a Full-Length Plasmid Containing the Chloramphenicol Acetyltransferase (CAT) Gene For the convenience of inserting CAT into the most 3'-proximal locus, an AscI-SacII fragment of the full-length cDNA clone was subcloned into plasmid pGEM-7Z between the XbaI and HindIII sites by using a specific primer pair with XbaI and HindIII site overhangs. An 18 nt insert with a unique PmeI site was then introduced just before the NP ORF by the method described previously (Byrappa et al., 1995). To insert the CAT gene into the PmeI site, the CAT gene ORF was amplified by primers (5' gctagtttaaacATG-GAGAAAAAAATCACTGGATATACC 3' (SEQ ID NO: 25), positive sense, and 5' gctagtttaaacttctacccgtgtttttctaatct-gcagTTACGCCCCGCCCTGCCACTCAT CGC 3' (SEQ ID NO: 26), negative sense; PmeI site and NDV gene start and gene end signal in lower case, CAT-specific sequence in capitals), digested with PmeI and placed into the NP non-coding region in pGEM-7Z (FIG. 4). Clones with the CAT gene in the correct orientation were chosen for sequencing. The AscI-SacII fragment containing the CAT gene was used to replace the corresponding fragment in pLaSota. Thus, an additional transcriptional unit, the CAT ORF flanked by NDV gene start and gene end signals, was inserted into pLaSota. The total number of nucleotides was adjusted by inserting nucleotides after the CAT gene stop codon to maintain the 'rule of six'. The resulting clone was designated pLaSota/CAT.

The CAT gene ORF, flanked by NDV gene start and gene end sequences, was inserted into the non-coding region of the NP gene immediately before the NP ORF (FIG. 4). The resulting plasmid would encode an antigenome of 15900 nt, obeying the 'rule of six' (Peeters et al., 2000). In the recovered virus, the inserted CAT gene would be expressed as a monocistronic mRNA under the control of the NDV transcription system. The method for recovery of recombinant NDV was the same as described above. Plaques produced by rLaSota/CAT were immunostained with HN-specific monoclonal antibody and were of a size and morphology similar to those produced by rLaSota. The presence of the CAT gene in the genome of recovered virus was verified by RT-PCR with oligonucleotide primers spanning the CAT gene. The size of the RT-PCR product from recovered rLaSota was 1.6 kb, while that from rLaSota/CAT was 2.3 kb (FIG. 6b). Direct PCR from extracted RNA without RT did not yield any product. Nucleotide sequence analysis of the RT-PCR product confirmed the presence of the CAT gene in the genome of the recovered virus rLaSota/CAT.

Figure 7:
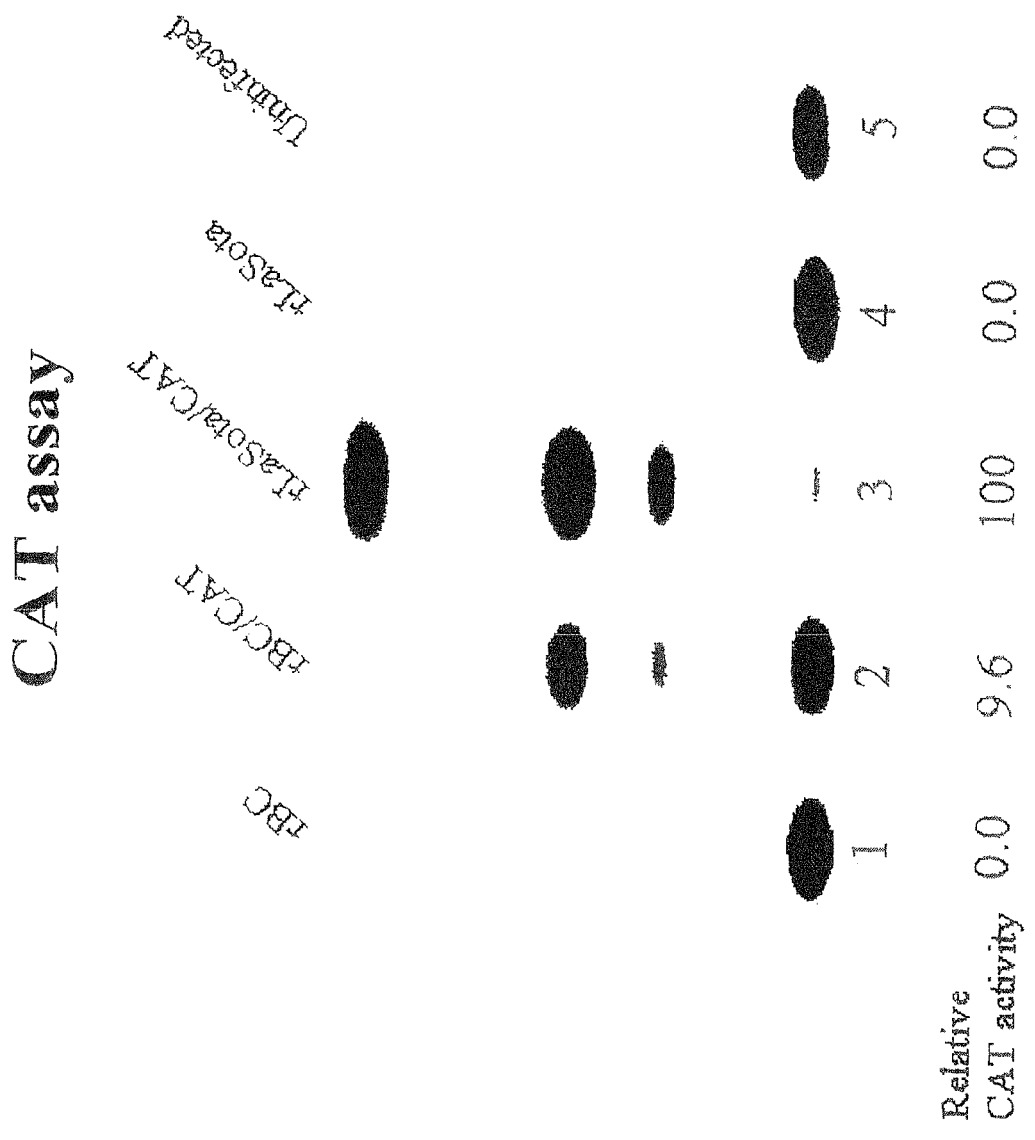
FIG. 7 shows a comparison of CAT expression by a recombinant virus (rBC/CAT) recovered from a cDNA encoding a recombinant antigenomic RNA of NDV Beaudette C having a CAT gene inserted between HN and L genes as prepared in Example 2 and a recombinant virus (rLaSota/CAT) recovered from a cDNA encoding a recombinant antigenomic RNA of NDV LaSota having a CAT gene inserted before NP gene as prepared in Example 1 at passage 6. The CAT gene was expressed from the sixth position in rBC/CAT while it was expressed from the first position in rLaSota/CAT. Equal cell equivalents of lysates were analysed for acetylation of [$^{14}$C]chloramphenicol as visualized by thin-layer chromatography. Relative CAT activity was quantified by densitometry.

To examine the expression of the CAT protein from rLaSota/CAT, cell lysates from 12 passages, beginning with the third, were tested for CAT activity. For rLaSota/CAT, all passages showed similar CAT enzyme activity by CAT assay (procedure described below, but data not shown). These results showed that the inserted CAT gene was stable, at least up to passage 12. In Example 2 described below, an NDV-CAT chimeric transcription cassette was inserted between the HN and L genes of the full-length cDNA of virulent NDV strain Beaudette C and infectious CAT-expressing recombinant NDV (rBC/CAT) was recovered. In order to compare the level of expression of the CAT genes from rLaSota/CAT and rBC/CAT, replicate monolayers of DF1 cells were infected with each virus separately at an m.o.i. of 0.1. Four days after infection, CAT enzyme activities in the cell lysates were examined (FIG. 7). The results showed that the CAT enzyme activity was about 11-fold higher in cells infected with rLaSota/CAT than in cells infected with rBC/CAT.

The activity of CAT was assayed as described below for analysis of the stability of CAT expression. Chicken embryo fibroblast DF1 cell pellets were lysed by three freeze-thaw cycles and 1% of the lysed pellet from a 25 cm2 flask was analysed by TLC for the ability to acetylate [$^{14}$C]chloramphenicol (Amersham Pharmacia). To study the stability of CAT expression by the recombinant virus, a total of 12 serial passages were performed at a passage interval of 4 days. At each passage, 100 µl of the medium supernatant was used for passing to fresh DF1 cells in a 25 cm2 flask. Acetyltrypsin (1 µg/ml) was included in the medium of DF1 cells for cleavage of the F protein of rLaSota and rLaSota/CAT.

Figure 8:
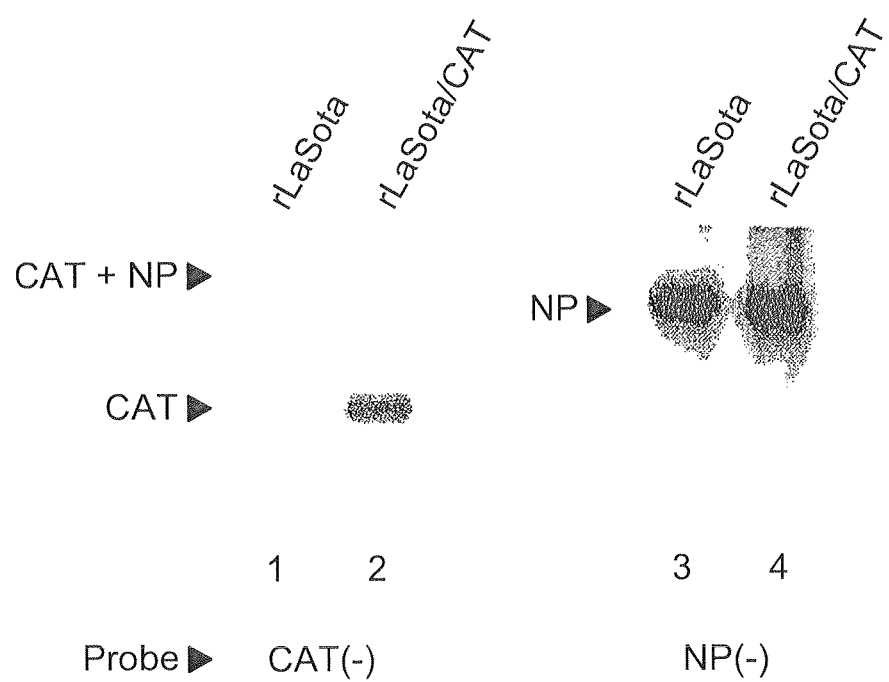
FIG. 8 shows results of Northern blot hybridization blot hybridization of intracellular mRNAs encoded by rLaSota and rLaSota/CAT. Poly(A)+mRNAs were isolated from total intracellular RNA by oligo(dT) chromatography and were electrophoresed on formaldehyde-agarose gels. The gels were transferred to nitrocellulose membrane and probed with the negative-sense riboprobes.

To examine the presence of CAT mRNA and the level of synthesis of the immediate downstream NP mRNA, Northern blot hybridization was performed with poly(A)+RNA from cells infected with rLaSota or rLaSota/CAT, each at passage 6. Northern blot hybridization was carried out as described herein. RNA was isolated from cells infected with either rLaSota or rLaSota/CAT at an m.o.i. of 1. Total RNA was extracted with TRIzol reagent and poly(A)+mRNA was selected by using an mRNA isolation kit (Promega). mRNA samples were subjected to electrophoresis on 1.5% agarose gels containing 0.44 M formaldehyde, transferred to nitrocellulose membrane and used for hybridization with [$^{32}$P] CTP-labelled riboprobes. The negative-sense CAT and NP probes where synthesized by in vitro transcription of linearized plasmids containing these genes. Hybridization of the mRNA extracted from rLaSota/CAT-infected cells with a negative-sense CAT-specific riboprobe detected a single major band of the size predicted for CAT mRNA (FIG. 8). Hybridization with a negative-sense riboprobe specific for the NP gene showed a single major band at the size predicted for NP mRNA in both rLaSota and rLaSota/CAT blots. Densitometry scanning did not show a significant difference in the level of NP mRNA synthesis between rLaSota and rLaSota/CAT. This result indicated that insertion of the CAT gene at the most 3'-proximal locus did not affect mRNA synthesis of the immediate downstream NP gene significantly.

Example 2

In this working example, an embodiment of the invention in which the recombinant NDV containing a gene encoding CAT as the foreign gene inserted between the HN and L genes was prepared.

A. Construction of a Full-Length NDV cDNA Clone

Figure 10:
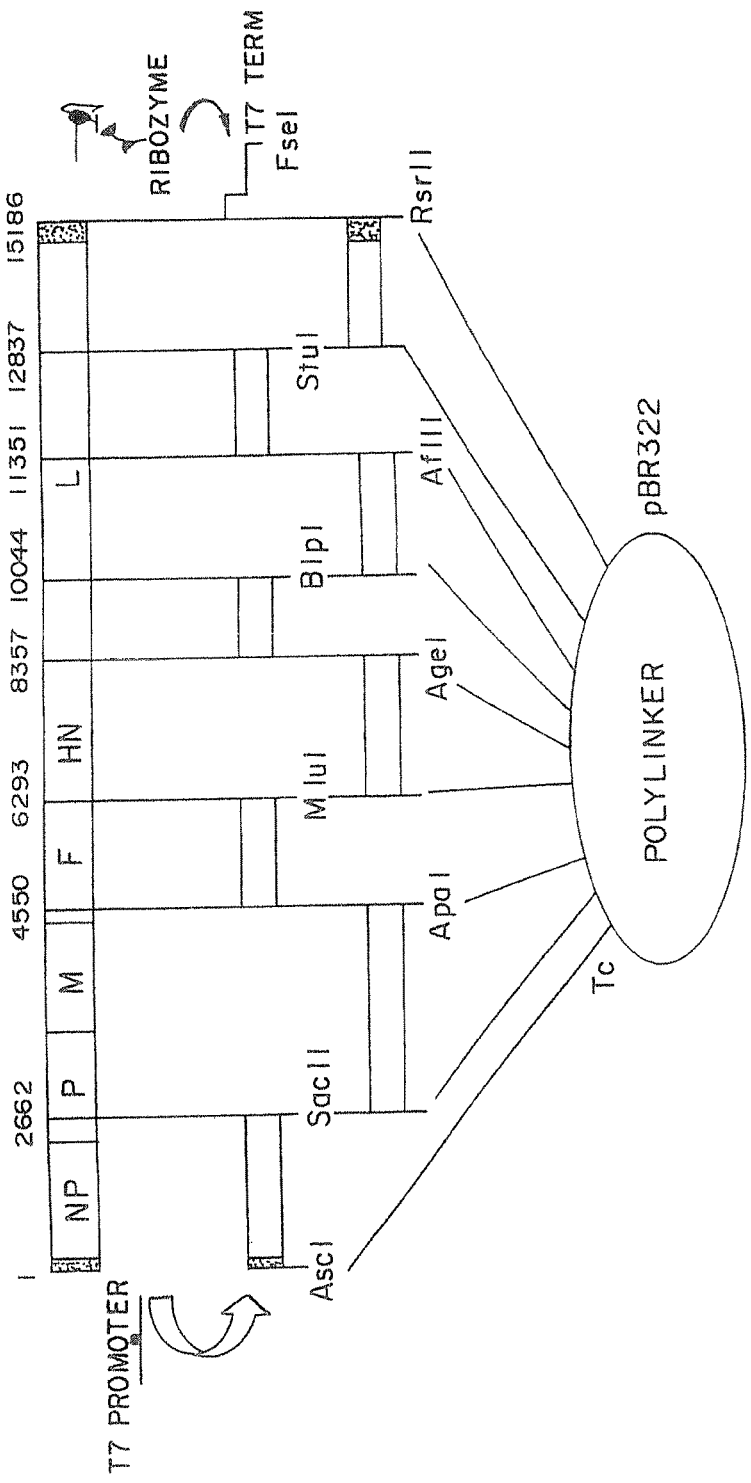
FIG. 10 shows the construction of a full-length cDNA to the genome of NDV strain Beaudette C in a plasmid.
Figure 11:
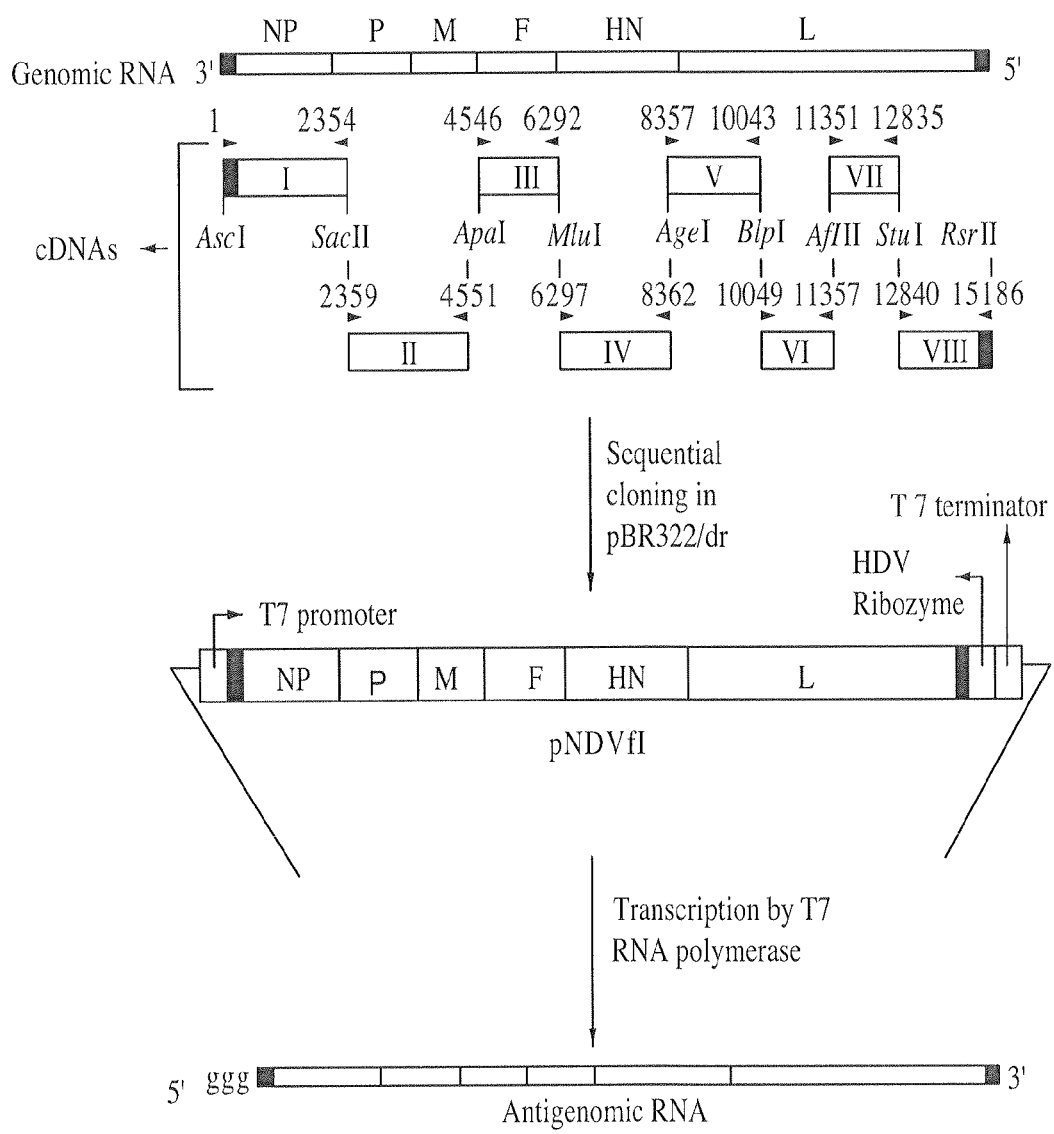
FIG. 11 shows a full-length NDV cDNA assembled in pBR322/dr from subgenomic cDNA fragments (I to VIII) that were generated by high-fidelity RT-PCR (not to scale). The blocked arrows indicate the primers used in RT-PCR. The numbers shown above the primers represent the position in the genome of the first nucleotide of the primer, represented 5' to 3'. Plasmid pBR322/dr is the modified form of plasmid pBR322, designed to include a 72-nucleotide oligonucleotide linker between the EcoRI and PstI sites, an 84-nucleotide hepatitis delta virus (HDV) antigenome ribozyme sequence and a T7 RNA polymerase transcription termination signal. Transcription by the T7 RNA polymerase of the plasmid pNDVfl resulted in the NDV antigenomic RNA with 3 nonviral G residues at the 5' terminus.

A cDNA clone encoding the entire 15,186-nt antigenome of NDV strain Beaudette C was constructed from 8 cDNA segments that were synthesized by RT-PCR from NDV Beaudette C derived genomic RNA (FIG. 10; FIG. 11). The oligonucleotide primers used during full-length antigenomic cDNA synthesis and RT-PCR are shown in Table 2, in which the cDNA fragments correspond to the DNA fragments in FIG. 11. In Table 2, T7 promoter sequences are marked in italic type, the virus-specific sequences are underlined, and restriction sites are marked in bold type; the partial HDV ribozyme sequence (24-nt) overhang is shown in lowercase; and orientation of the primer sequence is shown for sense (+) and antisense (−). Each cDNA fragment was completely sequenced before assembly into the full-length cDNA clone. The leader end was constructed to join a promoter for T7 RNA polymerase. To generate a nearly exact 3' end, the trailer end was constructed to join hepatitis delta virus (HDV) antigenome ribozyme sequence followed by tandem terminators of T7 transcription. Two restriction site markers were introduced into the antigenomic cDNA by incorporating the changes into the oligonucleotide primers used in RT-PCR in order to identify the recombinant virus. An Mlu I site was created in the F-HN intergenic region and the other unique Age I site was created in the HN-L intergenic region. Cloning of these cDNA fragments positioned the NDV cDNA between the T7 promoter and the hepatitis delta virus ribozyme sequence. The resulting recombinant pBR322 plasmid contained the full-length cDNA encoding the antigenome of NDV BeaudetteI C. To facilitate transcription of the cDNA in the plasmid by T7 RNA polymerase later, three G resides were included before the NDV leader sequence.

To recover recombinant NDV from the cDNA located in the plasmid, the strategy shown in FIG. 14 was used. HEp2 cells were infected with recombinant vaccinia virus (MVA/T7) capable of synthesizing T7 RNA polymerase. The HEp2 cells were simultaneously transfected with (1) the recombinant plasmid pBR322 containing the cDNA encoding the antigenomic RNA of NDV Beaudette C, (2) a plasmid containing the NP gene under the control of the T7 promoter, (3) a plasmid containing the P gene under the control of the T7 promoter, and (4) a plasmid containing the L gene under the control of the T7 promoter. Three or four days after the transfection, infectious recombinant NDV was isolated from the supernatant by one of two ways. The supernatant was either injected into the allantoic cavities of 9-day-old embryonated eggs or amplified further in HEp-2 cells and DF1 cells (chicken embryo fibroblast cell line). An antigenomic (+)-sense RNA transcript was produced by transcription of the NDV full-length antigenomic cDNA.

Figure 12:
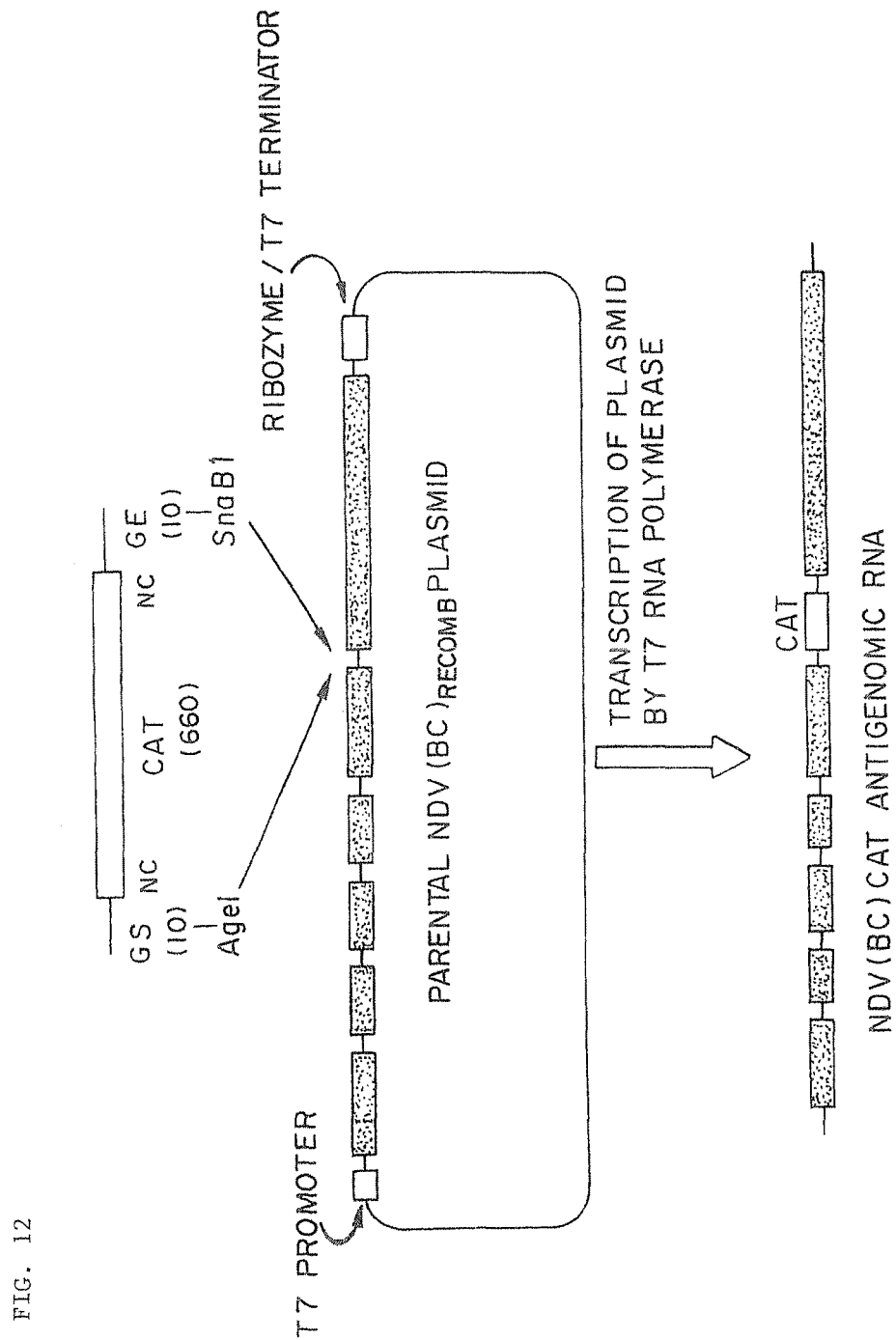
FIG. 12 shows the construction of a recombinant NDV cDNA that contains a foreign gene inserted into the intergenic region between the HN and L genes, wherein the foreign gene means a gene foreign to NDV and in this case the foreign gene is a gene encoding chloramphenical acetyltransferase (CAT).
Figure 13:
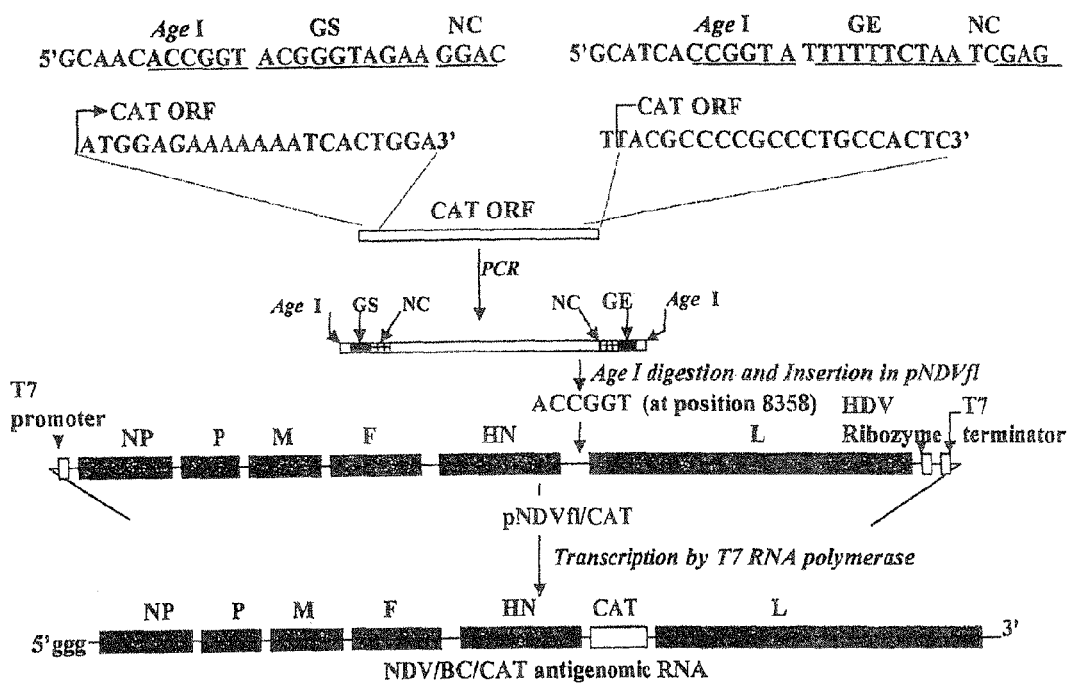
FIG. 13 shows the construction of pNDVfl/CAT (SEQ ID NO: 58) by insertion of the CAT gene cDNA into HN and L intergenic region of the plasmid pNDVfl. The two sequences on the first line of the figure are SEQ ID NO:14 (left) and SEQ ID NO:16 (right), and the two sequences on the second line of the figure are SEQ ID NO:15 (left) and SEQ ID NO:17 (right). The nucleotide sequences represent the oligonucleotide primer used for amplifying the CAT ORF. The resulting PCR product with the AgeI overhang on either end contained the gene start (GS) signal, noncoding (NC) sequence, and gene end (GE) signal. The nucleotide length of the construct was maintained as a multiple of six. The RNA encoded by pNDVfl/CAT included the three 5'-terminal nonviral G residues contributed by the T7 promoter.

B. Construction of Recombinant NDV Having a Foreign Gene Inserted Between the HN and L Genes The recombinant pBR322 plasmid containing the cDNA clone encoding the entire 15,186-nt antigenome of NDV strain Beaudette C prepared in Part A of Working Example 2 above was used to construct the recombinant NDV having a foreign gene inserted. The gene encoding chloramphenicol acetyltransferase (CAT) was the foreign gene in this example. The sequence in the NH-L intergenic region of the full-length antigenome cDNA clone of NDV strain Beaudette C was modified to contain a unique Sna B I restriction site downstream of the Age I restriction site. The open reading frame (ORF) encoding the CAT protein was engineered to be flanked by the NDV GS and GE signals. This transcription cassette was inserted into the HN-L intergenic region of NDV full-length antigenomic cDNA to prepare a recombinant pBR322 containing the full-length antigenomic cDNA containing the CAT gene inserted between the HN and L genes (see FIG. 12; with a more detailed version shown in FIG. 13). In this construct, care was taken over the genome length preference called the "rule of six", i.e. NDV having a preference, but not an absolute requirement, that the number of nucleotides in the genome is a multiple of six.

To recover the recombinant NDV containing the CAT gene, the strategy shown in FIG. 14 was used. The recombinant NDV recovery procedures described in Part B of this working example were used except that the HEp2 cells were simultaneously transfected with (1) the recombinant plasmid pBR322 containing NDV antigenomic cDNA having the CAT gene inserted, (2) a plasmid containing the NP gene, (3) a plasmid containing the P gene, and (4) a plasmid containing the L gene.

Figure 15:
FIG. 15 shows the detection of CAT expression after one passage of infectious recombinant NDV carrying the CAT gene recovered from the recombinant vaccinia virus-based transfection system of FIG. 14, wherein the recombinant NDV resulted from transcription of the recombinant NDV cDNA constructed in FIG. 12.

RT-PCR of the genomic RNA isolated from the recovered virus showed the presence of the inserted CAT gene. The recovered virus expressed abundant levels of CAT enzyme. In FIG. 15, lane 1 shows data from laboratory Beaudette C strain, and lane 2 shows data from recombinant Beaudette C strain containing the CAT gene. Analysis of mRNAs by Northern blot hybridization showed that the CAT gene was expressed as an additional, separate, poly(A) mRNA. CAT expression was stable for at least 8 passages, indicating that the activity of the CAT protein encoded by NDV remained unimpaired by mutation. There was no appreciable difference either in plaque phenotype or in growth kinetics between the virus recovered from the recombinant NDV and wild-type laboratory NDV strain.

Example 3

Some of the characteristics of the recombinant viruses, rLaSota and rLaSota/CAT, were determined using the recombinant viruses recovered from transcription of the recombinant cDNA of NDV carrying the CAT gene inserted before the NP gene or between the HN and L genes as obtained in Examples 1 and 2.

A. Nucleotide Sequences

The nucleotide sequence of the recombinant cDNA for NDV LaSota expressing the CAT gene inserted in front of the NP gene as prepared in Example 1 is shown in Table 3 (labeled as LASO_CAT.TXT). The nucleotide sequence of the recombinant cDNA for NDV Beaudette C expressing the CAT gene inserted between the HN and L genes as prepared in Example 2 is shown in Table 4 (labeled as BC_CAT-_.TXT).

B. Growth Characteristics of the Recombinant Viruses

Figure 9:
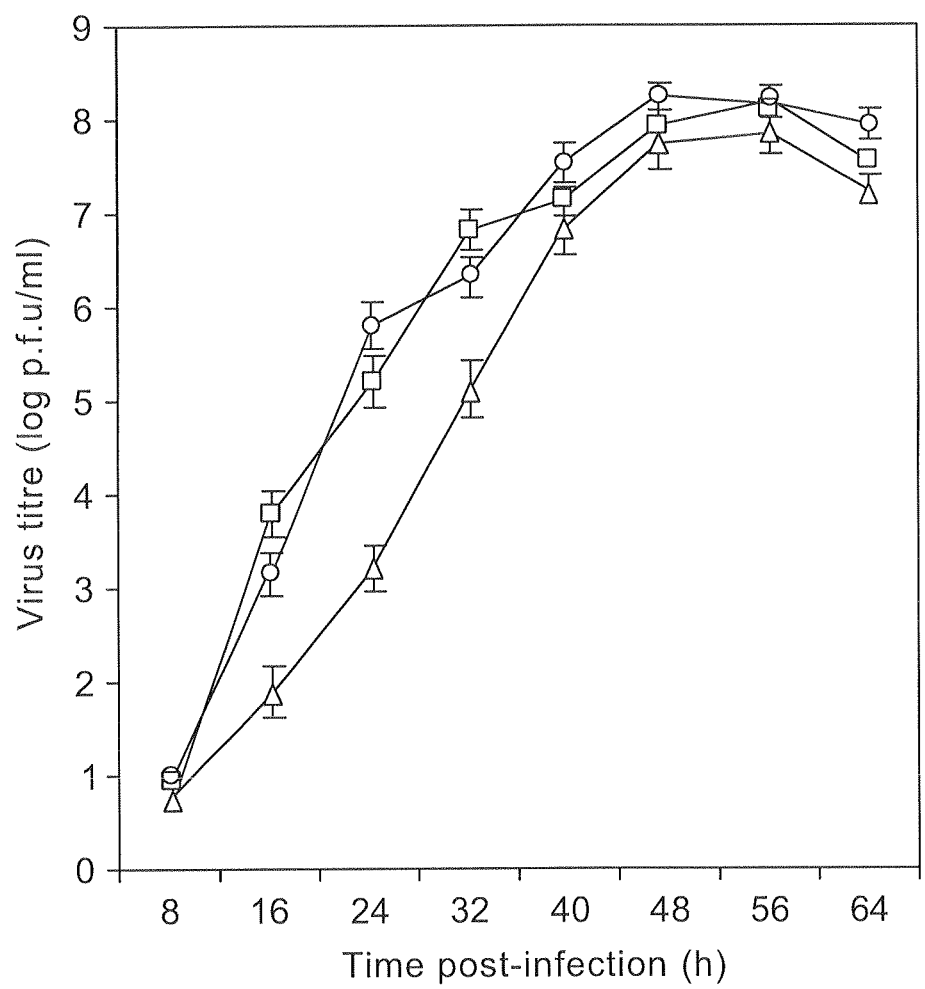
FIG. 9 shows multi-step growth curves for wt LaSota (●), rLaSota (■) and rLaSota/CAT (▲) in DF1 cells. Cell monolayers in 25 cm2 flasks were infected with 0.005 p.f.u. per cell with three replicate flasks per virus. Samples were taken every 8 h for 56 h. The virus in the supernatant was titrated by plaque assay. The log titer was derived from the mean virus titer and error bars indicate standard deviations.

The efficiency of replication in tissue culture of rLaSota, rLaSota/CAT and wild-type NDV LaSota was compared in a multiple-step growth cycle. Triplicate monolayers of DF1 cells were infected with each virus at an m.o.i. of 0.005 and samples were collected at 8 h intervals. The virus titers of these samples were quantified by plaque assay (FIG. 9). Both the kinetics and the magnitude of replication of the three viruses were very similar. However, the production of rLaSota/CAT was delayed slightly compared with rLaSota and wild-type NDV strain LaSota.

C. Determination of the Intracerebral Pathogenicity Index (ICPI) in 1-Day-Old Chicks ICPI was used to determine the virulence of wild-type and recombinant NDVs in 1-day-old chicks. For each ICPI test, 15 1-day-old SPF chicks were used (ten birds for test and five birds for control). The inoculum consisted of fresh, infective allantoic fluid with an HA titer >24 (1:16) for the test birds and allantoic fluid from uninfected embryonated chicken eggs for control birds. Both inocula were diluted 1:10 in sterile PBS. Each bird was inoculated intracerebrally with 0.05 ml inoculum. The birds were observed for clinical signs and mortality every 24 h for a period of 8 days. The scoring and determination of ICPI were done according to the method described by Alexander (1997).

In order to compare the pathogenicity of rLaSota, rLaSota/CAT and wild-type NDV strain LaSota, ICPI tests in 1-day-old chicks were performed by scoring clinical signs and mortality. The most virulent NDV strains give indices close to 2.0, while avirulent viruses give values close to 0. In our experiment, the results of ICPI were 0.27 for wild-type NDV LaSota, 0.29 for rLaSota and 0.24 for rLaSota/CAT. These results show that the recombinant viruses were similar in virulence to wild-type NDV strain LaSota.

The results described here show that attenuated NDV can be used as a vaccine vector to express a foreign gene. Development of recombinant NDV as a vaccine vector has several applications. Several foreign genes can be inserted and expressed in the same virus to obtain simultaneous immune responses to the expressed antigens in inoculated animals. For example, a single recombinant NDV could be generated that expressed the immunogenic proteins of multiple avian pathogens. Alternatively, several NDVs, each expressing various heterologous antigens, could be administered as a multivalent vaccine. A further extension would be to use NDV vectors in non-avian species, where NDV is capable of undergoing incomplete replication to the extent necessary to express inserted genes. Thus, development of NDV as a vector should prove to be useful against avian and non-avian diseases for which suitable vaccines are not currently available.

Example 4

A recombinant cDNA to the genome of NDV strain Beaudette C having a foreign gene, a gene encoding green fluorescent protein (GFP), inserted between P and M genes was prepared by inserting the GFP gene into the noncoding region of P gene after the P gene ORF and stop codon, but before the P gene GE signal (see FIG. 16). To allow the ORF of the GFP gene to be inserted into the noncoding region of the P gene, a XbaI site was created via mutation of a TCTCGC segment (nucleotide positions 3182-3187) in the P gene noncoding region after a stop codon forming a TCTAGA segment. The ORF of the GFP gene was preceded by a cDNA segment, TTAGAAAAAA, (SEQ ID NO: 19) for a NDV gene end signal followed by a cDNA segment, ACGGGTAGAA, (SEQ ID NO: 20) for a NDV gene start signal. Transcription of a plasmid containing the recombinant cDNA to the NDV Beaudette C genome carrying the GFP gene inserted into the noncoding region of the P gene resulted in a recombinant NDV which was found to be able to express GFP.

REFERENCES

Alexander, D. J. (1997). Newcastle disease and other avian Paramyxoviridae infections. In *Diseases of Poultry*, 10th edition, pp. 541-569. Edited by B. W. Calnek, Iowa State University Press, Ames, Iowa.

Byrappa, S., Gavin, D. K. & Gupta, K. C. (1995). A highly efficient procedure for site-specific mutagenesis of full-length plasmids using Vent DNA polymerase. Genome Research 5, 404-407.

Conzelmann, K.-K. (1996). Genetic manipulation of non-segmented negative-strand RNA viruses. Journal of General Virology 77, 381-389.

de Leeuw, O. & Peeters, B. (1999). Complete nucleotide sequence of Newcastle disease virus: evidence for the existence of a new genus within the subfamily Paramyxovirinae. Journal of General Virology 80, 131-136.

Kingsbury, D. W. (1966). Newcastle disease virus. I. Isolation and preliminary characterization of RNA from virus particles. Journal of Molecular Biology 18, 195-203.

Krishnamurthy, S. & Samal, S. K. (1998). Nucleotide sequences of the trailer, nucleocapsid protein gene and intergenic regions of Newcastle disease virus strain Beaudette C and completion of the entire genome sequence. Journal of General Virology 79, 2419-2424.

Peeters, B. P., de Leeuw, O. S., Koch, G. & Gielkens, A. L. (1999). Rescue of Newcastle disease virus from cloned cDNA: evidence that cleavability of the fusion protein is a major determinant for virulence. Journal of Virology 73, 5001-5009.

Phillips, R. J., Samson, A. R. & Emmerson, P. T. (1998). Nucleotide sequence of the 5'-terminus of Newcastle disease virus and assembly of the complete genomic sequence: agreement with the 'rule of six'. Archives of Virology 143, 1993-2002.

Römer-Oberdörfer, A., Mundt, E., Mebatsion, T., Buchholz, U. J. & Mettenleiter, T. C. (1999). Generation of recombinant lentogenic Newcastle disease virus from cDNA. Journal of General Virology 80, 2987-2995.

Steward, M., Vipond, I. B., Millar, N. S. & Emmerson, P. T. (1993). RNA editing in Newcastle disease virus. Journal of General Virology 74, 2539-2547.

TABLE 1

Oligonucleotide primers used for RT-PCR and assembly of full-length cDNA
(Sense: SEQ ID NOS: 27-33, respectively in order of appearance and Antisense:
SEQ ID NOS: 34-40, respectively in order of appearance)

| cDNA fragment | Primer Sense | Antisense | Order of cloning |
|---|---|---|---|
| I | 5' CTGAGGCGCGCCTAATACGACTCACTATAGGACCAAACAGAGAATCCGTGAGTTAG 3' | 5' GTTTCCGCGGCTGGGTTGACTCCCCT 3' | 4 |
| II | 5' GGTGCCGCGGAAACAGCCAGG 3' | 5' GAGCTGCGGCCGCTGTTATTTG 3' | 6 |
| III | 5' AACAGCGGCCGCAGCTCTGAT 3' | 5' TACAACGCGTAGTTTTTTCTTAACTC 3' | 7 |
| IV | 5' AACTACGCGTTGTAGATGACCAAAG 3' | 5' GCACTACGTATTTTGCCTTGTATCTC 3' | 5 |
| V | 5' CAAAATACGTAATGGTAAATAATACGGGTAGGACATG 3' | 5' TTCAGCTTAGCGAAGATCCGTCCATTAACT 3' | 3 |
| VI | 5' TTCAGCTAAGCTGACAAAGAAGTTAAGGAACTG 3' | 5' GTCTAGGCCTCTTACTCTCAGGTAATAG 3' | 1 |
| VII | 5' TCAGAGGCCTAGACAATATTGTCT 3' | 5' GATCCGGACCGcgaggaggtggagatgcccatgccgACCAAACAAAGATTTGGTGAATGACGAG 3' | 2 |

TABLE 2

Oligonucleotide Primers Used during Full-length cDNA Synthesis and RT-PCR (SEQ ID NOS 41-50, 32, 51-53, 53 and 54, respectively in order of appearance)

| cDNA fragments | Primers | Order of cloning |
|---|---|---|
| I | + 5'ACTGGGGCGCGCCTAATACGACTCACTATAGGACCAAACAGAGAATCCGTAAGTTAG3'<br>− 5'AGACCCGCGGCTGGGTTGACTTCCCTG3' | 8 |
| II | + 5'AGACCCGCGGAAACAGCCAGG3'<br>− 5'GCAGGGGCCCATCTTGCACCTAGAA3' | 7 |
| III | + 5'ACAGGGGCCCCAGACCTTCTACCAA3'<br>− 5'ATCGACGCGTAGTTTTTTCTAAACTCTC3' | 6 |
| IV | + 5'ATCGACGCGTTGTAGATGACCAAAG3'<br>− 5'GCACACCGGTAGCTGTTTTGCCTTGTATC3' | 5 |
| V | + 5'GCACACCGGTAAATAGTACGGGTAGGACATG3'<br>− 5'TTCAGCTTAGCGAAGATCCGTCCATTAAGT3' | 2 |
| VI | + 5'TTCAGCTAAGCTGACAAAGAAGTTAAGGAACTG3'<br>− 5'AAGCCTTAAGAACAATGTTTGGGCTTGCAAC3' | 4 |
| VII | + 5'AAGCCTTAAGAAACATACGCAAAGAGTCCT3'<br>− 5'TCAGAGGCCTTCTTACTCTCAGATAATAGAG3' | 3 |
| VIII | − 5'TCAGAGGCCTTCTTACTCTCAGATAATAGAG3'<br>5'ATGCCGGACCGcgaggaggtggagatgccatgccgACCCACCAAACAAAGATTTGGTGAATAACAAG3' | 1 |

TABLE 3

LASO_CAT.TXT (SEQ ID NO: 55)

ACCAAACAGAGAATCCGTGAGTTACGATAAAAGGCGAAAGAGCAATTGA
AGTCGCACGGGTAGAAGGTGTGAATCTCGAGTGCGAGCCCGAAGCACAA
ACTCGAGAAAGCCTTCTGCCAACGTTTAAACATGGAGAAAAAATCACT
GGATATACCACCGTTGATATATCCCAATGGCATCGTAAAGAACATTTTG
AGGCATTTCAGTCAGTTGCTCAATGTACCTATAACCAGACCGTTCAGCT
GGATATTACGGCCTTTTTAAAGACCGTAAAGAAAAATAAGCACAAGTTT
TATCCGGCCTTTATTCACATTCTTGCCCGCCTGATGAATGCTCATCCGG
AATTCCGTATGGCAATGAAAGACGGTGAGCTGGTGATATGGGATAGTGT
TCACCCTTGTTACACCGTTTTCCATGAGCAAACTGAAACGTTTTCATCG
CTCTGGAGTGAATACCACGACGATTTCCGGCAGTTTCTACACATATATT
CGCAAGATGTGGCGTGTTACGGTGAAAACCTGGCCTATTTCCCTAAAGG
GTTTATTGAGAATATGTTTTTCGTCTCAGCCAATCCCTGGGTGAGTTTC
ACCAGTTTTGATTTAAACGTGGCCAATATGGACAACTTCTTCGCCCCCG
TTTTCACCATGGGCAAATACTATACGCAAGGCGACAAGGTGCTGATGCC
GCTGGCGATTCAGGTTCATCATGCCGTTTGTGATGGCTTCCATGTCGGC
AGAATGCTTAATGAATTACAACAGTACTGCGATGAGTGGCAGGGCGGGG
CGTAACTGCAGATTAGAAAAAACACGGGTAGAAGTTTAAACTAGGTGCA
AGATGTCTTCCGTATTTGATGAGTACGAACAGCTCCTCGCGGCTCAGAC
TCGCCCCAATGGAGCTCATGGAGGGGGAGAAAAAGGGAGTACCTTAAAA
GTAGACGTCCCGGTATTCACTCTTAACAGTGATGACCCAGAAGATAGAT
GGAGCTTTGTGGTATTCTGCCTCCGGATTGCTGTTAGCGAAGATGCCAA
CAAACCACTCAGGCAAGGTGCTCTCATATCTCTTTTATGCTCCCACTCA
CAGGTAATGAGGAACCATGTTGCCCTTGCAGGGAAACAGAATGAAGCCA
CATTGGCCGTGCTTGAGATTGATGGCTTTGCCAACGGCACGCCCCAGTT
CAACAATAGGAGTGGAGTGTCTGAAGAGAGACACAGAGATTTGCGATG
ATAGCAGGATCTCTCCCTCGGGCATGCAGCAACGGAACCCCGTTCGTCA
CAGCCGGGGCCGAAGATGATGCACCAGAAGACATCACCGATACCCTGGA
GAGGATCCTCTCTATCCAGGCTCAAGTATGGGTCACAGTAGCAAAAGCC
ATGACTGCGTATGAGACTGCAGATGAGTCGGAAACAAGGCGAATCAATA
AGTATATGCAGCAAGGCAGGGTCCAAAAGAAATACATCCTCTACCCCGT
ATGCAGGAGCACAATCCAACTCACGATCAGACAGTCTCTTGCAGTCCGC
ATCTTTTTGGTTAGCGAGCTCAAGAGAGGCCGCAACACGGCAGGTGGTA
CCTCTACTTATTATAACCTGGTAGGGGACGTAGACTCATACATCAGGAA
TACCGGGCTTACTGCATTCTTCTTGACACTCAAGTACGGAATCAACACC
AAGACATCAGCCCTTGCACTTAGTAGCCTCTCAGGCGACATCCAGAAGA
TGAAGCAGCTCATGCGTTTGTATCGGATGAAAGGAGATAATGCGCCGTA
CATGACATTACTTGGTGATAGTGACCAGATGAGCTTTGCGCCTGCCGAG
TATGCACAACTTTACTCCCTTGCCATGGGTATGGCATCAGTCCTAGATA
AAGGTACTGGGAAATACCAATTTGCCAGGGACTTTATGAGCACATCATT
CTGGAGACTTGGAGTAGAGTACGCTCAGGCTCAGGGAAGTAGCATTAAC
GAGGATATGGCTGCCGAGCTAAAGCTAACCCCAGCAGCAAGGAGGGGCC
TGGCAGCTGCTGCCCAACGGGTCTCCGAGGAGACCAGCAGCATAGACAT
GCCTACTCAACAAGTCGGAGTCCTCACTGGGCTTAGCGAGGGGGGGTCC
CAAGCTCTACAAGGCGGATCGAATAGATCGCAAGGGCAACCAGAAGCCG
GGGATGGGGAGACCCAATTCCTGGATCTGATGAGAGCGGTAGCAAATAG
CATGAGGGAGGCGCCAAACTCTGCACAGGGCACTCCCCAATCGGGGCCT
CCCCCAACTCCTGGGCCATCCCAAGATAACGACACCGACTGGGGTATT
GATGGACAAAACCCAGCCTGCTTCCACAAAAACATCCCAATGCCCTCAC
CCGTAGTCGACCCCTCGATTTGCGGCTCTATATGACCACACCCTCAAAC
AAACATCCCCCTCTTTCCTCCCTCCCCTGCTGTACAACTCCGCACGCC
CTAGATACCACAGGCACAATGCGGCTCACTAACAATCAAAACAGAGCCG
AGGGAATTAGAAAAAGTACGGGTAGAAGAGGGATATTCAGAGATCAGG
GCAAGTCTCCCGAGTCTCTGCTCTCTCCTCTACCTGATAGACCAGGACA
AACATGGCCACCTTTACAGATGCAGAGATCGACGAGCTATTTGAGACAA
GTGGAACTGTCATTGACAACATAATTACAGCCCAGGGTAAACCAGCAGA
GACTGTTGGAAGGAGTGCAATCCCACAAGGCAAGACCAAGGTGCTGAGC
GCAGCATGGGAGAAGCATGGGAGCATCCAGCCACCGGCCAGTCAAGACA
ACCCCGATCGACAGGACAGATCTGACAAACAACCATCCACACCCGAGCA
AACGACCCCGCATGACAGCCCGCCGGCCACATCCGCCGACCAGCCCCCC
ACCCAGGCCACAGACGAAGCCGTCGACACACAGCTCAGGACGGAGCAA
GCAACTCTCTGCTGTTGATGCTTGACAAGCTCAGCAATAAATCGTCCAA
TGCTAAAAAGGGCCCATGGTCGAGCCCCAAGAGGGGAATCACCAACGT
CCGACTCAACAGCAGGGGAGTCAACCCAGCCGCGGAAACAGTCAGGAAA
GACCGCAGAACCAAGTCAAGGCCGCCCCTGGAAACCAGGGCACAGACGT
GAACACAGCATATCATGGACAATGGGAGGAGTCACAACTATCAGCTGGT
GCAACCCCTCATGCTCTCCGATCAAGGCAGAGCCAAGACAATACCCTTG
TATCTGCGGATCATGTCCAGCCACCTGTAGACTTTGTGCAAGCGATGAT
GTCTATGATGGAGGCGATATCACAGAGAGTAAGTAAGGTCGACTATCAG
CTAGATCTTGTCTTGAAACAGACATCCTCCATCCCTATGATGCGGTCCG
AAATCCAACAGCTGAAAACATCTGTTGCAGTCATGGAAGCCAACTTGGG
AATGATGAAGATTCTGGATCCCGGTTGTGCCAACATTTCATCTCTGAGT
GATCTACGGGCAGTTGCCCGATCTCACCCGGTTTTAGTTTCAGGCCCTG
GAGACCCCTCTCCCTATGTGACAAGGAGGCGAAATGGCACTTAATAA
ACTTTCGCAACCAGTGCCACATCCATCTGAATTGATTAAACCCGCCACT
GCATGCGGGCCTGATATAGGAGTGGAAAAGGACACTGTCCGTGCATTGA
TCATGTCACGCCCAATGCACCCGAGTTCTTCAGCCAAGCTCCTAAGCAA
GTTAGATGCAGCCGGGTCGATCGAGGAAATCAGGAAAATCAAGCGCCTT
GCTCTAAATGGCTAATTACTACTGCCACACGTAGCGGGTCCCTGTCCAC

TABLE 3-continued

LASO_CAT.TXT (SEQ ID NO: 55)

TCGGCATCACACGGAATCTGCACCGAGTTCCCCCCCGCAGACCCAAGGT
CCAACTCTCCAAGCGGCAATCCTCTCTCGCTTCCTCAGCCCCACTGAAT
GGTCGCGTAACCGTAATTAATCTAGCTACATTTAAGATTAAGAAAAAT
ACGGGTAGAATTGGAGTGCCCCAATTGTGCCAAGATGGACTCATCTAGG
ACAATTGGGCTGTACTTTGATTCTGCCCATTCTTCTAGCAACCTGTTAG
CATTTCCGATCGTCCTACAAGGCACAGGAGATGGGAAGAAGCAAATCGC
CCCGCAATATAGGATCCAGCGCCTTGACTTGTGGACTGATAGTAAGGAG
GACTCAGTATTCATCACCACCTATGGATTCATCTTTCAAGTTGGGAATG
AAGAAGCCACTGTCGGCATGATCGATGATAAACCCAAGCGCGAGTTACT
TTCCGCTGCGATGCTCTGCCTAGGAAGCGTCCCAAATACCGGAGACCTT
ATTGAGCTGGCAAGGGCCTGTCTCACTATGATAGTCACATGCAAGAAGA
GTGCAACTAATACTGAGAGAATGGTTTTCTCAGTAGTGCAGGCACCCCA
AGTGCTGCAAAGCTGTAGGGTTGTGGCAAACAATACTCATCAGTGAAT
GCAGTCAAGCACGTGAAAGCGCCAGAGAAGATTCCCGGGAGTGGAACCC
TAGAATACAAGGTGAACTTTGTCTCCTTGACTGTGGTACCGAAGAAGGA
TGTCTACAAGATCCCTGCTGCAGTATTGAAGGTTTCTGGCTCGAGTCTG
TACAATCTTGCGCTCAATGTCACTATTAATGTGGAGGTAGACCCGAGGA
GTCCTTTGGTTAAATCTCTGTCTAAGTCTGACAGCGGATACTATGCTAA
CCTCTTCTTGCATATTGGACTTATGACCACCGTAGATAGGAAGGGGAAG
AAAGTGACATTTGACAAGCTGGAAAAGAAAATAAGGAGCCTTGATCTAT
CTGTCGGGCTCAGTGATGTGCTCGGGCCTTCCGTGTTGGTAAAAGCAAG
AGGTGCACGGACTAAGCTTTTGGCACCTTTCTTCTCTAGCAGTGGGACA
GCCTGCTATCCCATAGCAAATGCTTCTCCTCAGGTGGCCAAGATACTCT
GGAGTCAAACCGCGTGCCTGCGGAGCGTTAAAATCATTATCCAAGCAGG
TACCCAACGCGCTGTCGCAGTGACCGCCGACCACGAGGTTACCTCTACT
AAGCTGGAGAAGGGGCACACCCTTGCCAAATACAATCCTTTTAAGAAAT
AAGCTGCGTCTCTGAGATTGCGCTCCGCCCACTCACCCAGATCATCATG
ACACAAAAAACTAATCTGTCTTGATTATTTACAGTTAGTTTACCTGTCT
ATCAAGTTAGAAAAAACACGGGTAGAAGATTCTGGATCCCGGTTGGCGC
CCTCCAGGTGCAAGATGGGCTCCAGACCTTCTACCAAGAACCCAGCACC
TATGATGCTGACTATCCGGGTTGCGCTGGTACTGAGTTGCATCTGTCCG
GCAAACTCCATTGATGGCAGGCCTCTTGCAGCTGCAGGAATTGTGGTTA
CAGGAGACAAAGCCGTCAACATATACACCTCATCCCAGACAGGATCAAT
CATAGTTAAGCTCCTCCCGAATCTGCCCAAGGATAAGGAGGCATGTGCG
AAAGCCCCCTTGGATGCATACAACAGGACATTGACCACTTTGCTCACCC
CCCTTGGTGACTCTATCCGTAGGATACAAGAGTCTGTGACTACATCTGG
AGGGGGGAGACAGGGGCGCCTTATAGGCGCCATTATTGGCGGTGTGGCT
CTTGGGGTTGCAACTGCCGCACAAATAACAGCGGCCGCAGCTCTGATAC
AAGCCAAACAAAATGCTGCCAACATCCTCCGACTTAAAGAGAGCATTGC

CGCAACCAATGAGGCTGTGCATGAGGTCACTGACGGATTATCGCAACTA
GCAGTGGCAGTTGGGAAGATGCAGCAGTTTGTTAATGACCAATTTAATA
AAACAGCTCAGGAATTAGACTGCATCAAAATTGCACAGCAAGTTGGTGT
AGAGCTCAACCTGTACCTAACCGAATTGACTACAGTATTCGGACCACAA
ATCACTTCACCTGCTTTAAACAAGCTGACTATTCAGGCACTTTACAATC
TAGCTGGTGGAAATATGGATTACTTATTGACTAAGTTAGGTGTAGGGAA
CAATCAACTCAGCTCATTAATCGGTAGCGGCTTAATCACCGGTAACCCT
ATTCTATACGACTCACAGACTCAACTCTTGGGTATACAGGTAACTCTAC
CTTCAGTCGGGAACCTAAATAATATGCGTGCCACCTACTTGGAAACCTT
ATCCGTAAGCACAACCAGGGGATTTGCCTCGGCACTTGTCCCAAAAGTG
GTGACACAGGTCGGTTCTGTGATAGAAGAACTTGACACCTCATACTGTA
TAGAAACTGACTTAGATTTATATTGTACAAGAATAGTAACGTTCCCTAT
GTCCCCTGGTATTTATTCCTGCTTGAGCGGCAATACGTCGGCCTGTATG
TACTCAAAGACCGAAGGCGCACTTACTACACCATACATGACTATCAAAG
GTTCAGTCATCGCCAACTGCAAGATGACAACATGTAGATGTGTAAACCC
CCCGGGTATCATATCGCAAAACTATGGAGAAGCCGTGTCTCTAATAGAT
AAACAATCATGCAATGTTTTATCCTTAGGCGGGATAACTTTAAGGCTCA
GTGGGGAATTCGATGTAACTTATCAGAAGAATATCTCAATACAAGATTC
TCAAGTAATAATAACAGGCAATCTTGATATCTCAACTGAGCTTGGGAAT
GTCAACAACTCGATCAGTAATGCTTTGAATAAGTTAGAGGAAAGCAACA
GAAAACTAGACAAAGTCAATGTCAAACTGACCAGCACATCTGCTCTCAT
TACCTATATCGTTTTGACTATCATATCTCTTGTTTTTGGTATACTTAGC
CTGATTCTAGCATGCTACCTAATGTACAAGCAAAAGGCGCAACAAAAGA
CCTTATTATGGCTTGGGAATAATACCCTAGATCAGATGAGAGCCACTAC
AAAAATGTGAACACAGATGAGGAACGAAGGTTTCCCTAATAGTAATTTG
TGTGAAAGTTCTGGTAGTCTGTCAGTTCAGAGAGTTAAGAAAAAACTAC
GCGTTGTAGATGACCAAAGGACGATATACGGGTAGAACGGTAAGAGAGG
CCGCCCCTCAATTGCGAGCCAGGCTTCACAACCTCCGTTCTACCGCTTC
ACCGACAACAGTCCTCAATCATGGACCGCGCCGTTAGCCAAGTTGCGTT
AGAGAATGATGAAAGAGAGGCAAAAAATACATGGCGCTTGATATTCCGG
ATTGCAATCTTATTCTTAACAGTAGTGACCTTGGCTATATCTGTAGCCT
CCCTTTTATATAGCATGGGGGCTAGCACACCTAGCGATCTTGTAGGCAT
ACCGACTAGGATTTCCAGGGCAGAAGAAAAGATTACATCTACACTTGGT
TCCAATCAAGATGTAGTAGATAGGATATATAAGCAAGTGGCCCTTGAGT
CTCCGTTGGCATTGTTAAAAACTGAGACCACAATTATGAACGCAATAAC
ATCTCTCTCTTATCAGATTAATGGAGCTGCAAACAACAGTGGGTGGGGG
GCACCTATCCATGACCCAGATTATATAGGGGGGATAGGCAAAGAACTCA
TTGTAGATGATGCTAGTGATGTCACATCATTCTATCCCTCTGCATTTCA
AGAACATCTGAATTTTATCCCGGCGCCTACTACAGGATCAGGTTGCACT

TABLE 3-continued

LASO_CAT.TXT (SEQ ID NO: 55)

CGAATACCCTCATTTGACATGAGTGCTACCCATTACTGCTACACCCATA
ATGTAATATTGTCTGGATGCAGAGATCACTCACATTCATATCAGTATTT
AGCACTTGGTGTGCTCCGGACATCTGCAACAGGGAGGGTATTCTTTTCT
ACTCTGCGTTCCATCAACCTGGACGACACCCAAAATCGGAAGTCTTGCA
GTGTGAGTGCAACTCCCCTGGGTTGTATATGCTGTGCTCGAAAGTCAC
GGAGACAGAGGAAGAAGATTATAACTCAGCTGTCCCTACGCGGATGGTA
CATGGGAGGTTAGGGTTCGACGGCCAGTACCACGAAAAGGACCTAGATG
TCACAACATTATTCGGGGACTGGGTGGCCAACTACCCAGGAGTAGGGGG
TGGATCTTTTATTGACAGCCGCGTATGGTTCTCAGTCTACGGAGGGTTA
AAACCCAATTCACCCAGTGACACTGTACAGGAAGGGAAATATGTGATAT
ACAAGCGATACAATGACACATGCCCAGATGAGCAAGACTACCAGATTCG
AATGGCCAAGTCTTCGTATAAGCCTGGACGGTTTGGTGGGAAACGCATA
CAGCAGGCTATCTTATCTATCAAGGTGTCAACATCCTTAGGCGAAGACC
CGGTACTGACTGTACCGCCCAACACAGTCACACTCATGGGGGCCGAAG
GCAGAATTCTCACAGTAGGGACATCTCATTTCTTGTATCAACGAGGGTC
ATCATACTTCTCTCCCGCGTTATTATATCCTATGACAGTCAGCAACAAA
ACAGCCACTCTTCATAGTCCTTATACATTCAATGCCTTCACTCGGCCAG
GTAGTATCCCTTGCCAGGCTTCAGCAAGATGCCCCAACTCGTGTGTTAC
TGGAGTCTATACAGATCCCATATCCCCTAATCTTCTATAGAAACCACACC
TTGCGAGGGGTATTCGGGACAATGCTTGATGGTGTACAAGCAAGACTTA
ACCCTGCGTCTGCAGTATTCGATAGCACATCCCGCAGTCGCATTACTCG
AGTGAGTTCAAGCAGTACCAAAGCAGCATACACAACATCAACTTGTTTT
AAAGTGGTCAAGACTAATAAGACCTATTGTCTCAGCATTGCTGAAATAT
CTAATACTCTCTTCGGAGAATTCAGAATCGTCCCGTTACTAGTTGAGAT
CCTCAAAGATGACGGGGTTAGAGAAGCCAGGTCTGGCTAGTTGAGTCAA
TTATAAAGGAGTTGGAAAGATGGCATTGTATCACCTATCTTCTGCGACA
TCAAGAATCAAACCGAATGCCGGCGCGTGCTCGAATTCCATGTTGCCAG
TTGACCACAATCAGCCAGTGCTCATGCGATCAGATTAAGCCTTGTCATT
AATCTCTTGATTAAGAAAAAATGTAAGTGGCAATGAGATACAAGGCAAA
ATACGTACCGGTAAATAATACGGGTAGGACATGGCGAGCTCCGGTCCTG
AAAGGGCAGAGCATCAGATTATCCTACCAGAGCCACACCTGTCTTCACC
ATTGGTCAAGCACAAACTACTCTATTACTGGAAATTAACTGGGCTACCG
CTTCCTGATGAATGTGACTTCGACCACCTCATTCTCAGCCGACAATGGA
AAAAAATACTTGAATCGGCCTCTCCTGATACTGAGAGAATGATAAAACT
CGGAAGGGCAGTACACCAAACTCTTAACCACAATTCCAGAATAACCGGA
GTGCTCCACCCCAGGTGTTTAGAACAACTGGCTAATATTGAGGTCCCAG
ATTCAACCAACAAATTTCGGAAGATTGAGAAGAAGATCCAAATTCACAA
CACGAGATATGGAGAACTGTTCACAAGGCTGTGTACGCATATAGAGAAG
AAACTGCTGGGGTCATCTTGGTCTAACAATGTCCCCCGGTCAGAGGAGT
TCAGCAGCATTCGTACGGATCCGGCATTCTGGTTTCACTCAAAATGGTC
CACAGCCAAGTTTGCATGGCTCCATATAAAACAGATCCAGAGGCATCTG
ATGGTGGCAGCTAAGACAAGGTCTGCGGCCAACAAATTGGTGATGCTAA
CCCATAAGGTAGGCCAAGTCTTTGTCACTCCTGAACTTGTCGTTGTGAC
GCATACGAATGAGAACAAGTTCACATGTCTTACCCAGGAACTTGTATTG
ATGTATGCAGATATGATGGAGGGCAGAGATATGGTCAACATAATATCAA
CCACGGCGGTGCATCTCAGAAGCTTATCAGAGAAATTGATGACATTTT
GCGGTTAATAGACGCTCTGGCAAAAGACTTGGGTAATCAAGTCTACGAT
GTTGTATCACTAATGGAGGGATTTGCATACGGAGCTGTCCAGCTACTCG
AGCCGTCAGGTACATTTGCAGGAGATTTCTTCGCATTCAACCTGCAGGA
GCTTAAAGACATTCTAATTGGCCTCCTCCCCAATGATATAGCAGAATCC
GTGACTCATGCAATCGCTACTGTATTCTCTGGTTTAGAACAGAATCAAG
CAGCTGAGATGTTGTGTCTGTTGCGTCTGTGGGGTCACCCACTGCTTGA
GTCCCGTATTGCAGCAAAGGCAGTCAGGAGCCAAATGTGCGCACCGAAA
ATGGTAGACTTTGATATGATCCTTCAGGTACTGTCTTTCTTCAAGGGAA
CAATCATCAACGGGTACAGAAAGAAGAATGCAGGTGTGTGGCCGCGAGT
CAAAGTGGATACAATATATGGGAAGGTCATTGGGCAACTACATGCAGAT
TCAGCAGAGATTTCACACGATATCATGTTGAGAGAGTATAAGAGTTTAT
CTGCACTTGAATTTGAGCCATGTATAGAATATGACCCTGTCACCAACCT
GAGCATGTTCCTAAAAGACAAGGCAATCGCACACCCCAACGATAATTGG
CTTGCCTCGTTTAGGCGGAACCTTCTCTCCGAAGACCAGAAGAAACATG
TAAAAGAAGCAACTTCGACTAATCGCCTCTTGATAGAGTTTTTAGAGTC
AAATGATTTTGATCCATATAAAGAGATGGAATATCTGACGACCCTTGAG
TACCTTAGAGATGACAATGTGGCAGTATCATACTCGCTCAAGGAGAAGG
AAGTGAAAGTTAATGGACGGATCTTCGCTAAGCTGACAAAGAAGTTAAG
GAACTGTCAGGTGATGGCGGAAGGGATCCTAGCCGATCAGATTGCACCT
TTCTTTCAGGGAAATGGAGTCATTCAGGATAGCATATCCTTGACCAAGA
GTATGCTAGCGATGAGTCAACTGTCTTTTAACAGCAATAAGAAACGTAT
CACTGACTGTAAAGAAAGAGTATCTTCAAACCGCAATCATGATCCGAAA
AGCAAGAACCGTCGGAGAGTTGCAACCTTCATAACAACTGACCTGCAAA
AGTACTGTCTTAATTGGAGATATCAGACAATCAAATTGTTCGCTCATGC
CATCAATCAGTTGATGGGCCTACCTCACTTCTTCGAATGGATTCACCTA
AGACTGATGGACACTACGATGTTCGTAGGAGACCCTTTCAATCCTCCAA
GTGACCCTACTGACTGTGACCTCTCAAGAGTCCCTAATGATGACATATA
TATTGTCAGTGCCAGAGGGGGTATCGAAGGATTATGCCAGAAGCTATGG
ACAATGATCTCAATTGCTGCAATCCAACTTGCTGCAGCTAGATCGCATT
GTCGTGTTGCCTGTATGGTACAGGGTGATAATCAAGTAATAGCAGTAAC
GAGAGAGGTAAGATCAGACGACTCTCCGGAGATGGTGTTGACACAGTTG
CATCAAGCCAGTGATAATTTCTTCAAGGAATTAATTCATGTCAATCATT

TABLE 3-continued

LASO_CAT.TXT (SEQ ID NO: 55)

TGATTGGCCATAATTTGAAGGATCGTGAAACCATCAGGTCAGACACATT
CTTCATATACAGCAAACGAATCTTCAAAGATGGAGCAATCCTCAGTCAA
GTCCTCAAAAATTCATCTAAATTAGTGCTAGTGTCAGGTGATCTCAGTG
AAAACACCGTAATGTCCTGTGCCAACATTGCCTCTACTGTAGCACGGCT
ATGCGAGAACGGGCTTCCCAAAGACTTCTGTTACTATTTAAACTATATA
ATGAGTTGTGTGCAGACATACTTTGACTCTGAGTTCTCCATCACCAACA
ATTCGCACCCCGATCTTAATCAGTCGTGGATTGAGGACATCTCTTTTGT
GCACTCATATGTTCTGACTCCTGCCCAATTAGGGGGACTGAGTAACCTT
CAATACTCAAGGCTCTACACTAGAAATATCGGTGACCCGGGGACTACTG
CTTTTGCAGAGATCAAGCGACTAGAAGCAGTGGGATTACTGAGTCCTAA
CATTATGACTAATATCTTAACTAGGCCGCCTGGGAATGGAGATTGGGCC
AGTCTGTGCAACGACCCATACTCTTTCAATTTTGAGACTGTTGCAAGCC
CAAATATTGTTCTTAAGAAACATACGCAAAGAGTCCTATTTGAAACTTG
TTCAAATCCCTTATTGTCTGGAGTGCACACAGAGGATAATGAGGCAGAA
GAGAAGGCATTGGCTGAATTCTTGCTTAATCAAGAGGTGATTCATCCCC
GCGTTGCGCATGCCATCATGGAGGCAAGCTCTGTAGGTAGGAGAAAGCA
AATTCAAGGGCTTGTTGACACAACAAAACACCGTAATTAAGATTGCGCTT
ACTAGGAGGCCATTAGGCATCAAGAGGCTGATGCGGATAGTCAATTATT
CTAGCATGCATGCAATGCTGTTTAGAGACGATGTTTTTTCCTCCAGTAG
ATCCAACCACCCCTTAGTCTCTTCTAATATGTGTTCTCTGACACTGGCA
GACTATGCACGGAATAGAAGCTGGTCACCTTTGACGGGAGGCAGGAAAA
TACTGGGTGTATCTAATCCTGATACGATAGAACTCGTAGAGGGTGAGAT
TCTTAGTGTAAGCGGAGGGTGTACAAGATGTGACAGCGGAGATGAACAA
TTTACTTGGTTCCATCTTCCAAGCAATATAGAATTGACCGATGACACCA
GCAAGAATCCTCCGATGAGGGTACCATATCTCGGGTCAAAGACACAGGA
GAGGAGAGCTGCCTCACTTGCAAAAATAGCTCATATGTCGCCACATGTA
AAGGCTGCCCTAAGGGCATCATCCGTGTTGATCTGGGCTTATGGGGATA
ATGAAGTAAATTGGACTGCTGCTCTTACGATTGCAAAATCTCGGTGTAA
TGTAAACTTAGAGTATCTTCGGTTACTGTCCCCTTTACCCACGGCTGGG
AATCTTCAACATAGACTAGATGATGGTATAACTCAGATGACATTCACCC
CTGCATCTCTCTACAGGTGTCACCTTACATTCACATATCCTAATGATTC
TCAAAGGCTGTTCACTGAAGAAGGAGTCAAAGAGGGGAATGTGGTTTAC
CAACAGAGTCATGCTCTTGGGTTTATCTCTAATCGAATCGATCTTTCCA
CTACATAGTAAATTTAGTTGCTGTATCAGAGAAGCACCATGACAACAAC
CAGGACATATGATGAGATCACACTGCACTGTTGCGGTTCCTTTCGAGCT
ACTTGGGGTGGTACCGGAACTGAGGACAGTGACCTCAAATAAGTTTATG
TATGATCCTAGCCCTGTATCGGAGGGAGACTTTGCGAGACTTGACTTAG
CTATCTTCAAGAGTTATGAGCTTAATCTGGAGTCATATCCCACGATAGA
GCTAATGAACATTCTTTCAATATCCAGCGGGAAGTTGATTGGCCAGTCT
GTGGTTTCTTATGATGAAGATACCTCCATAAAGAATGACGCCATAATAG
TGTATGACAATACCCGAAATTGGATCAGTGAAGCTCAGAATTCAGATGT
GGTCCGCCTATTTGAATATGCAGCACTTGAAGTGCTCCTCGACTGTTCT
TACCAACTCTATTACCTGAGAGTAAGAGGCCTAGACAATATTGTCTTAT
ATATGGGTGATTTATACAAGAATATGCCAGGAATTCTACTTTCCAACAT
TGCAGCTACAATATCTCATCCCGTCATTCATTCAAGGTTACATGCAGTG
GGCCTGGTCAACCATGACGGATCACACCAACTTGCAGATACGGATTTTA
TCGAAATGTCTGCAAAACTATTAGTATCTTGCACCCGACGTGTGATCTC
CGGCTTATATTCAGGAAATAAGTATGATCTGCTGTTCCCATCTGTCTTA
GATGATAACCTGAATGAGAAGATGCTTCAGCTGATATCCCGGTTATGCT
GTCTGTACACGGTACTCTTTGCTACAACAAGAGAAATCCCGAAAATAAG
AGGCTTAACTGCAGAAGAGAAATGTTCAATACTCACTGAGTATTTACTG
TCGGATGCTGTGAAACCATTACTTAGCCCCGATCAAGTGAGCTCTATCA
TGTCTCCTAACATAATTACATTCCCAGCTAATCTGTACTACATGTCTCG
GAAGAGCCTCAATTTGATCAGGGAAAGGGAGGACAGGGATACTATCCTG
GCGTTGTTGTTCCCCAAGAGCCATTATTAGAGTTCCCTTCTGTGCAAG
ATATTGGTGCTCGAGTGAAAGATCCATTCACCCGACAACCTGCGGCATT
TTTGCAAGAGTTAGATTTGAGTGCTCCAGCAAGGTATGACGCATTCACA
CTTAGTCAGATTCATCCTGAACTCACATCTCCAAATCCGGAGGAAGACT
ACTTAGTACGATACTTGTTCAGAGGGATAGGGACTGCATCTTCCTCTTG
GTATAAGGCATCTCATCTCCTTTCTGTACCCGAGGTAAGATGTGCAAGA
CACGGGAACTCCTTATACTTAGCTGAAGGGAGCGGAGCCATCATGAGTC
TTCTCGAACTGCATGTACCACATGAAACTATCTATTACAATACGCTCTT
TTCAAATGAGATGAACCCCCCGCAACGACATTTCGGGCCGACCCCAACT
CAGTTTTTGAATTCGGTTGTTTATAGGAATCTACAGGCGGAGGTAACAT
GCAAAGATGGATTTGTCCAAGAGTTCCGTCCATTATGGAGAGAAAATAC
AGAGGAAAGTGACCTGACCTCAGATAAAGCAGTGGGGTATATTACATCT
GCAGTGCCCTACAGATCTGTATCATTGCTGCATTGTGACATTGAAATTC
CTCCAGGGTCCAATCAAAGCTTACTAGATCAACTAGCTATCAATTTATC
TCTGATTGCCATGCATTCTGTAAGGGAGGCGGGGTAGTAATCATCAAA
GTGTTGTATGCAATGGGATACTACTTTCATCTACTCATGAACTTGTTTG
CTCCGTGTTCCACAAAAGGATATATTCTCTAATGGTTATGCATGTCG
AGGAGATATGGAGTGTTACCTGGTATTTGTCATGGGTTACCTGGGCGGG
CCTACATTTGTACATGAGGTGGTGAGGATGGCAAAAACTCTGGTGCAGC
GGCACGGTACGCTCTTGTCTAAATCAGATGAGATCACACTGACCAGGTT
ATTCACCTCACAGCGGCAGCGTGACAGACATCCTATCCAGTCCTTTA
CCAAGATTAATAAAGTACTTGAGGAAGAATATTGACACTGCGCTGATTG
AAGCCGGGGACAGCCCGTCCGTCCATTCTGTGCGGAGAGTCTGGTGAG
CACGCTAGCGAACATAACTCAGATAACCCAGATTATCGCTAGTCACATT

TABLE 3-continued

LASO_CAT.TXT (SEQ ID NO: 55)

GACACAGTTATCCGGTCTGTGATATATATGGAAGCTGAGGGTGATCTCG

CTGACACAGTATTTCTATTTACCCCTTACAATCTCTCTACTGACGGGAA

AAAGAGGACATCACTTATACAGTGCACGAGACAGATCCTAGAGGTTACA

ATACTAGGTCTTAGAGTCGAAAATCTCAATAAAATAGGCGATATAATCA

GCCTAGTGCTTAAAGGCATGATCTCCATGGAGGACCTTATCCCACTAAG

GACATACTTGAAGCATAGTACCTGCCCTAAATATTTGAAGGCTGTCCTA

GGTATTACCAAACTCAAAGAAATGTTTACAGACACTTCTGTATTGTACT

TGACTCGTGCTCAACAAAAATTCTACATGAAAACTATAGGCAATGCAGT

CAAAGGATATTACAGTAACTGTGACTCTTAACGAAAATCACATATTAAT

AGGCTCCTTTTTTGGCCAATTGTATTCTTGTTGATTTAATCATATTATG

TTAGAAAAAAGTTGAACCCTGACTCCTTAGGACTCGAATTCGAACTCAA

ATAAATGTCTTAAAAAAGGTTGCGCACAATTATTCTTGAGTGTAGTCT

CGTCATTCACCAAATCTTTGTTTGGT

TABLE 4

BC_CAT_.TXT (SEQ ID NO: 56)

ACCAAACAGAGAATCCGTAAGTTACGATAAAAGGCGAAGGAGCAATTGA

AGTTGCACGGGTAGAAGGTGTGAATCTCGAGTGCGAGCCCGAAGCACAA

ACTCGAGAAAGCCTTCTGCCAACATGTCTTCCGTATTTGACGAGTACGA

ACAGCTCCTCGCGGCTCAGACTCGCCCCAATGGAGCTCATGGAGGAGGG

GAAAAGGGGAGTACCTTAAAAGTAGACGTCCCGGTATTCACTCTTAACA

GTGATGACCCAGAAGATAGGTGGAACTTTGCGGTATTCTGCCTCCGGAT

TGCTGTTAGCGAAGATGCCAACAAACCACTCAGGCAAGGTGCTCTCATA

TCTCTTTTATGCTCCCACTCACAAGTGATGAGGAACCATGTTGCCCTTG

CAGGGAAACAGAATGAAGCCACATTGGCCGTGCTTGAGATTGATGGCTT

TGCCAACGGTATGCCCCAGTTCAACAATAGGAGTGGAGTGTCTGAAGAG

AGAGCACAGAGATTCGCGATGATAGCAGGGTCTCTCCCTCGGGCATGCA

GTAATGGCACCCCGTTCGTCACAGCCGGGGCCGAAGATGATGCACCAGA

AGATATCACCGATACCCTGGAGAGGATCCTCTCTATCCAGGCCCAAGTA

TGGGTCACAGTAGCAAAAGCCATGACTGCGTATGAGACTGCAGATGAGT

CTGAAACAAGACGAATCAGTAAGTATATGCAGCAAGGCAGGGTCCAAAA

GAAATACATCCTCTACCCCGTATGCAGGAGCACAATCCAACTCACGATC

AGACAGTCTCTTGCAGTCCGCATCTTTTTGGTTAGCGAGCTCAAGAGAG

GCCGCAACACGGCAGGTGGTACCTCTACTTATTATAACCTAGTAGGGGA

CGTAGACTCATATATCAGGAATACCGGGCTTACTGCATTCTTCTTGACA

CTCAAGTACGGAATTAACACCAAGACATCAGCCCTTGCACTTAGTAGCC

TCTCAGGCGACATCCAGAAAATGAAGCAGCTCATGCGTTTATATCGGAT

GAAAGGAGATAATGCGCCGTACATGACATTGCTTGGTGATAGTGACCAG

ATGAGCTTTGCGCCTGCCGAGTATGCACAACTTTACTCCTTCGCCATGG

TABLE 4-continued

BC_CAT_.TXT (SEQ ID NO: 56)

GTATGGCATCAGTCCTAGATAAAGGTACTGGGAAATACCAATTTGCCAG

GGACTTTATGAGCACATCATTCTGGAGACTTGGAGTAGAGTACGCTCAG

GCTCAGGGAAGTAGCATTAACGAGGATATGGCTGCCGAGCTAAAGTTAA

CCCCAGCAGCAAGGAGAGGCCTGGCAGCTGCTGCCCAACGAGTCTCTGA

GGAGACCAGCAGCATAGACATGCCTACTCAACAAGTCGGAGTCCTCACT

GGGCTCAGCGAGGGGGGGTCCCAAGCCCTACAAGGCGGATCGAATAGAT

CGCAAGGGCAACCAGAAGCCGGGGATGGGGAGACCCAATTCCTGGATCT

GATGAGAGCGGTAGCAAATAGCATGAGGGAAGCGCCAAACTCTGCACAG

GGCACTCCCCAATCGGGGCCTCCCCCAACTCCTGGGCCATCTCAAGATA

ACGACACCGACTGGGGGTATTGATTGACAAAACCCAGCTTGCTTCCACA

AAATCATCCCAATATCCTCACCCGTAGTCGACCCCTCGATTTGCGGCCC

TATATGACCACACCCACAAACAAACATCCCCCTCTTTCCTCCCTCCCCC

TGCTGTACAACTCCGCACGCCCTAGGTACCACAGGCACAATGCGGCTCA

CTAACAATCAAAACAGAGCCGAGGAAATTAGAAAAAAATACGGGTAGAA

GAGGGATATTCAGAGACCAGGGCAAGTCACCCGAGTCTCTGCTCTCTCC

TCTACCTGATAGATTAGGACAAATATGGCCACCTTTACAGATGCGGAGA

TCGACGAGCTATTTGAGACAAGTGGAACTGTGATTGACAACATAATTAC

AGCCCAGGGTAAATCAGCAGAGACTGTTGGAAGGAGTGCAATCCCACAT

GGCAAAACCAAGGCGCTGAGCGCAGCATGGGAGAAGCATGGGAGCATCC

AGCCACCGGCCAGTCAAGACACCCCTGATCGACAGGACAGATCTGACAA

ACAACCATCCACACCCGAGCAAGCGACCCCGCATGACAGCCCGCCGGCC

ACATCCGCCGACCAGCCCCCCACCCAGGCCACAGACGAAGCCGTCGACA

CACAGCTCAGGACCGGAGCAAGCAACTCTCTGCTGTTGATGCTTGACAA

GCTCAGCAATAAATCGTCCAATGCTAAAAAGGGCCTATGGTCGAGCCCC

CAAGAGGGGAACCACCAACGTCCGACTCAACAGCAGGGAAGTCAACCCA

GCCGCGGAAACAGCCAGGAAAGACCGCAGAACCAAGTCAAGGCCGCCCC

TGGAAACCAGGGCACAGACGCGAACACAGCATATCATGGACAATGGGAG

GAGTCACAACTATCAGCTGGTGCAACCCCTCATGCTCTCCGATCAAGGC

AGAGCCAAGACAATACCCTTGTATCTGCGGATCATGTCCAGCCACCTGT

AGACTTTGTGCAAGCGATGATGTCTATGATGGAGGCAATATCACAGAGA

GTAAGTAAGGTTGACTATCAGCTAGATCTTGTCTTGAAACAGACATCCT

CCATCCCTATGATGCGGTCCGAAATCCAACAGCTGAAAACATCTGTTGC

AGTCATGGAAGCCAATTTGGGAATGATGAAGATTCTGGATCCCGGTTGT

GCCAACGTTTCATCTCTGAGTGATCTACGGGCAGTTGCCCGATCTCACC

CGGTTTTAGTTTCAGGCCCTGGAGACCCATCTCCCTATGTGACTCAAGG

AGGCGAAATGGCACTTAATAAACTTTCGCAACCAGTGCCACATCCATCT

GAATTGATTAAATCCGCCACTGCATGCGGGCCTGATATAGGAGTGGAAA

AGGACACTGTCCGTGCATTGATCATGTCACGCCCAATGCACCCGAGTTC

TTCAGCCAAGCTCCTAAGCAAGCTAGATGCAGCCGGGTCGATCGAGGAA

TABLE 4-continued

BC_CAT_.TXT (SEQ ID NO: 56)

ATCAGGAAAATCAAGCGCCTTGCACTAAATGGCTAATTACTACTGCCAC
ACGTAGCGGGTCCCCGTCCACTCGGCATCACACGGAATCTGCACCGAGT
CCCCCCCCGCAGACCTAAGGTCCAACTCTCCAAGTGGCAATCCTCTCTC
GCTTCCTCAGCCCCACTGAATGATCGCGCAACCGTAATTAATCTAGCTA
CATTAAGGATTAAGAAAAAATACGGGTAGAATTGGAGTGCCCCAATTGT
GCCAAGATGGACTCATCTAGGACAATTGGGCTGTACTTTGATTCTGCCC
ATTCTTCTAGCAACCTGTTAGCATTTCCGATCGTCCTACAAGACACAGG
AGATGGAAGAAGCAAATCGCCCCGCAATATAGGATCCAGCGCCTAGAC
TCGTGGACTGATAGTAAAGAAGACTCAGTATTCATCACCACCTATGGAT
TCATCTTTCAGGTTGGGAATGAAGAAGCCACTGTCGGCATGATCAATGA
TAATCCCAAGCGCGAGTTACTTTCTGCTGCGATGCTCTGCCTAGGAAGC
GTCCCAAATACCGGAGACCTTGTTGAGCTGGCAAGGGCCTGTCTCACTA
TGGTAGTCACATGCAAGAAGAGTGCAACTAATACTGAGAGAATGGTTTT
CTCAGTAGTGCAGGCACCCCAAGTGCTGCAAAGCTGTAGGGTTGTGGCA
AACAAATACTCATCAGTGAATGCAGTCAAGCACGTGAAAGCGCCAGAGA
AGATCCCCGGGAGTGGAACCCTAGAATACAAGGTGAACTTTGTCTCCTT
GACTGTGGTACCGAAGAAGGATGTCTACAAGATCCCAACTGCAGTATTG
AAGGTTTCTGGCTCGAGTCTGTACAATCTTGCGCTCAATGTCACTATTA
ATGTGGAGGTAGACTCGAGGAGTCCTTTGGTTAAATCTCTGTCTAAGTC
TGACAGCGGATACTATGCTAACCTCTTCTTGCATATTGGACTTATGACC
ACCGTAGATAGGAGGGGAAGAAAGTGACTTTTGACAAGCTAGAAAAGA
AGATAAGGAGCCTTGATCTATCTGTCGGGCTCAGTGATGTGCTCGGACC
TTCCGTGCTGGTAAAAGCAAGAGGTGCACGGACCAAGCTTTTGGCACCT
TTCTTCTCTAGCAGTGGGACAGCCTGCTATCCCATAGCAAATGCCTCTC
CTCAGGTGGCCAAGATACTCTGGAGTCAAACCGCGTGCCTGCGGAGCGT
TAAAATCATTATCCAAGCAGGTACCCAACGCACCGTCGCAGTGACCGCT
GACCACGAGGTTACCTCTACTAAGCTGGAGAAGGGGCACACCCTTGCCA
AATACAATCCTTTTAAGAAATAAGCTGCGTCTCTGAGATTGCGCTCCGC
CCACTCACCCAGAGCATCATGACACCAAAAACTAATCTGTCTTGATTAT
TTACAGTTAGTTTACCTGTCTATCAAATTAGAAAAAACACGGGTAGAAG
ATTCTGGATCCCGGTTGGCGCCTTCTAGGTGCAAGATGGGCCCCAGACC
TTCTACCAAGAACCCAGTACCTATGATGCTGACTGTCCGAGTCGCGCTG
GTACTGAGTTGCATCTGTCCGGCAAACTCCATTGATGGCAGGCCTCTTG
CGGCTGCAGGAATTGTGGTAACAGGAGACAAAGCAGTCAACATATACAC
CTCATCCCAGACAGGATCAATCATAGTTAAGCTCCTCCCAAACCTGCCC
AAGGATAAGGAGCATGTGCGAAAGCCCCCTTGGATGCATACAACAGGA
CATTGACCACTTTGCTCACCCCCCTTGGTGACTCTATCCGTAGGATACA
AGAGTCTGTAACTACATCTGGAGGGAGGAGACAGAAACGCTTTATAGGC
GCCATTATTGGCGGTGTGGCTCTTGGGGTTGCAACTGCTGCACAAATAA

TABLE 4-continued

BC_CAT_.TXT (SEQ ID NO: 56)

CAGCGGCCGCAGCTCTGATACAAGCCAAACAAAATGCTGCCAACATCCT
CCGACTTAAAGAGAGCATTGCCGCAACCAATGAGGCCGTGCATGAGGTC
ACTGACGGATTATCGCAACTAGCAGTGGCAGTTGGGAAGATGCAGCAGT
TTGTTAATGACCAATTTAATAAAACAGCTCAGGAATTAGGCTGCATCAG
AATTGCACAGCAAGTTGGTGTAGAGCTCAACCTGTACCTAACCGAATTG
ACTACAGTATTCGGACCACAAATCACTTCACCTGCCTTAAACAAGCTGA
CTATTCAGGCACTTTACAATCTAGCTGGTGGGAATATGGATTACTTGTT
GACTAAGTTAGGTGTAGGGAACAATCAACTCAGCTCATTAATCGGTAGC
GGCTTAATCACCGGCAACCCTATTCTGTACGACTCACAGACTCAACTCT
TGGGTATACAGGTAACTCTACCTTCAGTCGGGAACCTAAATAATATGCG
TGCCACCTACTTGGAAACCTTATCCGTAAGCACAACCAGGGGATTTGCC
TCGGCACTTGTCCCAAAAGTGGTGACACAGGTCGGTTCTGTGATAGAAG
AACTTGACACCTCATATTGTATAGAAACCGACTTGGATTTATATTGTAC
AAGAATAGTAACATTCCCTATGTCCCCTGGTATTTATTCCTGCTTGAGC
GGCAATACATCGGCCTGTATGTACTCAAAGACCGAAGGCGCACTCACTA
CGCCATACATGACTATCAAAGGCTCAGTCATCGCTAACTGCAAGATGAC
AACATGTAGATGTGTAAACCCCCCGGGTATCATATCGCAAAACTATGGA
GAAGCCGTGTCTCTAATAGATAAGCAATCATGCAATGTTTTATCCTTAG
ACGGGATAACTTTAAGGCTCAGTGGGGAATTCGATGCAACTTATCAGAA
GAATATCTCAATACAAGATTCTCAAGTAATAATAACAGGCAATCTTGAT
ATCTCAACTGAGCTTGGGAATGTCAACAACTCGATCAGTAATGCTTTGA
ATAAGTTAGAGGAAAGCAACAGCAAACTAGACAAAGTCAATGTCAAACT
GACCAGCACATCTGCTCTCATTACCTATATCGTTTTGACTATCATATCT
CTTGTTTTTGGTATACTTAGCCTGGTTCTAGCATGCTACCTAATGTATA
AGCAAAAGGCGCAACAAAAGACCTTATTATGGCTTGGGAATAATACCCT
AGATCAGATGAGAGCCACTACAAAAATGTGAACACAGATGAGGAACGAA
GGTATCCCTAATAGTAATTTGTGTGAAAGTTCTGGTAGTCTGTCAATTC
GGAGAGTTTAGAAAAAACTACGCGTTGTAGATGACCAAAGGACGATATA
CGGGTAGAACGGTAAGAGAGGCCGCCCCTCAATTGCGAGCCGGGCTTCA
CAACCTCCGTTCTACCGCTTCACCGACAGCAGTCCTCAGTCATGGACCG
CGCAGTTAGCCAAGTTGCGTTAGAGAATGATGAAAGAGAGGCAAAAAAT
ACATGGCGCTTGATATTCCGGATTGCAATCTTACTCTTAACAGTAGTGA
CCTTAGCTACATCTGTAGCCTCCCTTGTATATAGCATGGGGGCTAGCAC
ACCTAGCGACCTTGTAGGCATACCGACCAGGATTTCTAGGGCAGAAGAA
AAGATTACATCTGCACTTGGTTCCAATCAAGATGTAGTAGATAGGATAT
ATAAGCAAGTGGCCCTTGAGTCTCCGTTGGCATTGTTAAACACTGAGAC
CACAATTATGAACGCAATAACATCTCTCTTATCAGATTAATGGAGCT
GCGAACAACAGCGGGTGGGGGCACCTATCCATGACCCAGATTTTATCG
GGGGGATAGGCAAAGAACTCATTGTAGATGATGCTAGTGATGTCACATC

TABLE 4-continued

BC_CAT_.TXT (SEQ ID NO: 56)

ATTCTATCCCTCTGCATTTCAAGAACATCTGAATTTTATCCCGGCGCCT
ACTACAGGATCAGGTTGCACTCGGATACCTTCATTTGACATGAGTGCTA
CCCATTACTGCTACACTCATAATGTAATATTGTCTGGATGCAGAGATCA
CTCACACTCACATCAGTATTTAGCACTTGGTGTGCTCCGGACAACTGCA
ACAGGGAGGATATTCTTTTCTACTCTGCGTTCCATCAGTCTGGATGACA
CCCAAAATCGGAAGTCTTGCAGTGTGAGTGCAACTCCCTTAGGTTGTGA
TATGCTGTGCTCGAAAGTCACGGAGACAGAGGAAGAAGATTATAACTCA
GCTGTCCCTACGCTGATGGCACATGGGAGGTTAGGGTTCGACGGCCAAT
ACCACGAAAAGGACCTAGACGTCACAACATTATTTGAGGACTGGGTGGC
CAACTACCCAGGAGTAGGGGGTGGATCTTTTATTGACGGCCGCGTATGG
TTCTCAGTCTACGGAGGGCTGAAACCCAATTCACCCAGTGACACTGTAC
AGGAAGGGAAATATGTAATATACAAGCGATACAATGACACATGCCCAGA
TGAGCAAGACTACCAGATCCGAATGGCCAAGTCTTCGTATAAGCCCGGG
CGGTTTGGTGGGAAACGCATACAGCAGGCTATCTTATCTATCAAGGTGT
CAACATCTTTGGGCGAAGACCCAGTACTGACTGTACCGCCCAACACAGT
CACACTCATGGGGGCCGAAGGCAGAATTCTCACAGTAGGGACATCTCAT
TTCTTGTATCAGCGAGGGTCATCATACTTCTCTCCCGCGTTATTATATC
CTATGACAGTCAGCAACAAAACAGCCACTCTTCATAGTCCCTATACATT
CAATGCCTTCACTCGGCCAGGTAGTATCCCTTGCCAGGCTTCAGCAAGA
TGCCCCAACTCGTGTGTTACTGGAGTCTATACAGATCCATATCCCCTAA
TCTTCTATAGGAACCACACCTTGCGAGGGTATTCGGACAATGCTTGA
TAGTGAACAAGCAAGACTTAATCCTGCGTCTGCAGTATTCGATAGCACA
TCCCGCAGTCGCATAACTCGAGTGAGTTCAAGCAGCACCAAAGCAGCAT
ACACAACATCAACTTGTTTTAAAGTTGTCAAGACCAATAAGACCTATTG
TCTCAGCATTGCTGAAATATCTAATACTCTCTTCGGAGAATTCAGAATC
GTCCCGTTACTAGTTGAGATCCTCAAAAATGATGGGGTTAGAGAAGCCA
GGTCTGGTTAGTTGAGTCAACTATGAAAGAGCTGGGAAGATGGCATTGT
ATCACCTATCTTCCGCGACACCAAGAATCAAACTGAATGCCGGTGCGAG
CTCGAATTCCATGTCGCCAGTTGACCACAATCAGCCAGTGCTCATGCGA
TCAGATCAAGTCTTGTCAATAGTCCCTCGATTAAGAAAAAATGTAAGTG
GCAATGAGATACAAGGCAAAACAGCTACCGGTACGGGTAGAACGCCACC
ATGGAGAAAAAAATCACTGGATATACCACCGTTGATATATCCCAATGGC
ATCGTAAAGAACATTTTGAGGCATTTCAGTCAGTTGCTCAATGTACCTA
TAACCAGACCGTTCAGCTGGATATTACGGCCTTTTTAAAGACCGTAAAG
AAAAATAAGCACAAGTTTTATCCGGCCTTTATTCACATTCTTGCCCGCC
TGATGAATGCTCATCCGGAATTCCGTATGGCAATGAAAGACGGTGAGCT
GGTGATATGGGATAGTGTTCACCCTTGTTACACCGTTTTCCATGAGCAA
ACTGAAACGTTTTCATCGCTCTGGAGTGAATACCACGACGATTTCCGGC
AGTTTCTACACATATATTCGCAAGATGTGGCGTGTTACGGTGAAAACCT

GGCCTATTTCCCTAAAGGGTTTATTGAGAATATGTTTTTCGTCTCAGCC
AATCCCTGGGTGAGTTTCACCAGTTTTGATTTAAACGTGGCCAATATGG
ACAACTTCTTCGCCCCCGTTTTCACCATGGGCAAATACTATACGCAAGG
CGACAAGGTGCTGATGCCGCTGGCGATTCAGGTTCATCATGCCGTTTGT
GATGGCTTCCATGTCGGCAGAATGCTTAATGAATTACAACAGTACTGCG
ATGAGTGGCAGGGCGGGGCGTAATGATTAGAAAAAAACCGGTAAATAGT
ACGGGTAGGACATGGCGAGCTCCGGTCCTGAAAGGGCAGAGCATCAGAT
TATCCTACCAGAGTCACACCTGTCTTCACCATTGGTCAAGCACAAACTA
CTTTATTACTGGAAATTAACTGGGCTACCGCTTCCTGATGAATGTGACT
TCGACCACCTCATTCTCAGCAGACAATGGAAAAAAATACTTGAATCGGC
CTCTCCTGATACTGAGAGAATGATAAAACTCGGAAGGGCAGTACACCAA
ACTCTCAACCACAATTCTAGAATAACCGGAGTACTCCACCCCAGGTGTT
TAGAAGAACTGGCTAGTATTGAGGTCCCTGATTCAACCAACAAATTTCG
GAAGATTGAGAAGAAGATCCAAATTCACAACACGAGATATGGAGAACTG
TTCACAAGGCTGTGTACGCATATAGAGAAGAAACTGCTGGGGTCATCCT
GGTCTAACAATGTCCCCCGGTCAGAGGAGTTCAACAGCATCCGTACGGA
TCCGGCATTCTGGTTTCACTCAAAATGGTCCACAGCCAAGTTTGCATGG
CTCCATATAAAACAGATCCAGAGGCATCTGATTGTGGCAGCTAGGACAA
GGTCTGCGGCCAACAAATTGGTGATGCTAACCCATAAGGTAGGCCAAGT
CTTTGTCACTCCTGAACTTGTCATTGTGACGCATACGAATGAGAACAAG
TTCACATGTCTTACCCAGGAACTTGTATTGATGTATGCAGATATGATGG
AGGGCAGAGATATGGTCAACATAATATCAACCACGGCGGTGCATCTCAG
AAGCTTATCAGAGAAAATTGATGACATTTTGCAGTTAATAGACGCTCTG
GCAAAAGACTTGGGCAATCAAGTCTACGATGTTGTATCACTAATGGAGG
GATTTGCATACGGAGCTGTCCAGCTGCTCGAGCCGTCAGGTAGATTTGC
AGGACATTTCTTCGCATTCAACCTGCAGGAGCTTAAAGACATTCTAATC
GGCCTCCTCCCCAATGATATAGCAGAATCCGTGACTCATGCAATAGCTA
CTGTATTCTCTGGTTTAGAACAGAATCAAGCAGCTGAGATGTTGTGCCT
GTTGCGTCTGTGGGGTCACCCACTGCTTGAGTCCCGTATTGCAGCAAAG
GCAGTCAGGAGCCAAATGTGCGCACCGAAAATGGTGGACTTTGATATGA
TCCTTCAGGTACTGTCTTTCTTCAAGGGAACAATCATCAACGGATACAG
AAAGAAGAATGCAGGTGTGTGGCCGCGAGTCAAAGTGGATACAATATAT
GGGAAGATCATTGGGCAACTACATGCAGATTCAGCAGAGATTTCACACG
ATATCATGTTGAGAGAGTATAAGAGTTTATCTGCACTTGAATTTGAGCC
ATGTATAGAATACGACCCTGTCACTAACCTGAGCATGTTCCTAAAAGAC
AAGGCAATCGCACACCCTAACGATAATTGGCTTGCCTCGTTTAGGCGGA
ACCTTCTCTCCGAAGACCAGAAGAAACATGTAAAAGAAGCAACTTCGAC
TAATCGCCTCTTGATAGAGTTTTTAGAGTCAAATGATTTTGATCCTATA
AAAGAGATGGAATATCTGACGACCCTTGAGTACCTTAGAGATGACGATG

TABLE 4-continued

BC_CAT_.TXT (SEQ ID NO: 56)

TGGCAGTATCATACTCGCTCAAAGAGAAGGAAGTGAAAGTTAATGGACG
GATCTTCGCTAAGCTGACAAAGAAGTTAAGGAACTGTCAGGTGATGGCG
GAAGGGATCCTAGCCGACCAGATTGCACCTTTCTTTCAGGGAAATGGAG
TCATTCAGGATAGCATATCGTTGACCAAGAGTATGCTAGCGATGAGTCA
ACTGTCTTTTAACAGCAATAAGAAACGTATCACTGACTGTAAAGAAAGA
GTATCTTCAAACCGCAATCATGATCCGAAGAGCAAGAACCGTCGGAGAG
TTGCAACCTTCATAACAACTGACCTGCAAAAGTACTGTCTTAATTGGAG
ATATCAGACAATCAAACTGTTCGCTCATGCCATCAATCAGTTGATGGGC
CTACCTCACTTCTTTGAGTGGATTCACCTAAGACTGATGGACACTACAA
TGTTCGTAGGAGACCCTTTCAATCCTCCAAGTGACCCTACTGACTGTGA
CCTCTCAAGAGTCCCTAATGATGACATATATATTGTCAGTGCCAGAGGG
GGTATCGAAGGATTATGTCAGAAGCTATGGACAATGATCTCTATTGCTG
CAATCCAACTTGCTGCAGCTAGATCGCATTGTCGCGTTGCCTGTATGGT
ACAGGGTGATAATCAAGTAATAGCAGTAACGAGAGAGGTAAGATCAGAC
GACTCTCCGGAGATGGTGTTGACACAGTTGCATCAAGCCAGTGATAATT
TCTTCAAGGAATTAATTCATGTCAATCATTTGATTGGCCATAATTTGAA
GGACCGTGAAACCATCAGGTCAGACACATTCTTCATATACAGCAAACGA
ATCTTCAAAGATGGAGCAATCCTCAGTCAAGTCCTCAAAAATTCATCTA
AATTAGTACTGGTGTCAGGTGATCTCAGTGAAAACACCGTAATGTCCTG
TGCCAACATTGCCTCTACTGTAGCACGGCTATGCGAGAACGGGCTTCCC
AAGGACTTCTGTTACTATTTAAACTATATAATGAGTTGCGTGCAGACAT
ACTTTGACTCTGAGTTCTCCTACAACAACAATTCGCACCCCGATCTTAA
CCAGTCGTGGATTGAGGACATCTCTTTTGTGCACTCATATGTTCTGACT
CCTGCCCAATTAGGGGGACTTAGTAACCTTCAATACTCAAGGCTCTACA
CTAGAAATATCGGTGACCCGGGGACTACTGCTTTTGCAGAGATCAAGCG
ACTAGAAGCAGTGGGATTACTGAGTCCTAACATTATGACTAATATCTTA
ACTAGGCCGCCTGGGAATGGAGATTGGGCCAGTCTTTGCAACGACCCAT
ACTCTTTCAATTTTGAGACTGTTGCAAGCCCAAACATTGTTCTTAAGAA
ACATACGCAAAGAGTCCTATTTGAAACTTGTTCAAATCCCTTATTGTCT
GGAGTGCACACAGAGGATAATGAGGCAGAAGAGAAGGCATTGGCTGAAT
TCTTGCTTAATCAAGAGGTGATTCATCCCCGCGTTGCGCATGCTATCAT
GGAGGCAAGCTCTGTAGGTAGGAGAAAGCAAATTCAAGGGCTTGTTGAC
ACAACAAACACCGTAATTAAGATTGCACTTACTAGGAGGCCACTAGGCA
TCAAGAGGCTGATGCGGATAGTCAATTATTCTAGCATGCATGCAATGCT
GTTTAGAGACGATGTTTTTTCCTCCAATAGATCCAACCACCCCTTAGTC
TCTTCTAATATGTGTTCTCTGACACTGGCAGACTATGCACGGAATAGAA
GCTGGTCACCTTTGACGGGAGGCAGGAAAATACTGGGTGTATCTAATCC
TGATACGATAGAACTCGTAGAGGGTGAGATTCTTAGTGTAAGCGGAGGG
TGCACAAGATGCGACAGCGGAGATGAACAGTTTACTTGGTTCCATCTTC

CAAGCAATATAGAATTGACCGATGACACCAGCAAGAATCCTCCGATGAG
AGTACCATATCTCGGGTCAAAGACACAGGAGAGGAGAGCTGCCTCACTT
GCGAAAATAGCTCATATGTCGCCACATGTGAAGGCTGCCCTAAGGGCAT
CATCCGTGTTGATCTGGGCTTATGGGGATAATGAAGTAAATTGGACTGC
TGCTCTTACGATTGCAAAATCTCGATGTAATATAAACTTAGAGTATCTT
CGGTTATTGTCCCCTTTACCCACGGCTGGGAATCTTCAACATAGACTAG
ATGATGGTATAACTCAGATGACATTCACCCCTGCATCTCTCTACAGGGT
GTCACCTTACATTCACATATCCAATGATTCTCAAAGGCTATTCACTGAA
GAAGGAGTCAAAGAGGGGAATGTGGTTTATCAACAGATCATGCTCTTGG
GTTTATCTCTAATCGAATCGATCTTTCCAATGACGACAACCAGGACATA
TGATGAGATCACATTGCATCTACATAGTAAATTTAGTTGCTGTATCAGG
GAAGCACCTGTTGCGGTTCCTTTCGAGCTACTTGGGGTGGCACCGGAGC
TAAGGACAGTGACCTCAAACAAGTTTATGTATGATCCTAGCCCTGTATC
GGAGGGAGACTTTGCGAGACTTGACTTAGCTATCTTCAAGAGTTATGAG
CTTAATCTGGAGTCATATCCCACGATAGAGCTAATGAACATTCTTTCAA
TATCCAGCGGGAAGTTGATTGGCCAGTCTGTGGTTTCTTATGATGAAGA
TACCTCCATAAAGAATGACGCCATAATAGTGTATGACAATACCCGAAAT
TGGATCAGTGAAGCTCAGAATTCAGATGTGGTCCGCTTATTTGAATATG
CAGCACTTGAAGTGCTCCTCGACTGTTCTTACCAACTCTATTATCTGAG
AGTAAGAGGCCTAGACAATATTGTCTTATATATGGGTGATTTATACAAG
AATATGCCAGGAATTCTACTTTCCAACATTGCAGCTACAATATCTCATC
CCGTCATTCATTCAAGGTTACATGCAGTGGGCCTGGTCAACCATAACGG
ATCACACCAACTTGCAGATACGGATTTTATCGAAATGTCTGCAAAACTG
TTAGTATCTTGCACTCGACGTGTGATCTCCGGCTTATATTCAGGGAATA
AGTATGATCTGCTGTTCCCATCTGTCTTAGATGATAACCTGAATGAGAA
GATGCTTCAGCTGATATCCCGGTTATGCTGTCTGTACACGGTACTCTTT
GCTACAACAAGAGAAATCCCGAAAATAAGAGGCTTATCTGCAGAAGAGA
AATGTTCAGTACTTACTGAGTATCTACTGTCGGATGCTGTGAAACCATT
ACTTAGCCCTGATCAGGTGAGCTCTATCATGTCTCCTAACATAATTACA
TTCCCAGCTAATCTGTACTACATGTCTCGGAAGAGCCTCAATTTGATCA
GGGAAAGGGAGGACAAGGATTCTATCCTGGCGTTGTTGTTCCCCCAAGA
GCCATTATTAGAGTTCCCTTCTGTGCAAGATATTGGTGCTCGAGTGAAA
GATCCATTCACCCGACAACCTGCGGCATTTTTGCAAGAGTTAGATTTGA
GTGCTCCAGCAAGGTATGACGCATTCACACTTAGTCAGATTCATCCTGA
GCTCACATCACCAAATCCGGAGGAAGACTACTTAGTACGATACTTGTTC
AGAGGAATAGGGACTGCATCCTCCTCTTGGTATAAGGCATCCCATCTCC
TTTCTGTACCCGAGGTAAGATGTGCAAGACACGGGAACTCCTTATACTT
AGCTGAAGGAAGCGGAGCCATCATGAGTCTTCTCGAACTGCATGTACCA
CATGAAACTATCTATTACAATACGCTCTTTTCAAATGAGATGAACCCCC

TABLE 4-continued

BC_CAT_.TXT (SEQ ID NO: 56)

CGCAGCGACATTTCGGGCCGACCCCAACCCAGTTTTTGAATTCGGTTGT

TTATAGGAACCTACAGGCGGAGGTAACATGCAAGGATGGATTTGTCCAA

GAGTTCCGTCCACTATGGAGAGAAAATACAGAGGAAAGCGACCTGACCT

CAGATAAAGCAGTGGGGTATATTCATCTGCAGTGCCCTACAGATCTGT

ATCATTGCTGCATTGTGACATTGAAATCCCTCCAGGGTCCAATCAAAGC

TTACTAGATCAATTAGCTATCAATTTATCTCTGATTGCCATGCATTCCG

TAAGGGAGGGCGGGGTAGTGATCATCAAAGTGTTGTATGCAATGGGATA

CTACTTTCATCTACTCATGAACTTGTTCGCTCCGTGTTCCACAAAAGGA

TACATTCTCTCTAATGGTTATGCATGTAGAGGGGATATGGAGTGTTACC

TGGTATTTGTCATGGGTTACCTGGGCGGGCCTACATTTGTACACGAGGT

GGTGAGGATGGCAAAAACTCTGGTGCAGCGGCACGGTACGCTTTTGTCC

AAATCAGATGAGATCACACTGACCAGGTTATTCACCTCACAGCGGCAGC

GTGTGACAGACATCCTATCCAGTCCTTTACCAAGATTAATAAAGTACTT

GAGAAAGAATATTGACACTGCGCTGATTGAAGCTGGGGGACAGCCCGTC

CGTCCATTCTGTGCAGAGAGTTTGGTGAGCACGCTGGCGGACATAACTC

AGATAACCCAGATCATTGCTAGTCACATTGACACAGTCATCCGGTCTGT

GATATATATGGAAGCTGAGGGTGATCTCGCTGACACAGTATTTCTATTT

ACCCCTTACAATCTCTCTACTGACGGGAAAAAGAGAACATCACTTAAAC

AGTGCACGAGACAGATCCTAGAGGTTACAATATTGGGTCTTAGAGTCGA

AGATCTCAATAAAATAGGCGATGTAATCAGCCTAGTGCTTAAAGGCATG

ATCTCCATGGAGGACCTTATCCCACTAAGGACATACTTGAAGCATAGTA

CCTGCCCTAAATATTTGAAGGCTGTCCTAGGTATTACCAAACTCAAAGA

AATGTTTACAGACACCTCTGTATTGTACTTGACTCGTGCTCAACAAAAA

TTCTACATGAAAACTATAGGCAATGCAGTCAAAGGATATTACAGTAACT

GTGACTCTTAACGAAAATCACATATTAATAGGCTCCTTTTCTGGCCAAT

TGTATCCTTGGTGATTTAATTATACTATGTTAGAAAAAAATTGAACTCC

GACTCCTTAGATCTCGAATTCGAACTCAAATAAATGTCTTAAAAAAAGG

TTGCGCACAATTATTCTTGAGTGTAGTCTTGTTATTCACCAAATCTTTG

TTTGGT

---

The invention claimed is:

1. An antigenomic RNA of Newcastle disease virus, consisting of:

NP gene, P gene, M gene, F gene, HN gene and L gene in this order from a 5' to 3' direction, a 55 nucleotide 3' leader, a 113 nucleotide 5' terminus, and n foreign nucleotide complexes inserted (a) before the NP gene, (b) between the P and M genes, and/or (c) between the HN and L genes, wherein n is 1, 2, 3 or 4;

each of the foreign nucleotide complexes comprising a Newcastle disease virus gene start sequence, an open reading frame of a foreign gene and a Newcastle disease virus gene end sequence in this order from the 5' to 3' direction, wherein the foreign gene is a gene not found naturally in the Newcastle disease virus;

wherein when 2, 3 or 4 foreign nucleotide complexes are inserted together before the NP gene, between the P and M genes, or between the HN and L genes, the foreign nucleotide complexes are sequentially linked directly or indirectly;

wherein the antigenomic RNA of Newcastle disease virus has a length of m nucleotides, wherein m is a multiple of 6, wherein three G residues are inserted before the 5' terminus, and wherein the Newcastle disease virus has an $F_0$ protein cleavage site having at least two less basic amino acid residues than an $F_0$ protein cleavage site of a virulent strain of Newcastle disease virus, wherein codons of non-basic amino acid residues replacing the at least two basic amino acid residues are different from codons of the basic amino acid residues by at least two nucleotides, and wherein an amino acid having a non-aromatic side chain at the N terminus of an $F_1$ cleavage fragment is glycine, alanine, valine, leucine or isoleucine.

2. The antigenome RNA of claim 1, wherein n is 2, 3 or 4 and the foreign nucleotide complexes are different.

3. The antigenome RNA of claim 1, wherein n is 2, 3 or 4 and the foreign nucleotide complexes are the same.

4. The antigenome RNA of claim 1, wherein n is 1 or 2.

5. The antigenome RNA of claim 4, wherein n is 2 and the foreign nucleotide complexes are different.

6. The antigenome RNA of claim 4, wherein n is 2 and the foreign nucleotide complexes are the same.

7. The antigenome RNA of claim 1, wherein the length of the open reading frame of the foreign gene is no more than about 3000 nucleotides.

8. The antigenome RNA of claim 7, wherein the length of the open reading frame of the foreign gene is no more than about 1500 nucleotides.

9. The antigenome RNA of claim 8, wherein the length of the open reading frame of the foreign gene is no more than about 1000 nucleotides.

10. The antigenome RNA of claim 9, wherein the length of the open reading frame of the foreign gene is no more than about 800 nucleotides.

11. The antigenome RNA of claim 10, wherein the length of the open reading frame of the foreign gene is no more than about 500 nucleotides.

12. The antigenome RNA of claim 11, wherein the length of the open reading frame of the foreign gene is no more than about 300 nucleotides.

13. The antigenome RNA of claim 1, wherein 2, 3 or 4 foreign nucleotide complexes are inserted together before the NP gene, between the P and M genes, or between the HN and L genes, the sequentially linked foreign nucleotide complexes having a combined length of no more than about 5000 nucleotides.

14. The antigenomic RNA of claim 13, wherein the sequentially linked foreign nucleotide complexes have a combined length of no more than about 2000 nucleotides.

15. The antigenomic RNA of claim 14, wherein the sequentially linked foreign nucleotide complexes have a combined length of no more than about 1000 nucleotides.

16. The antigenomic RNA of claim 15, wherein the sequentially linked foreign nucleotide complexes have a combined length of no more than about 800 nucleotides.

17. The antigenomic RNA of claim 1, wherein the foreign genes of the foreign nucleotide complexes are selected from the group consisting of genes encoding chloramphenical acetyltransferase, green fluorescent protein, an avian cytokine, and an immunogenic protein of a virus selected from the group consisting of influenza virus, infectious bursal disease virus, rotavirus, infectious bronchitis virus, infectious laryngotracheitis virus, chicken anemia virus, Marek's disease virus, avian leukosis virus, avian adenovirus, and avian pneumovirus.

18. The antigenomic RNA of claim 1, wherein the foreign genes of the foreign nucleotide complexes encode chloramphenical acetyltransferase.

19. The antigenomic RNA of claim 1, wherein the foreign genes of the foreign nucleotide complexes encode the same or different avian cytokines.

20. The antigenomic RNA of claim 19, wherein the avian cytokines are avian interleukins.

21. The antigenomic RNA of claim 20, wherein the avian cytokines are avian IL-2 and/or IL-4.

22. The antigenomic RNA of claim 1, wherein the foreign genes of the foreign nucleotide complexes encode an immunogenic protein of the same or different viruses selected from the group consisting of influenza virus, infectious bursal disease virus, rotavirus, infectious bronchitis virus, infectious laryngotracheitis virus, chicken anemia virus, Marek's disease virus, avian leukosis virus, avian adenovirus and avian pneumovirus.

23. The antigenomic RNA of claim 1, wherein the n foreign nucleotide complexes are inserted (a) before the NP gene, and/or (b) between the P and M genes.

24. The antigenomic RNA of claim 23, wherein the n foreign nucleotide complexes are inserted before the NP gene.

25. The antigenome RNA of claim 24, wherein 2, 3 or 4 foreign nucleotide complexes are inserted together before the NP gene, the sequentially linked foreign nucleotide complexes having a combined length of no more than about 4000 nucleotides.

26. The antigenomic RNA of claim 25, wherein the sequentially linked foreign nucleotide complexes have a combined length of no more than about 2000 nucleotides.

27. The antigenomic RNA of claim 26, wherein the sequentially linked foreign nucleotide complexes have a combined length of no more than about 1000 nucleotides.

28. The antigenomic RNA of claim 27, wherein the sequentially linked foreign nucleotide complexes have a combined length of no more than about 800 nucleotides.

29. The antigenomic RNA of claim 23, wherein the n foreign nucleotide complexes are inserted between the P and M genes.

30. The antigenomic RNA of claim 29, wherein the sequentially linked foreign nucleotide complexes have a combined length of no more than about 4000 nucleotides.

31. The antigenomic RNA of claim 30, wherein the sequentially linked foreign nucleotide complexes have a combined length of no more than about 2000 nucleotides.

32. The antigenomic RNA of claim 31, wherein the sequentially linked foreign nucleotide complexes have a combined length of no more than about 1000 nucleotides.

33. The antigenomic RNA of claim 32, wherein the sequentially linked foreign nucleotide complexes have a combined length of no more than about 800 nucleotides.

34. The antigenomic RNA of claim 18, wherein n is 1.

35. The antigenomic RNA of claim 19, wherein n is 1.

36. The antigenomic RNA of claim 22, wherein n is 1.

37. The antigenomic RNA of claim 24, wherein n is 1.

38. The antigenomic RNA of claim 37, wherein the open reading frame of the foreign gene encodes chloramphenicol acetyltransferase.

39. The antigenomic RNA of claim 37, wherein the open reading frame of the foreign gene encodes an avian cytokine.

40. The antigenomic RNA of claim 39, wherein the avian cytokine is an avian interleukin.

41. The antigenomic RNA of claim 40, wherein the avian interleukin is IL-2 or IL-4.

42. The antigenomic RNA of claim 1, wherein at least one of the foreign nucleotide complexes contain foreign gene encoding an immunogenic protein of a non-avian pathogen.

43. The antigenomic RNA of claim 42, wherein the non-avian pathogen is a virus selected from the group consisting of influenza virus, SARS-causing virus, human respiratory syncytial virus, human immunodeficiency virus, hepatitis A virus, hepatitis B virus, hepatitis C virus, poliovirus, rabies virus, Hendra virus, Nipah virus, human parainfluenza 3 virus, measles virus, mumps virus, Ebola virus, Marburg virus, West Nile virus, Japanese encephalitis virus, Dengue virus, Hantavirus, Rift Valley fever virus, Lassa fever virus, herpes simplex virus and yellow fever virus.

44. A plasmid comprising a cDNA that encodes for an antigenomic RNA comprising:
NP gene, P gene, M gene, F gene, HN gene and L gene in this order from a 5' to 3' direction, a 55 nucleotide 3' leader, a 113 nucleotide 5' terminus, and n foreign nucleotide complexes inserted (a) before the NP gene, (b) between the P and M genes, and/or (c) between the HN and L genes, wherein n is 1, 2, 3 or 4;
each of the foreign nucleotide complexes comprising a Newcastle disease virus gene start sequence, an open reading frame of a foreign gene and a Newcastle disease virus gene end sequence in this order from the 5' to 3' direction, wherein the foreign gene is a gene not found naturally in the Newcastle disease virus;
wherein when 2, 3 or 4 foreign nucleotide complexes are inserted together before the NP gene, between the P and M genes, or between the HN and L genes, the foreign nucleotide complexes are sequentially linked directly or indirectly;
wherein the antigenomic RNA of Newcastle disease virus has a length of m nucleotides, wherein m is a multiple of 6,
wherein three G residues are inserted before the 5' terminus; and
wherein the Newcastle disease virus comprises an $F_0$ protein cleavage site having at least two less basic amino acid residues than an $F_0$ protein cleavage site of a virulent strain of Newcastle disease virus, wherein codons of non-basic amino acid residues replacing the at least two basic amino acid residues are different from codons of the basic amino acid residues by at least two nucleotides, and wherein an amino acid having a non-aromatic side chain at the N terminus of an $F_1$ cleavage fragment is glycine, alanine, valine, leucine or isoleucine.

45. A cell comprising the plasmid of claim 44.

46. A cell comprising the antigenomic RNA of claim 1.

47. The antigenomic RNA of claim 1, wherein at least one of the foreign nucleotide complexes is inserted before the NP gene.

48. The antigenomic RNA of claim 1, wherein at least one of the foreign nucleotide complexes is inserted before the NP gene and at least one of the foreign nucleotide complexes is inserted between the P and M genes.

49. The antigenomic RNA of claim 1, wherein at least one of the foreign nucleotide complexes is inserted before the NP gene and at least one of the foreign nucleotide complexes is inserted between the HN and L genes.

50. The antigenomic RNA of claim 1, wherein at least one of the foreign nucleotide complexes is inserted before the NP gene, at least one of the foreign nucleotide complexes is inserted between the P and M genes, and at least one of the foreign nucleotide complexes is inserted between the HN and L genes.

51. The antigenomic RNA of claim 1, wherein at least one of the foreign nucleotide complexes is inserted between the P and M genes.

52. The antigenomic RNA of claim 1, further comprising at least one intergenic region selected from the group consisting of a NP-P intergenic region between the NP and P genes, a P-M intergenic region between the P and M genes, a M-F intergenic region between the M and F genes, a F-HN intergenic region between the F and HN genes, and a HN-L intergenic region between the HN and L genes.

53. The antigenomic RNA of claim 1, further comprising a NP-P intergenic region between the NP and P genes, a P-M intergenic region between the P and M genes, a M-F intergenic region between the M and F genes, a F-HN intergenic region between the F and HN genes, and a HN-L intergenic region between the HN and L genes.

54. The antigenomic RNA of claim 1, wherein the foreign gene of at least one of the foreign nucleotide complexes encodes a tumor antigen.

55. The antigenomic RNA of claim 54, wherein the tumor antigen is selected from the group consisting of pg100, MAGE1, MAGE3 and CDK4.

56. A recombinant Newcastle disease virus comprising the antigenomic RNA of claim 1, wherein the foreign genes of the foreign nucleotide complexes encode an immunogenic protein of infectious bursal disease.

57. The antigenomic RNA of claim 1, wherein at least one foreign nucleotide complex is inserted between the P and M genes and at least one foreign nucleotide complex is inserted before the NP gene.

58. The antigenomic RNA of claim 18, wherein the foreign genes of the foreign nucleotide complexes that encode chloramphenical acetyltransferase are inserted between the HN and L genes and before the NP gene.

59. The antigenomic RNA of claim 17, wherein the foreign genes of the foreign nucleotide complexes encode green fluorescent protein.

60. The antigenomic RNA of claim 59, wherein the foreign genes of the foreign nucleotide complexes that encode green fluorescent protein are inserted between the P and M genes.

* * * * *